US008802645B2

(12) United States Patent
Van Ommen et al.

(10) Patent No.: US 8,802,645 B2
(45) Date of Patent: Aug. 12, 2014

(54) MOLECULE FOR TREATING AN INFLAMMATORY DISORDER

(75) Inventors: Garrit-Jan Boudewijn Van Ommen, Amsterdam (NL); Annemieke Aartsma-Rus, Hoofddorp (NL); Judith Christina Theodora Van Deutekom, Dordrecht (NL); Josephus Johannes De Kimpe, Utrecht (NL); Joseph Stephan Verbeek, Leiden (NL); Aliye Seda Ylmaz-Elis, Hoofddorp (NL)

(73) Assignees: Prosensa Technologies B.V., Leiden (NL); Academisch Ziekenhuis Leiden H.O.D.N. LUMC, Leiden (NL)

( * ) Notice: Subject to any disclaimer, the term of this patent is extended or adjusted under 35 U.S.C. 154(b) by 0 days.

(21) Appl. No.: 13/529,640

(22) Filed: Jun. 21, 2012

(65) Prior Publication Data

US 2012/0259002 A1    Oct. 11, 2012

Related U.S. Application Data

(63) Continuation of application No. PCT/NL2010/050882, filed on Dec. 22, 2010.

(60) Provisional application No. 61/290,102, filed on Dec. 24, 2009.

(30) Foreign Application Priority Data

Dec. 24, 2009   (EP) ..................................... 09180760

(51) Int. Cl.
| A61K 31/70 | (2006.01) |
| C07H 21/02 | (2006.01) |
| C07H 21/04 | (2006.01) |
| C12N 15/113 | (2010.01) |
| C12N 15/11 | (2006.01) |
| C12Q 1/68 | (2006.01) |

(52) U.S. Cl.
CPC ............ *C12N 15/113* (2013.01); *C12N 15/111* (2013.01); *C12N 2310/11* (2013.01); *C12N 2320/33* (2013.01); *C12N 2320/30* (2013.01)
USPC ....... 514/44 A; 536/23.1; 536/24.1; 536/24.5; 435/375; 435/377

(58) Field of Classification Search
None
See application file for complete search history.

(56) References Cited

U.S. PATENT DOCUMENTS

| 5,034,506 A | 7/1991 | Summerton et al. .......... 528/391 |
| 5,418,139 A | 5/1995 | Campbell ..................... 435/7.21 |
| 5,541,308 A | 7/1996 | Hogan et al. ................. 536/23.1 |
| 5,593,974 A | 1/1997 | Rosenberg et al. ............ 514/44 |
| 5,608,046 A | 3/1997 | Cook et al. ................... 536/23.1 |
| 5,624,803 A | 4/1997 | Noonberg et al. ................. 435/6 |
| 5,627,263 A | 5/1997 | Ruoslahti et al. ............. 530/327 |
| 5,658,764 A | 8/1997 | Pergolizzi et al. ........... 435/91.2 |
| 5,741,645 A | 4/1998 | Orr et al. ........................... 435/6 |
| 5,766,847 A | 6/1998 | Jäckle et al. ...................... 435/6 |
| 5,853,995 A | 12/1998 | Lee .................................. 435/6 |
| 5,869,252 A | 2/1999 | Bouma et al. ..................... 435/6 |
| 5,916,808 A | 6/1999 | Kole et al. ..................... 435/375 |
| 5,962,332 A | 10/1999 | Singer et al. ..................... 436/94 |
| 5,968,909 A | 10/1999 | Agrawal et al. ................ 514/44 |
| 5,976,879 A | 11/1999 | Kole et al. ..................... 435/375 |
| 6,124,100 A | 9/2000 | Jin ................................... 435/6 |
| 6,130,207 A | 10/2000 | Dean et al. ..................... 514/44 |
| 6,133,031 A | 10/2000 | Monia et al. ................. 435/375 |
| 6,172,208 B1 | 1/2001 | Cook .......................... 536/23.1 |
| 6,172,216 B1 | 1/2001 | Bennett et al. .............. 536/24.5 |
| 6,210,892 B1 | 4/2001 | Bennett et al. .................. 435/6 |
| 6,251,589 B1 | 6/2001 | Tsuji et al. ....................... 435/6 |
| 6,280,938 B1 | 8/2001 | Ranum et al. .................... 435/6 |
| 6,300,060 B1 | 10/2001 | Kantoff et al. ................... 435/6 |
| 6,322,978 B1 | 11/2001 | Kahn et al. ....................... 435/6 |
| 6,329,501 B1 | 12/2001 | Smith et al. .................. 530/329 |
| 6,355,481 B1 | 3/2002 | Li et al. ........................ 435/331 |
| 6,355,690 B1 | 3/2002 | Tsuji .............................. 514/706 |
| 6,369,038 B1 | 4/2002 | Blumenfeld et al. ........... 514/44 |
| 6,379,698 B1 | 4/2002 | Leamon ........................ 424/450 |
| 6,399,575 B1 | 6/2002 | Smith et al. ..................... 514/16 |
| 6,514,755 B1 | 2/2003 | Ranum et al. .............. 435/320.1 |
| 6,623,927 B1 | 9/2003 | Brahmachari et al. ............ 435/6 |
| 6,653,466 B2 | 11/2003 | Matsuo ........................ 536/24.3 |

(Continued)

FOREIGN PATENT DOCUMENTS

| CA | 2319149 | 10/2001 | ............ C07H 21/00 |
| CA | 2526893 | 11/2004 | ......... A61K 31/7008 |

(Continued)

OTHER PUBLICATIONS

Yilmaz-Elis et al., Molecular Therapy—Nucleic Acids vol. 2, e66, 2013, 8 pages.*

Karras, J. et al. Peptide Nucleic Acids Are Potent Modulators of Endogenous Pre-mRNA Splicing of the Murine Interleukin-5 Receptor-α Chain.

Graziewicz et al., "An Endogenous TNF-α Antagonist Induced by Splice-switching Oligonucleotides Reduces Inflammation in Hepatitis and Arthritis Mouse Models," Molecular Therapy (2008), 16(7):1316-1322.

Jensen et al., "IL-1 Signaling Cascade in Liver Cells and the Involvement of a Soluble Form of the IL-1 Receptor Accessory Protein", The Journal of Immunology (2000), 164:5277-5286.

(Continued)

*Primary Examiner* — Sean McGarry
(74) *Attorney, Agent, or Firm* — Sunstein Kann Murphy & Timbers LLP

(57) ABSTRACT

The invention provides two types of oligonucleotides for treating an inflammatory disorder: an oligonucleotide which is able of altering the splicing of a pre-mRNA encoding a C5 in order to decrease the amount of a C5a and an oligonucleotide which is able of altering the splicing of a pre-mRNA encoding a IL-1RAcP in order to increase the amount of a soluble IL-1RAcP. The invention further provides the use of said oligonucleotides for preventing or treating an inflammatory disorder.

23 Claims, 7 Drawing Sheets

(56) References Cited

U.S. PATENT DOCUMENTS

| | | | |
|---|---|---|---|
| 6,653,467 B1 | 11/2003 | Matsuo et al. | 536/24.5 |
| 6,670,461 B1 | 12/2003 | Wengel et al. | |
| 6,727,355 B2 | 4/2004 | Matsuo et al. | 536/24.5 |
| 6,794,192 B2 | 9/2004 | Parums et al. | 436/15 |
| 6,902,896 B2 | 6/2005 | Ranum et al. | 435/6 |
| 6,982,150 B2 | 1/2006 | Sheetz et al. | 435/7.2 |
| 7,001,994 B2 | 2/2006 | Zhu | 536/4.1 |
| 7,034,009 B2 | 4/2006 | Pavco et al. | 514/44 |
| 7,118,893 B2 | 10/2006 | Ranum et al. | 435/91.2 |
| 7,189,530 B2 | 3/2007 | Botstein et al. | 435/69.1 |
| 7,202,210 B2 | 4/2007 | Wolfman et al. | 514/12 |
| 7,250,404 B2 | 7/2007 | Felgner et al. | 514/44 |
| 7,320,965 B2 | 1/2008 | Sah et al. | 514/44 |
| 7,355,018 B2 | 4/2008 | Glass | 530/399 |
| 7,405,193 B2 | 7/2008 | Lodish et al. | 514/2 |
| 7,442,782 B2 | 10/2008 | Ranum et al. | 536/23.1 |
| 7,514,551 B2 | 4/2009 | Rabbani et al. | 536/26.6 |
| 7,534,879 B2 | 5/2009 | van Deutekom | 536/24.5 |
| 7,589,189 B2 | 9/2009 | Ichiro et al. | 536/24.5 |
| 7,655,785 B1 | 2/2010 | Bentwich | 536/24.1 |
| 7,771,727 B2 | 8/2010 | Fuselier et al. | 424/185.1 |
| 7,807,816 B2 | 10/2010 | Wilton et al. | 536/24.5 |
| 7,902,160 B2 | 3/2011 | Matsuo et al. | 514/44 |
| 7,960,541 B2 | 6/2011 | Wilton et al. | 536/24.5 |
| 8,084,601 B2 | 12/2011 | Popplewell et al. | 536/24.5 |
| 8,232,384 B2 | 7/2012 | Wilton et al. | 536/24.5 |
| 8,324,371 B2 | 12/2012 | Popplewell et al. | 536/24.5 |
| 8,450,474 B2 | 5/2013 | Wilton et al. | 536/24.5 |
| 8,455,634 B2 | 6/2013 | Wilton et al. | 536/24.5 |
| 8,455,635 B2 | 6/2013 | Wilton et al. | 536/24.5 |
| 8,455,636 B2 | 6/2013 | Wilton et al. | 536/24.5 |
| 8,476,423 B2 | 7/2013 | Wilton et al. | 536/24.5 |
| 8,486,907 B2 | 7/2013 | Wilton et al. | 514/44 |
| 8,524,880 B2 | 9/2013 | Wilton et al. | 536/24.5 |
| 8,637,483 B2 | 1/2014 | Wilton et al. | 514/44 A |
| 2001/0056077 A1 | 12/2001 | Matsuo | 514/44 |
| 2002/0049173 A1 | 4/2002 | Bennett et al. | 514/44 |
| 2002/0055481 A1 | 5/2002 | Matsuo et al. | 514/44 |
| 2002/0115824 A1 | 8/2002 | Engler et al. | 530/324 |
| 2002/0165150 A1 | 11/2002 | Ben-Sasson | 514/12 |
| 2003/0073215 A1 | 4/2003 | Baker et al. | 435/183 |
| 2003/0082763 A1 | 5/2003 | Baker et al. | 435/183 |
| 2003/0082766 A1 | 5/2003 | Baker et al. | 435/183 |
| 2003/0109476 A1 | 6/2003 | Kmiec et al. | 514/44 |
| 2003/0124523 A1 | 7/2003 | Asselbergs et al. | 435/6 |
| 2003/0134790 A1 | 7/2003 | Langenfeld | 514/12 |
| 2003/0235845 A1 | 12/2003 | Van Ommen et al. | 435/6 |
| 2003/0236214 A1 | 12/2003 | Wolff et al. | 514/44 |
| 2004/0101852 A1 | 5/2004 | Bennett et al. | 435/6 |
| 2004/0132684 A1 | 7/2004 | Sampath et al. | 514/44 |
| 2004/0226056 A1 | 11/2004 | Roch et al. | 800/12 |
| 2005/0096284 A1 | 5/2005 | McSwiggen | 514/44 |
| 2005/0222009 A1 | 10/2005 | Lamensdorf et al. | 514/7 |
| 2005/0246794 A1 | 11/2005 | Khvorova et al. | 800/286 |
| 2005/0277133 A1 | 12/2005 | McSwiggen | 435/6 |
| 2006/0074034 A1 | 4/2006 | Collins et al. | 514/44 |
| 2006/0148740 A1 | 7/2006 | Platenburg | 514/44 |
| 2007/0021360 A1 | 1/2007 | Nyce et al. | 514/44 |
| 2007/0082861 A1 | 4/2007 | Matsuo et al. | 514/44 |
| 2007/0141628 A1 | 6/2007 | Cunningham et al. | 435/7.1 |
| 2007/0275914 A1 | 11/2007 | Manoharan et al. | 514/44 |
| 2007/0292408 A1 | 12/2007 | Singh et al. | 424/130.1 |
| 2008/0015158 A1 | 1/2008 | Ichiro et al. | 514/44 |
| 2008/0039418 A1 | 2/2008 | Freier | 514/44 |
| 2008/0113351 A1 | 5/2008 | Naito et al. | 435/6 |
| 2008/0200409 A1 | 8/2008 | Wilson et al. | 514/44 |
| 2008/0207538 A1 | 8/2008 | Lawrence et al. | 514/41 |
| 2008/0249294 A1 | 10/2008 | Haeberli et al. | 536/24.5 |
| 2009/0092981 A1 | 4/2009 | Swayze et al. | 435/6 |
| 2010/0081627 A1 | 4/2010 | Sampath et al. | 514/47 |
| 2010/0099750 A1 | 4/2010 | McSwiggen et al. | 514/44 R |
| 2010/0168212 A1 | 7/2010 | Popplewell et al. | 514/44 R |
| 2011/0015253 A1 | 1/2011 | Wilton et al. | 514/44 A |
| 2011/0015258 A1 | 1/2011 | Wilton et al. | 514/44 R |
| 2011/0046203 A1 | 2/2011 | Wilton et al. | 514/44 A |
| 2011/0263686 A1 | 10/2011 | Wilton et al. | 514/44 A |
| 2012/0022144 A1 | 1/2012 | Wilton et al. | 514/44 A |
| 2012/0022145 A1 | 1/2012 | Wilton et al. | 514/44 A |
| 2012/0029057 A1 | 2/2012 | Wilton et al. | 514/44 A |
| 2012/0029058 A1 | 2/2012 | Wilton et al. | 514/44 A |
| 2012/0029059 A1 | 2/2012 | Wilton et al. | 514/44 A |
| 2012/0029060 A1 | 2/2012 | Wilton et al. | 514/44 A |
| 2012/0041050 A1 | 2/2012 | Wilton et al. | 514/44 A |
| 2012/0108652 A1 | 5/2012 | Popplewell et al. | 514/44 A |
| 2013/0116310 A1 | 5/2013 | Wilton et al. | 514/44 A |
| 2013/0217755 A1 | 8/2013 | Wilton et al. | 514/44 A |
| 2013/0253033 A1 | 9/2013 | Wilton et al. | 514/44 A |
| 2013/0253180 A1 | 9/2013 | Wilton et al. | 536/24.5 |
| 2013/0274313 A1 | 10/2013 | Wilton et al. | 514/44 A |
| 2013/0331438 A1 | 12/2013 | Wilton et al. | 514/44 A |

FOREIGN PATENT DOCUMENTS

| | | | |
|---|---|---|---|
| EP | 0614977 | 9/1994 | C12N 15/12 |
| EP | 0438512 | 12/1997 | C12Q 1/68 |
| EP | 0850300 | 7/1998 | C12N 15/11 |
| EP | 1015628 | 7/2000 | C12Q 1/68 |
| EP | 1054058 | 11/2000 | C12N 15/11 |
| EP | 1133993 | 9/2001 | A61K 38/17 |
| EP | 1160318 | 12/2001 | C12N 15/11 |
| EP | 1191097 | 3/2002 | C12N 15/11 |
| EP | 1191098 | 3/2002 | C12N 15/11 |
| EP | 1380644 | 1/2004 | C12N 15/11 |
| EP | 1487493 | 12/2004 | A61K 47/48 |
| EP | 1495769 | 1/2005 | A61K 47/48 |
| EP | 1501931 | 2/2005 | C12N 15/11 |
| EP | 1544297 | 6/2005 | C12N 15/11 |
| EP | 1567667 | 8/2005 | C12Q 1/68 |
| EP | 1568769 | 8/2005 | C12N 15/11 |
| EP | 1619249 | 1/2006 | C12N 15/11 |
| EP | 1857548 | 11/2007 | C12N 15/11 |
| EP | 2119783 | 11/2009 | C12N 15/11 |
| EP | 2135948 | 12/2009 | C12N 15/11 |
| KR | 2003-0035047 | 5/2003 | A61K 48/00 |
| WO | WO 93/01286 | 1/1993 | C12N 15/11 |
| WO | WO 95/16718 | 6/1995 | C08F 255/02 |
| WO | WO 95/30774 | 11/1995 | C12Q 1/68 |
| WO | WO 97/12899 | 4/1997 | C07H 21/04 |
| WO | WO 97/30067 | 8/1997 | C07H 21/04 |
| WO | WO 98/18920 | 5/1998 | C12N 15/12 |
| WO | WO 98/49345 | 11/1998 | C12Q 1/68 |
| WO | WO 98/53804 | 12/1998 | A61K 31/00 |
| WO | WO 00/24885 | 5/2000 | C12N 15/11 |
| WO | WO 01/79283 | 10/2001 | C07K 14/47 |
| WO | WO 01/83503 | 11/2001 | C07H 21/00 |
| WO | WO 01/83695 | 11/2001 | |
| WO | WO 02/24906 | 3/2002 | C12N 15/11 |
| WO | WO 02/26812 | 4/2002 | C07K 14/47 |
| WO | WO 02/29056 | 4/2002 | C12N 15/12 |
| WO | WO 03/002739 | 1/2003 | C12N 15/11 |
| WO | WO 03/013437 | 2/2003 | |
| WO | WO 03/014145 | 2/2003 | C07K 7/00 |
| WO | WO 03/037172 | 5/2003 | |
| WO | WO 03/095647 | 11/2003 | C12N 15/11 |
| WO | WO 2004/011060 | 2/2004 | |
| WO | WO 2004/015106 | 2/2004 | C12N 15/11 |
| WO | WO 2004/016787 | 2/2004 | C12N 15/11 |
| WO | WO 2004/037854 | 5/2004 | C07K 1/04 |
| WO | WO 2004/083432 | 9/2004 | C12N 15/11 |
| WO | WO 2004/083446 | 9/2004 | |
| WO | WO 2004/101787 | 11/2004 | C12N 15/11 |
| WO | WO 2004/108157 | 12/2004 | A61K 39/395 |
| WO | WO 2005/019453 | 3/2005 | C12N 15/11 |
| WO | WO 2005/023836 | 3/2005 | |
| WO | WO 2005/035550 | 4/2005 | |
| WO | WO 2005/085476 | 9/2005 | C12Q 1/68 |
| WO | WO 2005/086768 | 9/2005 | |
| WO | WO 2005/105995 | 11/2005 | C12N 15/11 |
| WO | WO 2005/115439 | 12/2005 | A61K 38/18 |
| WO | WO 2005/115479 | 12/2005 | A61K 48/00 |
| WO | WO 2005/116204 | 12/2005 | C12N 15/09 |
| WO | WO 2006/000057 | 1/2006 | C12N 15/111 |
| WO | WO 2006/007910 | 1/2006 | A61K 31/56 |
| WO | WO 2006/017522 | 2/2006 | A61K 48/00 |

(56) References Cited

FOREIGN PATENT DOCUMENTS

| | | | |
|---|---|---|---|
| WO | WO 2006/031267 | 3/2006 | ............ C12N 15/11 |
| WO | WO 2006/054262 | 5/2006 | |
| WO | WO 2006/083800 | 8/2006 | |
| WO | WO 2006/108052 | 10/2006 | ............ A61K 47/48 |
| WO | WO 2006/112705 | 10/2006 | ......... A61K 31/7088 |
| WO | WO 2006/121960 | 11/2006 | ............ C12N 15/11 |
| WO | WO 2007/002904 | 1/2007 | ............ C12Q 1/68 |
| WO | WO 2007/004979 | 1/2007 | ............ A61K 38/00 |
| WO | WO 2007/044362 | 4/2007 | ............ A61K 48/00 |
| WO | WO 2007/089584 | 8/2007 | ............ A61K 48/00 |
| WO | WO 2007/089611 | 8/2007 | ............ C12N 15/11 |
| WO | WO 2007/135105 | 11/2007 | ............ C12N 15/11 |
| WO | WO 2008/011170 | 1/2008 | ............ C12Q 1/68 |
| WO | WO 2008/018795 | 2/2008 | ............ C12N 15/11 |
| WO | WO 2008/021136 | 2/2008 | ........... A01K 67/027 |
| WO | WO 2008/043561 | 4/2008 | ............ A01K 48/00 |
| WO | WO 2008/103060 | 8/2008 | ............ C12N 15/11 |
| WO | WO 2009/005793 | 1/2009 | ............ A61K 48/00 |
| WO | WO 2009/008727 | 1/2009 | ............ A61K 47/48 |
| WO | WO 2009/015384 | 1/2009 | ............ A61K 38/00 |
| WO | WO 2009/054725 | 4/2009 | ............ A61K 31/56 |
| WO | WO 2009/099326 | 8/2009 | ............ A61K 48/00 |
| WO | WO 2009/101399 | 8/2009 | ........... A61K 31/712 |
| WO | WO 2009/120887 | 10/2009 | ............ A61K 47/48 |
| WO | WO 2009/135322 | 11/2009 | ............... C12Q 1/68 |
| WO | WO 2009/139630 | 11/2009 | ............ C12N 15/11 |
| WO | WO 2009/144481 | 12/2009 | |
| WO | WO 2009/151600 | 12/2009 | ............ C12N 15/12 |
| WO | WO 2011/057350 | 5/2011 | ........... C12N 15/113 |

OTHER PUBLICATIONS

Jensen et al., "Expression of alternatively spliced interleukin-1 receptor accessory protein mRNAs is differentially regulated during inflammation and apoptosis," Cellular Signalling (2003), 15:793-802.

Nakamura et al., "Exon-skipping therapy for Duchenne muscular dystrophy", Neuropathology (2009), 29:494-501.

Smeets et al., "Effectiveness of the Soluble Form of the Interleukin-1 Receptor Accessory Protein as an Inhibitor of Interleukin-1 in Collagen-Induced Arthritis," Arthritis & Rheumatism (2003), 48(10):2949-2958.

Smeets et al., "Soluble Interleukin-1 Receptor Accessory Protein Ameliorates Collagen-Induced Arthritis by a Different Mode of Action From That of Interleukin-1 Receptor Antagonist," Arthritis & Rheumatism (2005), 52(7):2002-2211.

Smith et al., "The Soluble Form of IL-1 Receptor Accessory Protein Enhances the Ability of Soluble Type II IL-1 Receptor to Inhibit IL-1 Action," Immunity (2003), 18:87-96.

Aartsma-Rus et al., Guidelines for antisense oligonucleotide design and insight into splice-modulating mechanisms, Molecular Therapy, vol. 17, No. 3, pp. 548-553, Mar. 2009.

Aartsma-Rus et al., Exploring the frontiers of therapeutic exon skipping for Duchenne Muscular Dystrophy by double targeting within one or multiple exons, Molecular Therapy, 14(3): 401-407, Sep. 2006.

Aartsma-Rus et al., Functional Analysis of 114 Exon-Internal AONs for Targeted DMD Exon Skipping: Indication for Steric Hindrance of SR Protein Binding Sites, Oligonucleotides, 15: 284-297, 2005.

Aartsma-Rus et al., Antisense Mediated exon skipping; A Versatile Tool with Therapeutic and Research Applications, RNA, 13(10):1609-1624, 2007.

Aartsma-Rus et al., Antisense-Induced Exon Skipping for Duplications in Duchenne Muscular Dystrophy, BMC Med. Genet. 8:43, 9 pages, Jul. 5, 2007.

Aartsma-Rus et al., Therapeutic Modulation of DMD splicing by Blocking Exonic Splicing Enhancer Sites with Antisense Oligonucleotides Ann NY Acad Sci, 1082, pp. 74-76, 2006.

Aartsma-Rus et al., Antisense-Induced Multiexon Skipping for Duchenne Muscular Dystrophy Makes More Sense, Am. J. Hum. Genet, 74: 83-92, 2004.

Aartsma-Rus et al., Targeted exon skipping as a potential gene correction therapy for Duchenne muscular dystrophy, Neuromuscular Disorders, 12: S71-S77, 2002.

Aartsma-Rus et al., Therapeutic antisense-induced exon skipping in cultured muscle cells from six different DMD patients, Human Molecular Genetics, 12(8): 907-14, 2003.

Aartsma-Rus et al., Comparative analysis of antisense oligonucleotide analogs for targeted DMD exon 46 skipping in muscle cells, Gene Therapy, 11: 1391-1398, 2004.

Aartsma-Rus et al., Theoretic Applicability of Antisense-Mediated Exon Skipping for Duchenne Muscular Dystrophy Mutations, Human Mutation, 30(3): 293-299, 2009.

Abbs et al., A convenient multiplex PCR system for the detection of dystrophin gene deletions: a comparative analysis with cDNA hybridisation shows mistypings by both methods, J. Med. Genet, 28:304-311, 1991.

Agrawal et al., Antisense therapeutics: is it as simple as complementary base recognition? Mol. Med. Today, 6:72-81, Feb. 2000.

Alter et al., Systemic delivery of morpholino oligonucleotide restores dystrophin expression bodywide and improves dystrophic pathology. Nature Medicine, 12(2):175-177, Feb. 2006; Epub Jan. 26, 2006.

Amalfitano et al., Structure and mutation of the dystrophin gene, In: Dystrophin: Gene, protein and cell biology, (Brown and Lucy, eds). Cambridge University Press, pp. 1-16,1997.

Anderson et al., Correlated NOS-I[mu] and myf5 expression by satellite cells in mdx mouse muscle regeneration during NOS manipulation and deflazacort treatment, Neuromusccular Disorders, 13(5): 388-396, Jan. 2003.

Arap, Steps toward mapping the human vasculature by phage display, Nature Medicine, 8(2):121-127, Feb. 2002.

Arechavala-Gomeza et al., Comparative Analysis of Antisense Oligonucleotide Sequences for Targeted Skipping of Exon 51 During Dystrophin pre-mRNA Splicing in Human Muscle, Hum Gene Ther 18(9):798-810, Sep. 2007.

Arruda, The role of immunosuppression in gene and cell based treatments for Duchenne Muscular Dystrophy, Molecular Therapy, 15(6): 1040-1041, Jun. 2007.

Arzumanov et al., Inhibition of HIV-1 Tat-dependent trans activation by steric block chimeric 2'-O-methyl/LNA oligoribonucleotides. Biochemistry, 40(48): 14645-14654, 2001.

Austin et al., Cloning and characterization of alternatively spliced isoforms of Dp71, Human Molecular Genetics 4(9): 1475-1483, 1995.

Austin et al., Expression and synthesis of alternatively spliced variants of Dp71 in adult human brain, Neuromuscular Disorders,10:187-193, 2000.

Barabino et al., Antisense probes targeted to an internal domain in U2 snRNP specifically inhibit the second step of pre-mRNA splicing, Nucleic Acids Research, 20(17): 4457-4464, 1992.

Barany, The ligase chain reaction in a PCR world, PCR Methods and Applications, 1(1): Aug. 5-16, 1991.

Beggs et al., Detection of 98% of DMD/BMD gene deletions by polymerase chain reaction, Human Genetics, 86: 45-48, 1990.

Bremmer-Bout, et al., Targeted exon skipping in transgenic hDMD mice: A model for direct preclinical screening of human-specific antisense oligonucleotides, Molecular Therapy, 10(2): 232-240, Aug. 2004.

Brett et al., EST comparison indicates 38% of human mRNAs contain possible alternative splice forms, FEBS Letters, 474(1): 83-86, 2000.

Brown et al., Gene delivery with synthetic (non viral) carriers., Int. J. Pharm., vol. 229, Nos. 1-2, pp. 1-21, Oct. 23, 2001 (Abstract).

Buck et al., Design Strategies and Performance of Custom DNA Sequencing Primers, BioTechniques, 27(3): 528-536, Sep. 1999.

Burnett et al., DNA sequence-specific polyamides alleviate transcription inhibition associated with long GAA-TTC repeats in Friedreich's ataxia, PNAS, 103(31): 11497-11502, Aug. 2006.

Caplen, et al., Rescue of polyglutamine-mediated cytotoxicity by double-stranded RNA-mediated RNA interference, Human Molecular Genetics, 11(2): 175-184, 2002.

Cartegni, et al., Listening to silence and understanding nonsense: exonic mutations that affect splicing, Nature Reviews Genetics, 3: 285-298, Apr. 2002.

(56) References Cited

OTHER PUBLICATIONS

Chaubourt et al., Muscular nitric oxide synthase ([mu]NOS) and utrophin, *J. Physiology Paris*, 96(1-2): 43-52, Jan.-Mar. 2002.

Coulter et al., Identification of a new class of exonic splicing enhancers by in vivo selection, *Mol. Cell. Biol.* 17(4) 2143-2150, Apr. 1997.

Basic Principles of Antisense Therapeutics, Antisense Research and Application, Handbook of Experimental Pharmacology, 131: 1-50, 1998.

Dahlqvist et al., Functional notch signaling is required for BMP4-induced inhibition of myogenic differentiation, *Development* 130: 6089-6099, Aug. 2003.

De Angelis et al., Chimeric snRNA molecules carrying antisense sequences against the splice junctions of exon 51 of the dystrophin pre-mRNA exon skipping and restoration of a dystrophin synthesis in delta 48-50 DMD cells, *PNAS*, 99(14): 9456-9461, Jul. 9, 2002.

Denny et al., Oligo-riboprobes, Tools for in situ hybridization. *Histochemistry* 89:481-493, 1988.

Dickson et al., Screening for antisense modulation of dystropin pre-mRNA splicing, *Neuromuscul. Disord.*, Supp. 1, S67-S70, 2002.

Dirksen et al., Mapping the SF2/ASF Binding Sites in the Bovine Growth Hormone Exonic Splicing Enhancer, *J. Biological Chemistry*, 275(37): 29170-29177, Sep. 15, 2000.

Dorchies et al., Green tea extract and its major polyphenol (−)-epigallocatechin gallate improve muscle function in a mouse model for Duchenne muscular dystrophy, *Am .J. Cell Physiological*, 290: C616-C625, 2006.

Duboc et al., Effect of Perindopril on the Onset and Progression of Left Ventricular Dysfunction in Duchenne Muscular Dystrophy, *J. Amer. Coll. Cardiology*, 45(6): 855-857, Mar. 15, 2005.

Dubowitz, Foreword, *Neuromuscular Disorders*, 12: S1-S2, 2002.

Dubowitz, Special Centennial Workshop, 101$^{st}$ ENMC International Workshop: Therapeutic Possibilities in Duchenne Muscular Dystrophy, Nov. 30-Dec. 2, 2001, Naarden, The Netherlands, *Neuromuscular Disorders*, 12: 421-431, 2002.

Dunckley et al., Modulation of Splicing in the DMD Gene by Antisense Oligoribonucleotides, *Nucleosides & Nucleotides*, 16 (7-9):1665-1668, 1997.

Dunckley et al., Modification of splicing in the Dsytrophin gene in cultured Mdx muscle cells by antisense oligoribonucleotides, *Human Molecular Genetics*, 7(7):1083-1090, 1995.

El-Andaloussi et al., Abstract: Induction of splice correction by cell-penetrating peptide nucleic acids., *J. Gene Med.*, 8(10):1262-1273, Oct. 2006.

Erba et al., Structure, chromosome location, and expression of the human gamma-actin gene: differential evolution, location, and expression of the cytoskeletal beta- and gamma-actin genes, *Mol. Cell. Biology*, 8(4): 1775-1789, Apr. 1988.

Errington et al., Target selection for antisense oligonucleotide induced exon skipping in the dystrophin gene. *J Gene Med*, 5(6):518-527, 2003.

Fainsod et al., The dorsalizing and neural inducing gene *follistatin* in an antagonist of *BMP-4, Mechanisms of Development*, 63: 39-50,1997.

Feener et al., Alternative splicing of human dystrophin mRNA generates isoforms at the carboxy terminus, *Nature*, 338: 509-511, Apr. 6, 1989.

Fluiter, K., In Vivo tumor growth inhibition and biodistribution studies of locked nucleic acid (LNA) antisense oligonucleotides, *Nucl. Acids Research*, 31(3): 953-962, 2003.

Fu et al., An Unstable Triplet Repeat in a Gene Related to Myotonic Muscular Dystrophy *Science*, 255: 1256-1258, 1992.

Furling et al., Viral vector producing antisense RNA restores myotonic dystrophy myoblast functions, *Gene Therapy*, 10: 795-802, 2003.

Galderisi et al., Myotonic dystrophy: antisense oligonucleotide inhibition of DMPK gene expression in vitro, *Biochem Biophys Res Commun* 221: 750-754, 1996.

Galderisi et al., Antisense Oligonucleotides as Therapeutic Agents, *Journal of Cellular Physiology*, 181: 251-257, 1999.

Garcia-Blanco et al., Alternative splicing in disease and therapy, *Nature Biotechnology*, 22(5): 535-546, May 2004.

Ginjaar et al., Dystrophin nonsense mutation induces different levels of exon 29 skipping and leads to variable phenotypes within one BMD family, *European J. Human Genetics* 8: 793-796, 2000.

Gollins et al., High-efficiency plasmid gene transfer into dystrophic muscle, *Gene Therapy*, 10: 504-512, 2003.

Grady, Promising Dystrophy Drug Clears Early Test, *The New York Times*, 3 pages, Dec. 27, 2007.

Grady, "Early drug test shows promise in treating muscular dystrophy", Health & Science, International Hearld Tribune, Jan. 3, 2008, p. 9.

Granchelli et al., Pre-clinical screening of drugs using the mdx mouse, *Neuromuscular Disorders*, 10(4-5): 235-239, 2000.

Gryaznov, Oligonucleotide N3'→ P5' phosphoramidates as potential therapeutic agents, *Biochem Biophys. Acta*, 1489: 131-140, 1999.

Hagiwara et al., A novel point mutation ($G^{-1}$ to T) in a 5' splice donor site of intron 13 of the dystrophin gene results in exon skipping and is responsible for Becker muscular dystrophy, *Am J. Hum Genet.*, 54(1): 53-61, 1994.

Handa et al., The AUUCU repeats responsible for spinocerebellar ataxia type 10 form unusual RNA hairpins, *J. Biological Chemistry*, 280(32): 29340-29345, Aug. 12, 2005.

Harding et al., The Influence of Antisense Oligonucleotide Length on Dystrophin Exon Skipping, *Molecular Therapy*, 15(1): 157-166, Jan. 2007.

Hasholt et al., Antisense downregulation of mutant huntingtin in a cell model, *J. Gene Medicine*, 5: 528-538, 2003.

Heemskerk et al., "In vivo comparison of 2'-O-methyl phosphorothioate and Morpholino antisense oligonucleotides for Duchenne muscular dystrophy exon skipping", The Journal of Gene Medicine, vol. 11, pp. 257-266, 2009.

Heemskerk et al., Development of Antisense-Mediated Exon Skipping as a Treatment for Duchenne Muscular Dystrophy, *Ann. NY Acad. Sci.*, 1175: 71-79, 2009.

Highfield, Science: Boffin log, The Daily Telegraph, http://www.telegraph.co.uk/science/science-news/3320286/Science-Boffin-log.html, (Hope for Muscular Dystrophy Drug) Jan. 1, 2008, 5 pages.

Hoffman, Skipping toward Personalized Molecular Medicine, *N. Eng. J. Med.*,357(26): 2719-2722, Dec. 27, 2007.

Hoffman et al., Somatic reversion/suppression of the mouse *mdx* phenotype in vivo, *J. Neurological Sciences*, 99: 9-25, 1990.

Hussey et al., Analysis of five Duchenne muscular dystrophy exons and gender determination using conventional duplex polymerase chain reaction on single cells, *Molecular Human Reproduction*, 5(11): 1089-1094, 1999.

Iezzi et al., Decetylase inhibitors increase muscle cell size by promoting myoblast recruitment and fusion through induction of follistatin, *Development Cell*, 6: 673-684, May 2004.

Ikezawa et al., Dystrophin gene analysis on 130 patients with Duchenne Muscular dystrophy with a special reference to muscle mRNA analysis, *Brain & Develop.*, 20: 165-168, 1998.

Ito et al., Purine-Rich Exon Sequences Are Not Necessarily Splicing Enhancer Sequence in the Dystrophin Gene, *Kobe J. Med. Sci.*, 47: 193-202, Oct. 4, 2001.

Karras et al., Deletion of Individual Exons and Induction of Soluble Murine Interleukin-5 Receptor-alpha Chain Expression through Antisense Oligonucleotide-Mediated Redirection of Pre-mRNA Splicing, *Molecular Pharmacology*,58: 380-387, 2000.

Kerr et al., Bmp Regulates Skeletal Myogenesis at Two Steps, Molecular Cellular Proteomics 2.9: 976. 123.8, 2003 (Abstract Only).

Kinali et al., Local Restoration of Dystrophin Expression With the Morpholino Oligomer AVI-4658 in Duchenne Muscular Dystrophy: A Single-blind, Placebo-Controlled Dose-Escalation, Proof-of Concept Study, *Lancet Neurol.*, 8: 918-928, Aug. 26, 2009.

Kurrek et al., Design of antisense oligonucleotides stabilized by locked nucleic acids, *Nucleic Acids Research*, 30(9): 1911-1918, 2002.

Langlois et al., Hammerhead ribozyme-mediated destruction of nuclear foci in myotonic dystrophy myoblasts, *Molecular Therapy*, 7(5): 670-680, May 2003.

(56) References Cited

OTHER PUBLICATIONS

Laptev et al., Specific inhibition of expression of a human collagen gene (COL1A1) with modified antisense oligonucleotides. The most effective target sites are clustered in double-stranded regions of the predicted secondary structure for the mRNA *Biochemistry*, 33(36): 11033-11039, 1994.

Lee et al., Receptor mediated uptake of peptides that bind the human transferrin receptor, *Eur. J. Biochem.*, 268: 2004-2012, 2001.

Liu et al., A mechanism for exon skipping caused by nonsense or missense mutations in BRCA1 and other genes, *Nature Genetics*, 27(1):55-58, Jan. 2001.

Liu et al., Specific inhibition of Huntington's disease gene expression by siRNAs in cultured cells, *Proc. Japan Acad.*, 79,Ser. B: 293-298, 2003.

Liu et al., Identification of functional exonic splicing enhancer motifs recognized by individual SR proteins, *Genes & Development*, 12:1998-2012, 1998.

Lu et al., Functional Amounts of Dystrophin Produced by Skipping the Mutated Exon in the mdx Dystrophic Mouse *Nature Medicine*, 9(8): 1009-1014, Aug. 2003.

Lu et al., Massive Idiosyncratic Exon Skipping Corrects the Nonsense Mutation in Dystrophic Mouse Muscle and Produces Functional Revertant Fibers by Clonal Expansion, *The Journal of Cell Biology*, 148(5): 985-995, Mar. 6, 2000.

Lu et al., Non-viral gene delivery in skeletal muscle: a protein factory, *Gene Therapy*, 10:131-142, 2003.

Lu et al., Systemic delivery of antisense oligoribonucleotide restores dystrophin expression in body-wide skeletal muscles, *PNAS*, 102(1): 198-203, Jan. 4, 2005.

Mann et al., Antisense-induced exon skipping and synthesis of dystrophin in the mdx mouse, *PNAS*, 98(1): 42-47, Jan. 2, 2001.

Mann et al., Improved antisense oligonucleotide induced exon skipping in the mdx mouse model of muscular dystrophy, *J Gene Med.*, 4(6): 644-654, 2002.

Martiniuk et al., Correction of glycogen storage disease type II by enzyme replacement with a recombinant human acid maltase produced by over-expression in a CHO-DHFR(neg) cell line, *Biochem. Biophys. Res. Commun.*, 276( 3): 917-923, Oct. 5, 2000 (Abstract).

Matsuo et al., Partial deletion of a dystrophin gene leads to exon skipping and to loss of an intra-exon hairpin structure from the predicted mRNA precursor, *Biochem. Biophys. Res. Commun.*, 182(2): 495-500, Jan. 31, 1992.

Matsuo, Duchenne/ Becker muscular dystrophy: from molecular diagnosis to gene therapy, *Brain and Development*, 18(3): 167-172, 1996.

Matsuo et al., Exon Skipping during Splicing of Dystrophin mRNA Precursor due to an Intraexon Deletion in the Dystrophin Gene of Duchenne Muscular Dystrophy Kobe, *J. Clin. Invest.*, 87: 2127-2131, Jun. 1991.

Matsuo, Duchenne and Becker Muscular Dystrophy: From Gene Diagnosis to Molecular Therapy, IUBMB Life, 53: 147152, 2002.

Matteucci, Structural modifications toward improved antisense oligonucleotides, *Perspectives in Drug Discovery and Design*, 4: 1-16, 1996.

McClorey et al., Induced Dystrophin Exon Skipping in Human Muscle Explants, Neuromuscul Disorders,16: 583-590, 2006.

Miller et al., Antisense oligonucleotides: strategies for delivery, *PSTT*, 9(1): 377-386, Dec. 1998.

Monaco et al., An Explanation for the Phenotypic Differences between Patients Bearing Partial Deletions of the DMD Locus, Genomics, 2: 90-95, 1988.

Moon et al., Target site Search and effective inhibition of leukaemic cell growth by a covalently closed multiple anti-sense oligonucleotide to c-myb, *Biochemical Journal*, 346: 295-303, 2000.

Munroe, Antisense RNA inhibits splicing of pre-mRNA in vitro, The EMBO Journal, 7(8): 2523-2532, 1988.

Muntoni et al., A Mutation in the Dystrophin Gene Selectively Affecting Dystrophin Expression in the Heart. *J. Clin Invest.*, 96: 693-699, Aug. 1995.

Muntoni et al., 149th ENMC International Workshop and 1st TREAT-NMD Workshop on: Planning Phase I/II Clinical trials using Systemically Delivered Antisense Oligonucleotides in Duchenne Muscular Dystrophy, *Neuromuscular Disorders*, 18: 268-275, 2008.

Nakamura, "Exon-skipping therapy for Duchenne muscular dystrophy", Neuropathology, vol. 29, pp. 494-501, 2009.

Nishio, et al., Identification of a novel first exon in the human dystrophin gene and of a new promoter located more than 500 kb upstream of the nearest known promoter. *J. Clin. Investigation*, 94: 1037-1042, Sep. 1994.

Opalinska et al., Nucleic-acid therapeutics: basic principles and recent applications, *Nature Reviews Drug Discovery*, 1:503-514, Jul. 2002.

O'Shaughnessy et al., Superior Survival With Capecitabine Plus Docetaxel Combination Therapy in Anthracycline-Pretreated Patients With Advanced Breast Cancer: Phase III Trial Results, *J. Clinical Oncology*, 20(12): 2812-2823, Jun. 15, 2002.

Patel et al., The Function of Myostatin and strategies of Myostatin blockade—new hope for therapies aimed at promoting growth of skeletal muscle, *Neuromuscular Disorders* ,15(2): 117-126, 2005.

Phillips, Antisense Inhibition and Adeno-Associated Viral Vector Delivery for Reducing Hypertension, *Hypertension*, 29(1), Part 2: 177-187, Jan. 1997.

Politano et al., Gentamicin administration in Duchenne patients with premature stop codon. *Acta Myologica* 22(1):15-21, 2003.

Popplewell et al., Design of Phosphorodiamidate Morpholino Oligomers (PMOs) for the Induction of Exon Skipping of the Human DMD Gene, *Mol. Therap.* 17(3): 554-561, Mar. 2009.

Pramono et al., Induction of Exon Skipping of the Dystrophin Transcript in Lymphoblastoid Cells by Transfecting an Antisense Oligodeoxynucleotide Complementary to an Exon Recognition Sequence, *BBRC*, 226:445-449, 1996.

Radley et al., Duchenne muscular dystrophy: Focus on pharmaceutical and nutritional interventions, *International J. Biochem. and Cell Biol.*, 39(3): 469-477, Oct. 2006.

Rando, Thomas A., Oligonucleotide-mediated gene therapy for muscular dystrophies, *Neuromuscular Disorders*, 12: S55-S60, 2002.

Reitter B., Deflazacort vs. prednisone in Duchenne muscular dystrophy: trends of an ongoing study, *Brain & Dev.*, 17 Suppl: 39-43, 1995.

Reuser et al., Uptake and Stability of Human and Bovine Acid α-Glucosidase in Cultured Fibroblasts and Skeletal Muscle Cells from Glycogenosis Type II Patients, *Experimental Cell Research*, 155: 178-189, 1984.

Roberts et al., Direct detection of dystrophin gene rearrangements by analysis of dystrophin mRNA in peripheral blood lymphocytes, *Am. J. Hum. Genet.*, 49(2): 298-310, 1991.

Roberts et al., Exon structure of the human dystrophin gene, *Genomics*, 1993, 16(2): 536-538, 1993.

Roberts et al., Direct diagnosis of carriers of Duchenne and Becker muscular dystrophy by amplification of lymphocyte RNA, *Lancet*, 336: 1523-1526, 1990.

Roberts et al., Searching for the 1 in 2,400,000: a review of dystrophin gene point mutations, *Human Mutation*, 4: 1-11, 1994.

Rolland et al., Overactivity of exercise-sensitive cation channels and their impaired modulation by IGF-1 in mdx native muscle fibers: beneficial effect of pentoxifylline. *Neurobiology of Disease*, 24(3): 466-474, 2006.

Rosen et al., Combination Chemotherapy and Radiation Therapy in the Treatment of Metastatic Osteogenic Sarcoma, *Cancer* 35: 622-630, 1975.

Samoylova et al., Elucidation of muscle-binding peptides by phage display screening, *Muscle & Nerve*,22: 460-466, Apr. 1999.

Sarepta Therapeutics, Inc., Sarepta Therapeutics and University of Western Australia Announce Exclusive Worldwide Licensing Agreement for Exon-Skipping Program in Duchenne Muscular Dystrophy, *News Release*, EP1619249, 3 pages, Nov. 4, 2013.

Scanlon, Anti-genes: siRNA, ribozymes, and antisense, *Curr. Pharmaceutical Biotechnology*, 5: 415-420, 2004.

Segalat et al., CAPON expression in skeletal muscle is regulated by position, repair, NOS activity, and dystrophy, *Exp. Cell Research*, 302(2): 170-179, 2005.

(56) References Cited

OTHER PUBLICATIONS

Sertic et al., Deletion screening of Duchenne/Becker muscular dystrophy gene in Croatian population, *Coll. Antropol.*, 1:151-156, 1997.
Shapiro and Senapathy, RNA splice junctions of different classes of eukaryotes: sequence statistics and functional implications in gene expression. *Nucleic Acids Research*, 15(17): 7155-7174, 1987.
Sherratt et al., Exon Skipping and Translation in Patients with Frameshift Deletions in the Dystrophin Gene, *Am. J. Hum. Genet*, 53:1007-1015, 1993.
Shiga et al., Disruption of the Splicing Enhancer Sequence within Exon 27 of the Dystrophin Gene by a Nonsense Mutation Induces Partial Skipping of the Exon and Is Responsible for Becker Muscular Dystrophy, *J. Clin. Invest.*, 100(9): 2204-10, Nov. 1997.
Simoes-Wust et al., bcl-xL Antisense Treatment Induces Apoptosis in Breast Carcinoma Cells, *Int. J. Cancer*,87: 582-590, 2000.
Smith et al., Muscle-specific peptide #5, Mar. 23, 1999. From http://www.ebi.ac.uk/cgi-bin/epo/epofetch?AAW89659, downloaded Jul. 16, 2007. XP 002442550.
Spitali et al., "Exon Skipping-Medicated Dystrophin Reading Frame Restoration for Small Mutations", Human Mutation, vol. 30, No. 11, pp. 1527-1534 , Nov. 2009.
Sterrenburg et al., Gene expression of profiling highlights defective myogenesis in DMD patients and a possible role for bone morphogenetic protein 4, *Neurobiology of Disease*, 23(1): 228-236, 2006.
Summerton et al., Morpholino Antisense Oligomers: Design, Preparation, and Properties, *Antisense & Nucleic Acid Drug Development*, 7: 187-195, 1997.
Surono et al., Chimeric RNA/ethylene-Bridged Nucleic Acids Promote Dystrophin Expression in Myocytes of Duchenne Muscular Dystrophy by Inducing Skipping of the Nonsense Mutation-Encoding Exon, *Human Gene Therapy*, 15:749-757, Aug. 2004.
Surono et al., Six Novel Transcripts that Remove a Huge Intron Ranging from 250 to 800 kb Are Produced by Alternative Splicing of the 5' Region of the Dystrophin Gene in Human Skeletal Muscle, *BBRC*, 239:895-899, 1997.
Suter et al., Double-target antisense U7 snRNAs promote efficient skipping of an aberrant exon in three human B-thalassemic mutations, *Human Molecular Genetics*, 8(13): 2415-2423, 1999.
Suwanmanee et al., Restoration of Human β-Globin Gene Expression in Murine and Human IVS2-654 Thalassemic Erythroid Cells by Free Uptake of Antisense Oligonucleotides, *Mol. Pharmacology* 62(3):545-553, 2002.
Takashima et al., Oligonucleotides Against a Splicing Enhancer Sequence Led to Dystrophin Production in Muscle Cells From a Duchenne Muscular Dystrophy Patient, *Brain & Development*, 23: 788-790, 2001.
Takeshima et al., Intravenous Infusion of an Antisense Oligonucleotide Results in Exon Skipping in Muscle Dystrophin mRNA of Duchenne Muscular Dystrophy. *Pediatric Res*, 59(5):690-694, 2006.
Takeshima et al., Expression of Dystrophin Protein in Cultured Duchene Muscular Dystrophy Cells by Exon Skipping Induced by Antisense Oligonucleotide, (Abstract); *Abstract of the Japan Society of Human Genetics General Meeting Program*, 8 pages, Nov. 17-19, 1999.
Takeshima et al., Modulation of In Vitro Splicing of the Upstream Intron by Modifying an Intra-Exon Sequence Which is Deleted from the Dystrophin Gene in Dystrophin Kobe, *J. Clin. Invest.*, 95:515-520, Feb. 1995.
Takeshima et al., "Basic research for treatment of Duchene muscular dystrophy using induction of exon skipping by means of antisense oligo DNA: effect of in vivo administration in mice," Park IP Translations, vol. 15, No. 2, 6 pages, Nov. 2009.
Tanaka et al., Polypurine Sequences within a Downstream Exon Function as a Splicing Enhancer, *Molecular and Cellular Biology*, 14(2):1347-1354, Feb. 1994.
Thanh et al., Characterization of revertant muscle fibers in Duchenne muscular dystrophy, using exon-specific monoclonal antibodies against dystrophin, *Am. J. Hum. Genet.* 56:725-731, 1995.
Tian and Kole, Selection of novel exon recognition elements from a pool of random sequences, *Mol Cell Biol*, 15(11): 6291-6298, Nov. 1995.
Tsuchida, Peptides, Proteins & Antisense: the role of myostatin and bone morphogenetic proteins in muscular disorders, *Expert Opinion of Biologica Therapy*, 6(2):147-153, 2006.
Van Deutekom et al., Advances in Duchenne Muscular Dystrophy Gene Therapy *Nat Rev Genet*, 4(10): 774-783, Oct. 2003.
Van Deutekom et al., Antisense-induced exon skipping restores dystrophin expression in DMD patient derived muscle cells, *Hum Mol Genet.*, 10(15): 1547-1554, 2001.
Van Deutekom et al., Local Dystrophin Restoration with Antisense Oligonucleotide PRO051, *N. England J. Med.*, 357: 2677-2686, 2007.
Van Ommen, The Therapeutic Potential of Antisense-Mediated Exon-Skipping, *Curr Opin Mol. Ther* ,10(2) 140-149, 2008.
Van Vliet, et al., Assessment of the feasibility of exon 45-55 multiexon skipping for duchenne muscular dystrophy, *BMC Medical Genetics*, 9:105 (7 pages), 2008.
Varani et al., The G•U wobble base pair, *EMBO Reports*, 1(1): 18-23, 2000.
Verreault, et al., GENE silencing in the development of personalized cancer treatment: the targets, the agents and the delivery systems, *Curr. Gene Therapy*, 6: 505-553, 2006.
Vickers, et al., Efficient reduction of target RNAs by small interfering RNA and RNase H-dependent antisense agents, A comparative analysis, *J. Biol. Chem.*, 278(9): 7108-7118, 2003.
Wang et al., Adeno-associated virus vector carrying human minidystrophin genes effectively ameliorates muscular dystrophy in mdx mouse model, PNAS, 97(25):13714-13719, Dec. 5, 2000.
Watakabe et al., The role of exon sequences in splice site selection, Genes & Development, 7: 407-418, 1993.
Weiler et al., Identical mutation in patients with limb girdle muscular dystrophy type 2B or Miyoshi myopathy suggests a role for modifier gene(s), *Human Molecular Genetics*, 8(5): 871-877, 1999.
Weisbart et al., Cell type specific targeted intracellular delivery into muscle of a monoclonal antibody that binds myosin llb., *Molecular Immunology*, 39(13): 783-789, Mar. 2003 (Abstract).
Wells et al., Enhanced in Vivo Delivery of Antisense Oligonucleotide to Restore Dystrophin Expression in Adult MDX Mouse Muscle, FEBS Letters, 552: 145-149, 2003.
Wheway and Roberts, The Dystrophin Lymphocyte promoter revisited: 4.5-megabase intron, or artefact? *Neuromuscular Disorders*,13:17-20, 2003.
Wilton et al., Antisense oligonucleotides, exon skipping and the dysrophin gene transcript, *Acta Myologica*, XXIV:222-229, 2005.
Wilton et al., Specific removal of the nonsense mutation from the mdx dystrophin protein mRNA using antisense oligonucleotides. Neuromuscular Disorders, 9: 330-338, 1999.
Wilton et al., Antisense oligonucleotide-induced exon skipping across the human dystrophin gene transcript, Mol Ther,15(7):1288-1296, Jul. 2007.
Yen et al., Sequence-Specific Cleavage of Huntingtin mRNA by Catalytic DNA, *Annals of Neurology*, 46(3): 366-373, Sep. 1999.
Yin et al., "Effective Exon Skipping and Restoration of Dystrophin Expression by Peptide Nucleic Acid Antisense Oligonucleotides in mdx Mice", The American Society of Gene Therapy, vol. 16, No. 1, pp. 38-45, Jan. 2008.
Yokota et al., "Efficacy of Systemic Morpholino Exon-Skipping in Duchenne Dystrophy Dogs", American Neurological Association, pp. 667-676, 2009.
Yu et al., A hairpin ribozyme inhibits expression of diverse strains of human immunodeficiency virus type 1, *Proc. Natl. Acad. Sci. USA*, 90: 6340-6344, Jul. 1993.
Zhang et al., Efficient expression of naked dna delivered intraarterially to limb muscles of nonhuman primates., *Hum. Gene. Ther.*, 12(4): 427-438, Mar. 1, 2001 (Abstract).
Zhou et al., Current understanding of dystrophin-related muscular dystrophy and therapeutic challenges ahead, *Chinese Medical Journal*, 119(16): 1381-1391, 2006.

(56) References Cited

OTHER PUBLICATIONS

Bionity, Bionity.Com NEWS-Center, Leiden University Medical Center and Prosensa B.V. Announce First Successful Clinical Study with RNA-based Therapeutic PRO051, dated Jan. 3, 2008, http://www.bionity.com/news/e/76185.

Biopharmaceutiques, Biopharmaceutiques, Merging Pharma & Biotech, Edition 48, Jan. 10, 2008, http://www.biopharmaceutiques.com/en/num, visited Jan. 11, 2008.

TREAT-NMD Neuromuscular Network, TREAT-NMD Neuromuscular Network, Newsletter No. 24, Jan. 11, 2008, 6 pages.

\* cited by examiner

US 8,802,645 B2

MOLECULE FOR TREATING AN INFLAMMATORY DISORDER

CROSS-REFERENCE TO RELATED APPLICATIONS

This application is a Continuation of PCT International Application Ser. No. PCT/NL2010/050882, filed Dec. 22, 2010, designating the United States, which claims the benefit of European Application No. 09180760.2, filed on Dec. 24, 2009 and U.S. Provisional Application No. 61/290,102, filed on Dec. 24, 2009. The entire contents of the aforementioned patent applications are incorporated herein by this reference.

FIELD OF THE INVENTION

The invention provides two types of oligonucleotides for treating an inflammatory disorder: a molecule which is able of altering the splicing of a pre-mRNA encoding a C5 in order to decrease the amount of a C5a and a molecule which is able of altering the splicing of a pre-mRNA encoding a IL-1RAcP in order to increase the amount of a soluble IL-1RAcP. The invention further provides the use of said molecules for preventing or treating an inflammatory disorder.

BACKGROUND OF THE INVENTION

In a number of inflammatory diseases, including rheumatoid arthritis (RA) and dermatitis, there is excessive and inappropriate complement activation as well as an excessive concentration of IL-1 in the plasma.

Complement system is part of the innate immune system, acting to protect the host from microorganisms such as bacteria, and other foreign and abnormal cells (e.g. apoptotic cells). However, primarily protective, complement activation can also cause damage to the host. C5, the fifth component of the complement system is a glycoprotein consisting of 1679 amino acids in two disulfide-linked polypeptide chains, C5α and C5β (2). After activation by the C5 convertase, which is activated by immune complexes (IC), C5 is cleaved into C5a and C5b. C5a, displays powerful biological activities that lead to inflammation (1) (3). It is a strong chemoattractant involved in the recruitment of inflammatory cells such as neutrophils, eosinophils, monocytes, and T lymphocytes, the activation of phagocytic cells and the induction of the release of granule-based enzymes and generation of oxidants, all mechanisms that may contribute to innate immune functions but also tissue damage. Excessive complement activation leading to elevated plasma levels of C5a is known to be associated with many clinical conditions, including sepsis, adult respiratory distress syndrome, rheumatoid arthritis, Alzheimer's disease (4), and ischemic heart disease.

C5b, on the other hand, through its multiple binding sites, initiates and directs the assembly of the membrane attack complex (MAC). C5b serves as an anchor for the assembly of C6, C7, C8, and C9 (known as C5b-9) and is inserted into the cell membrane of the pathogens, leading to cell lysis.

There is therefore a need for a medicament which is able to specifically target C5a and not C5b. An anti-05 monoclonal antibody had been developed for being used in therapy. This antibody prevents collagen-induced arthritis and ameliorates established disease (5) (6). However, this antibody blocks both C5a and C5b, the decrease of C5b levels which is necessary for formation of MAC is a drawback of this antibody.

There is therefore still a need for a more specific therapy only targeting C5a and letting C5b intact. As demonstrated herein, an oligonucleotide-based therapy is assumed to be specifically targeting C5a while keeping the C5b intact for formation of MAC.

The pro-inflammatory cytokine interleukin-1 (IL-1) is an important mediator controlling local and systemic effects on a wide variety of target cells, there by regulating immunity and inflammation (7). It mediates inflammation by recruitment of neutrophils, activation of macrophages and stimulation of T and B cells.

IL-1 binds to IL-1 receptor type I (IL-1RI), which results in the recruitment of the IL-1 receptor accessory protein (IL-1RAcP) (8). IL-1RAcP does not recognize the ligand but stabilizes IL-1 binding to the IL-1RI. Furthermore, IL-1RAcP is a crucial co-receptor in this complex by enabling recruitment and binding of intracellular adaptor proteins such as MyD88 and kinases such as IL-1R-associated kinases, ultimately leading to NF-κB activation. In addition to the trans-membrane form of IL-1RAcP, a smaller and soluble protein comprising the three extracellular Ig domains and a unique C-terminal domain has been identified. This sIL-1RAcP is mainly produced by the liver (29) and circulates systemically. Another member of IL-1 receptor family is IL-1RII which upon binding of IL-1 also associates with IL-1RAcP; however, this doesn't lead to signal transduction. So this receptor is considered as a decoy receptor and can be found in trans-membrane and soluble forms (9).

IL-1 levels increase in some inflammatory diseases like rheumatoid arthritis. So it is necessary to decrease and regulate the level and the activity of IL-1. sIL-1RAcP can interact with soluble IL-1RII thus forming a high affinity IL-1 scavenger (8) and it has been already shown (9) that systemic over-expression of sIL-1RAcP by an adenoviral expression vector in mice markedly ameliorates collagen-induced arthritis (CIA). Therefore there is a need for a medicament for increasing the amount of circulating sIL-1RAcP. Adenoviral over-expression of sIL-1RAcP is not attractive since virus vectors may be considered as unsafe and are not easy to generate. As demonstrated herein, an oligonucleotide-based therapy is thought to be more specific, safer and cheaper than such virus-based therapy.

Several treatments are already known to treat an inflammatory disease such as RA. However, each of these treatments has drawbacks. Therefore there is still a need for designing new treatments for inflammatory diseases such as RA which do not have all the drawbacks of existing treatments.

DESCRIPTION OF THE INVENTION

The inventors designed two types of molecules: one type or family of molecule is specifically able to decrease the level of a C5a, the second one is able to increase the level of a soluble IL-1RAcP.

Molecule

In a first aspect, there is provided a molecule, preferably an oligonucleotide or a functional equivalent thereof, which is able of altering or alters the splicing of a pre-mRNA encoding a C5 in order to decrease the amount of a C5a. A molecule, preferably an oligonucleotide as defined herein is specifically able to alter or modify the splicing of a C5 pre-mRNA in order to decrease the amount of a C5a protein. Said alteration of the splicing of the C5 pre-mRNA preferably occurs in a patient or in a cell of said patient or in a cell line or in a cell free in vitro system as identified herein. As explained earlier herein, a C5 protein is cleaved into a C5a and a C5b protein.

Decreasing the production of a C5a in a patient or in a cell of said patient or in a cell line or in a cell free in vitro system may be assessed at the mRNA level and preferably means that 99%, 90%, 80%, 70%, 60%, 50%, 40%, 30%, 20%, 10%, 5% or less of the initial amount of a C5a mRNA, is still detectable by RT PCR. In this context, a C5a mRNA means a targeted exon of C5 encoding a part of a C5a protein. Preferably, no C5a mRNA is detectable.

Decreasing the production of a C5a in a patient or in a cell of said patient or in a cell line or in a cell free in vitro system may be assessed at the mRNA level and preferably means that 99%, 90%, 80%, 70%, 60%, 50%, 40%, 30%, 20%, 10%, 5% or less of the initial amount of a targeted exon of C5 encoding a part of C5a, is still detectable by RT PCR. Preferably, no targeted exon encoding a part of C5a mRNA is detectable.

Decreasing the production of a C5a in a patient or in a cell of said patient or in a cell line or in a cell free in vitro system may be assessed at the protein level (by immunofluorescence and/or western blot analyses) and preferably means that 99%, 90%, 80%, 70%, 60%, 50%, 40%, 30%, 20%, 10%, 5% or less of the initial amount of a C5a protein, is still detectable by immunofluorescence or western blot analysis. Preferably, no C5a protein is detectable.

A decrease is preferably assessed in a tissue or in a cell of an individual or a patient by comparison to the amount present in said individual or patient before treatment with said molecule or composition of the invention. Alternatively, the comparison can be made with a tissue or cell of said individual or patient which has not yet been treated with said molecule or composition in case the treatment is local. The comparison is preferably carried out everywhere where C5 is expressed or produced. Since C5 is primarily expressed or produced in the liver of any subject it is preferred that said comparison is carried out using a hepatic cell, and/or an hepatic tissue and/or a liver. In a preferred embodiment, a tissue is a hepatic tissue, a cell is an hepatic cell. The same holds for IL-1RAcP as later defined herein.

In a preferred embodiment, a molecule, preferably an oligonucleotide is such that the amount of a C5b is unchanged. The amount of a C5b in a patient or in a cell of said patient or in a cell line or in a cell free in vitro system may be assessed at the mRNA level or at the protein level as earlier defined herein. In a preferred embodiment, the amount of a C5b is unchanged by comparison to the amount of a C5b in the same system (in a patient or in a cell of said patient or in a cell line or in a cell free in vitro system) before treatment. It is however possible that the amount of a C5b may be decreased of 1%, 2%, 5%, 10%, 15%, 20%, 25%, 30%, 35% by comparion to the initial amount of a C5b before treatment. A preferred assay has been designed in order to assess whether a functional C5b protein is being produced. This assay is described in the experimental part and is called Haemolytic complement assay.

In a preferred embodiment, a molecule, preferably an oligonucleotide is able to induce the skipping of exon 17 of the pre-mRNA encoding a C5. This exon is attractive to be skipped since it will lead to the production of a non-functional truncated C5a protein missing the anaphylatoxin domain. Said truncated and non-functional C5a protein is expected to be degraded by the ubiquitin-proteasome system. Alternatively, if a premature stop codon is introduced into a C5 gene, it will cause to nonsense-mediated decay of the remaining part of C5a.

In a further aspect, there is provided a molecule, preferably an oligonucleotide or a functional equivalent thereof, which is able of altering the splicing of a pre-mRNA encoding a IL-1RAcP in order to increase the amount of a soluble IL-1RAcP. A molecule, preferably an oligonucleotide as defined herein is specifically able to alter or modify the splicing of a pre-mRNA encoding a IL-1RAcP in order to increase the amount of a soluble IL-1RAcP. Said alteration of the splicing of the IL-1RAcP pre-mRNA preferably occurs in a patient or in a cell of said patient or in a cell line or in a cell free in vitro system as identified herein.

Within the context of the invention, a soluble IL-1RAcP preferably means a secreted form of said IL-1RAcP. A secreted or soluble protein means that said protein is not bound to a cell membrane. Therefore, an IL-1RAcP will be said soluble or secreted when it is detectable in a cellular fraction which is not associated with a cell membrane using a conventional assay known to the skilled person. An example of such a cellular fraction is a cellular supernatant or a serum. An example of a conventional assay is an ELISA or a western blotting.

A secreted or soluble protein is defined by opposition to a membrane bound form of a protein. A membrane bound form protein is a protein having an amino acid sequence that spans a cell membrane with amino acid on each side of the membrane. Therefore, a protein will be said membrane bound when it is detectable in a cellular fraction which is associated with a cell membrane using a conventional assay known to the skilled person. An example of such a cellular fraction is a cellular extract comprising membrane bound proteins. Such extract may be prepared using Nonidet P40. An example of a conventional assay is an ELISA or a Western Blot.

Increasing the production of a soluble IL-1RAcP in a patient or in a cell of said patient or in a cell line or in a cell free in vitro system may be assessed at the mRNA level and preferably means that said mRNA is detectable using RT-PCR.

Increasing the production of a soluble IL-1RAcP in a patient or in a cell of said patient or in a cell line or in a cell free in vitro system may be assessed at the protein level (by immunofluorescence and/or western blot analyses and/or ELISA) and preferably means that said protein is detectable.

Alternatively or in combination with the assessment of the production of a soluble IL-1RAcP protein (assessment at the protein or mRNA level), one may also assess the presence of unbound or free or soluble IL-1. In a preferred embodiment, an oligonucleotide or a functional equivalent thereof, which is able of altering the splicing of a pre-mRNA encoding a IL-1 RAcP in order to decrease the amount of an unbound or free IL-1 and therefore its biological activity.

Within the context of the invention, an unbound or free IL-1 preferably means an IL-1 which is not bound to a protein. Therefore, an IL-1 will be said free when it is detectable or detected in a cellular fraction which is not associated with a cell membrane or with a protein or a protein complex using a conventional assay known to the skilled person. An example of such a cellular fraction is a cellular supernatant or a serum. An example of a conventional assay is an ELISA or a western blot.

Decreasing the amount of a soluble or free or unbound IL-1 in a patient or in a cell of said patient or in a cell line or in a cell free in vitro system may be assessed at the protein level (by immunofluorescence and/or western blot analyses and/or ELISA) and preferably means that a free IL-1 is decreased of 1%, 2%, 5%, 10%, 15%, 20%, 25%, 30%, 35% by comparison to the initial amount of said free IL-1 before treatment. The amount of IL-1 may be quantified using Western blot as exemplified in the experimental part.

Alternatively or in combination with the assessment of the production of a soluble IL-1RAcP protein, one may also assess the presence or expression level or activation level of a molecule known to be induced or activated by IL-1. For example, it is known that IL-1 induces the activation of NF- κB and/or the production or release of several chemokines as IL-6/ICAM-1. Therefore, alternatively or in combination with the assessment of the production of a soluble IL-1RAcP protein, one may also assess the activation of NF-κB and/or the release of IL-6/ICAM-1 In a preferred embodiment, an oligonucleotide or a functional equivalent thereof, which is able of altering the splicing of a pre-mRNA encoding a IL-1RAcP in order to decrease the activation of NF-κB and/or the release of IL-6/ICAM-1.

Decreasing the activation of NF-κB and/or the release of IL-6/ICAM-1 in a patient or in a cell of said patient or in a cell line or in a cell free in vitro system may be assessed at the protein level as exemplified in the experimental part and preferably means that activated NF-κB and/or released IL-6/ICAM-1 is decreased of 1%, 2%, 5%, 10%, 15%, 20%, 25%, 30%, 35% by comparison to the initial amount of said activated NF-κB and/or released IL-6/ICAM-1 before treatment.

An increase or a decrease is preferably assessed in a tissue or in a cell of an individual or a patient by comparison to the amount present in said individual or patient before treatment with said molecule or composition of the invention. Alternatively, the comparison can be made with a tissue or cell of said individual or patient which has not yet been treated with said molecule or composition in case the treatment is local. In a preferred embodiment, a tissue is a hepatic tissue, a cell is an hepatic cell, since as for C5, IL-1RAcP is primarily expressed or produced in the liver.

In a preferred embodiment, a molecule, preferably an oligonucleotide is able to induce the skipping of exon 9 of the pre-mRNA encoding an IL-1RAcP. This exon is attractive to be skipped since its encodes the transmembrane domain of a IL-1RAcP and since its skipping is expected not to disturb the open reading frame of a IL-1RAcP. We expect that the skipping of exon 9 of a pre-mRNA encoding a IL-1 RAcP will lead to the production of a soluble IL-1RAcP.

General Technical Information as to Both Types of Oligonucleotides of the Invention An oligonucleotide as used herein preferably comprises an antisense oligonucleotide or antisense oligoribonucleotide: also named an AON. In a preferred embodiment an exon skipping technique is applied. Exon skipping interferes with the natural splicing processes occurring within a eukaryotic cell. In higher eukaryotes the genetic information for proteins in the DNA of the cell is encoded in exons which are separated from each other by intronic sequences. These introns are in some cases very long. The transcription machinery of eukaryotes generates a pre-mRNA which contains both exons and introns, while the splicing machinery, often already during the production of the pre-mRNA, generates the actual coding region for the protein by splicing together the exons present in the pre-mRNA.

Exon-skipping results in mature mRNA that lacks at least one skipped exon. Thus, when said exon codes for amino acids, exon skipping leads to the expression of an altered protein. Technology for exon-skipping is currently directed towards the use of antisense oligonucleotides (AONs).

The skipping of an exon is preferably induced by the binding of AONs targeting either one or both of the splice sites, or exon-internal sequences. An oligonucleotide directed toward an exon internal sequence typically exhibits no overlap with non-exon sequences. It preferably does not overlap with the splice sites at least not insofar as these are present in the intron. An oligonucleotide directed toward an exon internal sequence preferably does not contain a sequence complementary to an adjacent intron. An oligonucleotide according to the invention, or a functional equivalent thereof, is for inhibiting inclusion of an exon of a C5, respectively IL-1RAcP pre-mRNA is order to produce a C5 respectively IL1RAcP protein which lacks said exon.

An exon skipping technique is preferably applied such that the absence of an exon from a mRNA produced from a C5 gene or pre-mRNA generates a coding region for a non-functional C5a protein which is expected to be degraded. C5b is therefore still produced and in theory no or less C5a is produced, whereas without AON C5a and C5b are produced in similar amounts.

In the case of IL-1RAcP, an exon skipping technique is preferably applied such that the absence of an exon from said mRNA will result in the production of a soluble form instead of a membrane-bound form. In this context, inhibiting inclusion of an exon preferably means that the amount of detected full length or original C5a, respectively full length or membrane-bound IL-1RAcP mRNA and/or protein is decreased as earlier defined herein.

Since an exon of a C5, respectively IL-1RAcP pre-mRNA will only be included into the resulting mRNA when both the splice sites are recognised by the spliceosome complex, splice sites have been obvious targets for AONs. One embodiment therefore provides an oligonucleotide, or a functional equivalent thereof, comprising a sequence which is complementary to a non-exon region of a C5, respectively IL-1RAcP pre mRNA. In one embodiment an AON is used which is solely complementary to a non-exon region of a C5, respectively IL-1RAcP pre mRNA. This is however not necessary: it is also possible to use an AON which comprises an intron-specific sequence as well as exon-specific sequence. Such AON comprises a sequence which is complementary to a non-exon region of a C5, respectively IL-1RAcP pre mRNA, as well as a sequence which is complementary to an exon region of a C5, respectively IL-1RAcP pre mRNA. Of course, an AON is not necessarily complementary to the entire sequence of a C5, respectively IL-1RAcP exon or intron. AONs which are complementary to a part of such exon or intron are preferred. An AON is preferably complementary to at least part of a C5, respectively IL-1RAcP exon and/or intron, said part having at least 8, 9, 10, 11, 12, 13, 14, 15, 16, 17, 18, 19, 20 nucleotides or more.

Splicing of a C5, respectively IL-1RAcP pre-mRNA occurs via two sequential transesterification reactions. First, the 2'OH of a specific branch-point nucleotide within the intron that is defined during spliceosome assembly performs a nucleophilic attack on the first nucleotide of the intron at the 5' splice site forming the lariat intermediate. Second, the 3'OH of the released 5' exon then performs a nucleophilic attack at the last nucleotide of the intron at the 3' splice site thus joining the exons and releasing the intron lariat. The branch point and splice sites of an intron are thus involved in a splicing event. Hence, an oligonucleotide comprising a sequence which is complementary to such branch point and/or splice site is preferably used for exon skipping. Further provided is therefore an oligonucleotide, or a functional equivalent thereof, which comprises a sequence which is complementary to a splice site and/or branch point of a C5, respectively IL-1RAcP pre mRNA.

Since splice sites contain consensus sequences, the use of an oligonucleotide or a functional equivalent thereof (herein also called an AON) comprising a sequence which is complementary of a splice site involves the risk of promiscuous hybridization. Hybridization of AONs to other splice sites than the sites of the exon to be skipped could easily interfere with the accuracy of the splicing process. To overcome these and other potential problems related to the use of AONs which are complementary to an intron sequence, one preferred embodiment provides an oligonucleotide, or a functional equivalent thereof, comprising a sequence which is complementary to a C5, respectively IL-1RAcP pre-mRNA exon. Preferably, said AON is capable of specifically inhibiting an exon inclusion signal of at least one exon in said pre-mRNA. Interfering with an exon inclusion signal (EIS) has the advantage that such elements are located within the exon. By providing an AON for the interior of the exon to be skipped, it is possible to interfere with the exon inclusion signal thereby effectively masking the exon from the splicing apparatus. The failure of the splicing apparatus to recognize the exon to be skipped thus leads to exclusion of the exon from the final mRNA. This embodiment does not interfere directly with the enzymatic process of the splicing machinery (the joining of the exons). It is thought that this allows the method to be more specific and/or reliable. It is thought that an EIS is a particular structure of an exon that allows splice acceptor and donor to assume a particular spatial conformation. In this concept it is the particular spatial conformation that enables the splicing machinery to recognize the exon. However, the invention is certainly not limited to this model. In a preferred embodiment, use is made of an oligonucleotide which is capable of binding to an exon and is capable of inhibiting an EIS. An AON may specifically contact said exon at any point and still be able to specifically inhibit said EIS.

Within the context of the invention, a molecule may mean any type of molecule as long as this molecule is able of altering or alters the splicing of a pre-mRNA encoding the C5 in order to decrease the amount of C5a, respectively altering or alters the splicing of a pre-mRNA encoding the IL-1RAcP in order to increase the amount of soluble IL-1RAcP in a cell or in a tissue or in an individual as identified herein. Said molecule is therefore able to induce the production of a mRNA missing an exon, preferably exon 17 in the case of C5a, respectively exon 9 in the case of IL-1RAcP, resulting in the production of a protein or a protein isoform, i.e. a non-functional C5a protein as identified herein or a soluble IL-1RAcP protein as identified herein by altering the splicing of a corresponding pre-mRNA. Therefore in a preferred embodiment, said molecule does not prevent translation of the corresponding mRNA since a protein will be formed or produced from said mRNA. Preferably said molecule is an oligonucleotide or a functional equivalent thereof. A functional equivalent of an oligonucleotide preferably means an oligonucleotide as defined herein wherein one or more nucleotides have been substituted and wherein an activity of said functional equivalent is retained to at least some extent. Preferably, an activity of said functional equivalent is providing a detectable decrease of C5a, respectively a detectable production of soluble IL-1RAcP. Said activity of said functional equivalent is therefore preferably assessed by quantifying the amount of a C5a, respectively soluble IL-1 RAcP protein or by quantifying the amount of the corresponding mRNA. The assessment of said activity of an oligonucleotide is preferably done by RT-PCR (m-RNA) or by immunofluorescence or Western blot analyses (protein). Said activity is preferably retained to at least some extent when it represents at least 50%, or at least 60%, or at least 70% or at least 80% or at least 90% or at least 95% or more of corresponding activity of said oligonucleotide the functional equivalent derives from. Such activity may be measured in a liver tissue or in a liver cell of an individual or in vitro in a cell by comparison to an activity of a corresponding oligonucleotide of said oligonucleotide the functional equivalent derives from. Throughout this application, when the word oligonucleotide is used it may be replaced by a functional equivalent thereof as defined herein.

Hence, an oligonucleotide, or a functional equivalent thereof, comprising or consisting of a sequence which is complementary to or binds a C5, respectively an IL-1RAcP pre-mRNA exon preferably providing a therapeutic result. In one preferred embodiment an oligonucleotide, or a functional equivalent thereof, is used which comprises or consists of a sequence which is complementary to or binds at least part or to a contiguous stretch of a C5, respectively IL-1RAcP pre-mRNA exon, said part having or comprising at least 8 nucleotides. However, said part may also have at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides. A part of a C5, respectively IL-1RAcP pre-mRNA exon to which an oligonucleotide is complementary may also be called a contiguous stretch of said pre-mRNA. For murine or human C5, a preferred contiguous stretch is a stretch of pre-mRNA exon 17, more preferably a stretch of pre-mRNA exon 17 close to the 3' end of said exon. In this context, close to may mean 1 nucleotide from the 3' end of said exon or 2, 3, 4, 5, 6, 7, 8, 9, 10, 11, or 12 nucleotides. The murine and human pre mRNA sequence of exon 17 is represented by SEQ ID NO: 1 and 2 respectively. Therefore, an oligonucleotide is preferably complementary to or binds a stretch of at least 8 nucleotides of SEQ ID NO: 1 or 2.

Alternatively, an oligonucleotide, or a functional equivalent thereof, comprises or consists of a sequence which is complementary to or binds intron 17 of C5 pre-mRNA. The murine and human pre-mRNA sequence of intron 17 is represented by SEQ ID NO: 3 and 4 respectively. Therefore, an oligonucleotide is preferably complementary to or binds a stretch of at least 8 nucleotides of SEQ ID NO: 3 or 4.

The expression "binds an exon or intron of a C5 pre-mRNA" in this context, preferably means that said oligonucleotide is able to decrease the production of a C5a in a patient or in a cell of said patient or in a cell line. C5a in this context may refer to a C5a protein. The expression "binds an exon or intron of a IL1RAcP pre-mRNA" in this context, preferably means that said oligonucleotide is able of altering the splicing of a pre-mRNA encoding a IL-1RAcP in order to increase the amount of a soluble IL-1RAcP or in a cell free in vitro system may be assessed at the mRNA level. A preferred mRNA sequence of a murine C5 is represented by SEQ ID NO:7. A preferred mRNA sequence of a human C5 is represented by SEQ ID NO:8. A preferred mRNA sequence of a murine IL-1RAcP is represented by SEQ ID NO:9. A preferred mRNA sequence of a human IL-1RAcP is represented by SEQ ID NO:10.

For murine or human IL-1RAcP, a preferred contiguous stretch is a stretch of pre-mRNA exon 9, preferably comprising an ESE site, more preferably comprising an ESE site close to the 5' end of exon 9. In this context, close to may mean 1 nucleotide from the 5' end of said pre-mRNA exon or 2, 3, 4, 5, 6, 7, 8, 9, 10, 11, or 12 nucleotides.

For murine or human IL-1RAcP, another preferred contiguous stretch is a stretch of pre-mRNA exon 9 comprising an ESE site and/or close to the 3' end of exon 9. Even more preferably, for human IL-1RAcP, a contiguous stretch is a stretch of pre-mRNA exon 9 comprising an ESE site and/or close to the 3' end of exon 9. In this context, close to may mean 1 nucleotide from the 3' end of said pre-mRNA exon or 2, 3, 4, 5, 6, 7, 8, 9, 10, 11, or 12 nucleotides. A murine and human sequence of pre-mRNA exon 9 are represented by SEQ ID NO: 5 and 6. Therefore, an oligonucleotide is preferably complementary to or bind a stretch of at least 8 nucleotides of SEQ ID NO: 5 or 6.

Alternatively, an oligonucleotide, or a functional equivalent thereof, comprises or consists of a sequence which is complementary to or binds human intron 8 or 9 of IL-1RAcP pre-mRNA. A human pre-mRNA sequence of intron 8 and 9 is represented by SEQ ID NO: 62 and 63 respectively. Therefore, an oligonucleotide is preferably complementary to or binds a stretch of at least 8 nucleotides of SEQ ID NO: 62 or 63.

Alternatively, an oligonucleotide, or a functional equivalent thereof, comprises or consists of a sequence which is complementary to or binds a pre-mRNA sequence comprising part of intron 8 and part of exon 9 or a sequence overlapping intron 8 and exon 9 (i.e. boundaries of intron 8-exon 9) of human IL-1RAcP or a sequence comprising part of exon 9 and part of intron 9 or a sequence overlapping exon 9 and intron 9 (i.e. boundaries of exon 9-intron 9) of human IL-1RAcP. A preferred human pre-mRNA sequence overlapping intron 8 and exon 9 is represented by SEQ ID NO: 64. A preferred human pre-mRNA sequence overlapping exon 9 and intron 9 is represented by SEQ ID NO: 65. Therefore, an oligonucleotide is preferably complementary to or binds a stretch of at least 8 nucleotides of SEQ ID NO: 64 or 65.

Most preferably an oligonucleotide is used which comprises or consists of a sequence which is complementary to at least part of a C5 pre-mRNA, respectively at least part of an IL-1RAcP pre-mRNA said part having or comprising at least 8 nucleotides. However, said part may also have at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides.

More preferred oligonucleotides for C5 are represented by a sequence that comprises or consists of each of the following sequences SEQ ID NO: 11 to SEQ ID NO:24:

SEQ ID NO: 11, 12, 16, 17, 18, 19, 20, 22, 23 and 24 (i.e. PS295, PS296, PS349, PS350, PS351, PS352, PS353, 377, 378 and 379) are complementary or target or binds to a part or a stretch of exon 17 of a C5, SEQ ID NO: 13, 14 and 21 (i.e. PS329, PS330 and PS354) are complementary or target or binds to a part or a stretch of exon 17-intron 17 boundaries of a C5, SEQ ID NO:15 (i.e. PS348) is complementary or targets or binds to a part or a stretch of intron 16-exon 17 boundaries of a C5.

More preferred oligonucleotides comprise or consist of SEQ ID NO:13 (PS329) and SEQ ID NO:22 (377).

More preferred oligonucleotides for IL-1RAcP are represented by a sequence that comprises or consists of each of the following sequences SEQ ID NO: 25 to SEQ ID NO:42.

SEQ ID NO: 25, 26, 28, 33, 34, 35, 36, 39, 40, 41 (i.e. PS299, PS300, PS326, PS357, PS 358, PS359, PS360, 373, 374 and 375) are complementary or target or binds to a part or a stretch of exon 9 of a IL-1RAcP, SEQ ID NO: 27, 31, 32 and 42 (i.e. PS325, PS355, PS356 and 376) are complementary or target or binds to a part or a stretch of intron 8-exon 9 boundaries of a IL-1RAcP, SEQ ID NO: 29, 30, 37 and 38 (i.e. PS327, PS328, PS361 and 372) are complementary or target or binds to a part or a stretch of exon 9-intron 9 boundaries of a IL-1RAcP.

More preferred oligonucleotides comprise or consist of SEQ ID NO:26 (PS300) and SEQ ID NO:39 (373).

Each of the oligonucleotides is identified in table 3. Table 5 identifies the region targeted by each oligonucleotide.

In a preferred embodiment, an oligonucleotide of the invention as identified earlier herein further comprises at least one inosine and/or a base able to form a wobble base pair is present in said sequence. Preferably, an inosine has been introduced in one of these sequences to replace a guanine, adenine, or a uracil. The use of an inosine and/or a nucleotide containing a base able to form a wobble base pair in an oligonucleotide of the invention is very attractive as explained below. Inosine for example is a known modified base which can pair with three bases: uracil, adenine, and cytosine. Inosine is a nucleoside that is formed when hypoxanthine is attached to a ribose ring (also known as a ribofuranose) via a β-N9-glycosidic bond. Inosine is commonly found in tRNAs and is essential for proper translation of the genetic code in wobble base pairs. A wobble base pair is a G-U and I-U/I-A/I-C pair fundamental in RNA secondary structure. Its thermodynamic stability is comparable to that of the Watson-Crick base pair. Wobble base pairs are critical for the proper translation of the genetic code. The genetic code makes up for disparities in the number of amino acids (20) for triplet codons (64), by using modified base pairs in the first base of the anti-codon. Similarly, when designing primers for polymerase chain reaction, inosine is useful in that it will indiscriminately pair with adenine, thymine, or cytosine.

A first advantage of using such a base allows one to design a primer that spans a single nucleotide polymorphism (SNP), without worry that the polymorphism will disrupt the primer's annealing efficiency. Therefore in the invention, the use of such a base allows to design an oligonucleotide that may be used for an individual having a SNP within the pre-mRNA stretch which is targeted by an oligonucleotide of the invention.

A second advantage of using an inosine and/or a base able to form a wobble base pair in an oligonucleotide of the invention is when said oligonucleotide would normally contain a CpG if one would have designed it as being complementary to a pre-mRNA stretch as identified herein. The presence of a CpG in an oligonucleotide is usually associated with an increased immunogenicity of said oligonucleotide (10). This increased immunogenicity is undesired. Replacing one, two or more CpG by the corresponding inosine and/or a base able to form a wobble base pair in said oligonucleotide is expected to provide an oligonucleotide with a decreased and/or acceptable level of immunogenicity. Immunogenicity may be assessed in an animal model by assessing the presence of $CD4^+$ and/or $CD8^+$ T cells and/or inflammatory myeloid cells in a biopsy of said animal. Immunogenicity may also be assessed in blood of an animal or of a human being treated with an oligonucleotide of the invention by detecting the presence of a neutralizing antibody and/or an antibody recognizing said oligonucleotide using a standard immunoassay known to the skilled person such as an ELISA.

An increase in immunogenicity preferably corresponds to a detectable increase of at least one of these cell types by comparison to the amount of each cell type in a corresponding biopsy of an animal before treatment or treated with a corresponding oligonucleotide having at least one inosine and/or a base able to form a wobble base pair. Alternatively, an increase in immunogenicity may be assessed by detecting the presence or an increasing amount of an antibody recognizing said oligonucleotide using a standard immunoassay. A decrease in immunogenicity preferably corresponds to a detectable decrease of at least one of these cell types by comparison to the number of corresponding cell types in a corresponding biopsy of an animal before treatment or treated with a corresponding oligonucleotide having no inosine and/or a base able to form a wobble base pair. Alternatively a decrease in immunogenicity may be assessed by the absence of or a decreasing amount of said antibodies using a standard immunoassay.

A third advantage of using an inosine and/or a base able to form a wobble base pair in an oligonucleotide of the invention is to avoid or decrease a potential multimerisation or aggregation of oligonucleotides. It is for example known that an oligonucleotide comprising a G-quartet motif has the tendency to form a quadruplex, a multimer or aggregate formed by the Hoogsteen base-pairing of four single-stranded oligonucleotides (11), which is of course not desired: as a result the efficiency of the oligonucleotide is expected to be decreased. Multimerisation or aggregation is preferably assessed by standard polyacrylamide non-denaturing gel electrophoresis techniques known to the skilled person. In a preferred embodiment, less than 20% or 15%, 10%, 7%, 5% or less of a total amount of an oligonucleotide of the invention has the capacity to multimerise or aggregate assessed using the assay mentioned above.

A fourth advantage of using an inosine and/or a base able to form a wobble base pair in an oligonucleotide of the invention is thus also to avoid quadruplex structures which have been associated with antithrombotic activity (12) as well as with the binding to, and inhibition of, the macrophage scavenger receptor (13).

A fifth advantage of using an inosine and/or a base able to form a wobble base pair in an oligonucleotide of the invention is to allow designing an oligonucleotide with improved RNA binding kinetics and/or thermodynamic properties. The RNA binding kinetics and/or thermodynamic properties are at least in part determined by the melting temperature of an oligonucleotide (Tm; calculated with the oligonucleotide properties calculator (http://www.unc.edu/~cail/biotool/oligo/index.html) for single stranded RNA using the basic Tm and the nearest neighbour model), and/or the free energy of the AON-target exon complex (using RNA structure version 4.5). If a Tm is too high, the oligonucleotide is expected to be less specific. An acceptable Tm and free energy depend on the sequence of the oligonucleotide. Therefore, it is difficult to give preferred ranges for each of these parameters. An acceptable Tm may be at least 35 and not more than 65° C. and an acceptable free energy may be at least 15 and not more than 45 kcal/mol.

The skilled person may therefore first choose an oligonucleotide as a potential therapeutic compound. In a second step, he may use the invention to further optimise said oligonucleotide by decreasing its immunogenicity and/or avoiding aggregation and/or quadruplex formation and/or by optimizing its Tm and/or free energy of the AON-target complex. He may try to introduce at least one inosine and/or a base able to form a wobble base pair in said oligonucleotide at a suitable position and assess how the immunogenicity and/or aggregation and/or quadruplex formation and/or Tm and/or free energy of the AON-target complex have been altered by the presence of said inosine and/or a base able to form a wobble base pair. If the alteration does not provide the desired alteration or decrease of immunogenicity and/or aggregation and/or quadruplex formation and/or its Tm and/or free energy of the AON-target complex he may choose to introduce a further inosine and/or a base able to form a wobble base pair in said oligonucleotide and/or to introduce a given inosine and/or a base able to form a wobble base pair at a distinct suitable position within said oligonucleotide In a preferred embodiment, an oligonucleotide of the invention which comprises a sequence that is complementary to part of a C5, respectively IL-1RAcP pre-mRNA is such that the complementary part is at least 50% of the length of the oligonucleotide of the invention, more preferably at least 60%, even more preferably at least 70%, even more preferably at least 80%, even more preferably at least 90% or even more preferably at least 95%, or even more preferably 98% or even more preferably at least 99%, or even more preferably 100%. In a most preferred embodiment, the oligonucleotide of the invention consists of a sequence that is complementary to part of a C5, respectively IL-1RAcP pre-mRNA as defined herein. As an example, an oligonucleotide may comprise a sequence that is complementary to part of a C5, respectively IL-1RAcP pre-mRNA as defined herein and additional flanking sequences. In a more preferred embodiment, the length of said complementary part of said oligonucleotide is of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides. Preferably, additional flanking sequences are used to modify the binding of a protein to the oligonucleotide, or to modify a thermodynamic property of the oligonucleotide, more preferably to modify target RNA binding affinity.

One preferred embodiment provides an oligonucleotide, or a functional equivalent thereof which comprises:
  a sequence which is complementary to a region of a C5 respectively IL-1RAcP pre-mRNA exon that is hybridized to another part of a C5 respectively IL-1RAcP exon (closed structure), and
  a sequence which is complementary to a region of a C5 respectively IL-1RAcP pre-mRNA exon that is not hybridized in said C5 respectively IL-1RAcP pre-mRNA (open structure).

For this embodiment, reference is made to WO 2004/083432, which is incorporated by reference in its entirety. RNA molecules exhibit strong secondary structures, mostly due to base pairing of complementary or partly complementary stretches within the same RNA. It has long since been thought that structures in the RNA play a role in the function of the RNA. Without being bound by theory, it is believed that the secondary structure of the RNA of an exon plays a role in structuring the splicing process. The structure of an exon is one parameter which is believed to direct its inclusion into the mRNA. However, other parameters may also play a role therein. Herein this signalling function is referred to as an exon inclusion signal. A complementary oligonucleotide of this embodiment is capable of interfering with the structure of the exon and thereby capable of interfering with the exon inclusion signal of the exon. It has been found that many complementary oligonucleotides indeed comprise this capacity, some more efficient than others. Oligonucleotides of this preferred embodiment, i.e. those with the said overlap directed towards open and closed structures in the native exon RNA, are a selection from all possible oligonucleotides. The selection encompasses oligonucleotides that can efficiently interfere with an exon inclusion signal. Without being bound by theory it is thought that the overlap with an open structure improves the invasion efficiency of the oligonucleotide and prevent the binding of splicing factors (i.e. increases the efficiency with which the oligonucleotide can enter the structure), whereas the overlap with the closed structure subsequently increases the efficiency of interfering with the secondary structure of the RNA of the exon, and thereby interfere with the exon inclusion signal. It is found that the length of the partial complementarity to both the closed and the open structure is not extremely restricted. We have observed high efficiencies with oligonucleotides with variable lengths of complementarity in either structure. The term complementarity is used herein to refer to a stretch of nucleic acids that can hybridise to another stretch of nucleic acids under physiological conditions. It is thus not absolutely required that all the bases in the region of complementarity are capable of pairing with bases in the opposing strand. For instance, when designing the oligonucleotide one may want to incorporate for instance a residue that does not base pair with the base on the complementary strand. Mismatches may to some extent be allowed, if under the circumstances in the cell, the stretch of nucleotides is sufficiently capable of hybridising to the complementary part. In this context, "sufficiently" preferably means that using a gel mobility shift assay as described in example 1 of EP 1 619 249, binding of an oligonucleotide is detectable. Optionally, said oligonucleotide may further be tested by transfection into human liver cells. Skipping of the targeted exon may be assessed by RT-PCR (as described in EP 1 619 249). The complementary regions are preferably designed such that, when combined, they are specific for the exon in the pre-mRNA. Such specificity may be created with various lengths of complementary regions as this depends on the actual sequences in other (pre-)mRNA in the system. The risk that also one or more other pre-mRNA will be able to hybridise to the oligonucleotide decreases with increasing size of the oligonucleotide. It is clear that oligonucleotides comprising mismatches in the region of complementarity but that retain the capacity to hybridise to the targeted region(s) in the pre-mRNA, can be used in the present invention. However, preferably at least the complementary parts do not comprise such mismatches as these typically have a higher efficiency and a higher specificity, than oligonucleotides having such mismatches in one or more complementary regions. It is thought that higher hybridisation strengths, (i.e. increasing number of interactions with the opposing strand) are favourable in increasing the efficiency of the process of interfering with the splicing machinery of the system. Preferably, the complementarity is between 90 and 100%. In general this allows for 1 or 2 mismatch(es) in an oligonucleotide of 20 nucleotides.

The secondary structure is best analysed in the context of the pre-mRNA wherein the exon resides. Such structure may be analysed in the actual RNA. However, it is currently possible to predict the secondary structure of an RNA molecule (at lowest energy costs) quite well using structure-modelling programs. A non-limiting example of a suitable program is RNA mfold version 3.1 server (14). A person skilled in the art will be able to predict, with suitable reproducibility, a likely structure of the exon, given the nucleotide sequence. Best predictions are obtained when providing such modelling programs with both the exon and flanking intron sequences. It is typically not necessary to model the structure of the entire pre-mRNA.

The open and closed structure to which the oligonucleotide is directed, are preferably adjacent to one another. It is thought that in this way the annealing of the oligonucleotide to the open structure induces opening of the closed structure whereupon annealing progresses into this closed structure. Through this action the previously closed structure assumes a different conformation. The different conformation results in the disruption of the exon inclusion signal. However, when potential (cryptic) splice acceptor and/or donor sequences are present within the targeted exon, occasionally a new exon inclusion signal is generated defining a different (neo) exon, i.e. with a different 5' end, a different 3' end, or both. This type of activity is within the scope of the present invention as the targeted exon is excluded from the mRNA and as long as C5a protein is decreased, respectively a soluble IL1RAcP is produced.

Further provided is an oligonucleotide, or a functional equivalent thereof comprising a sequence that is complementary to a binding site for a serine-arginine (SR) protein in RNA of an exon of a pre-mRNA. In WO 2006/112705 we have disclosed the presence of a correlation between the effectivity of an exon-internal antisense oligonucleotide (AON) in inducing exon skipping and the presence of a (for example by ESE finder) predicted SR binding site in the target pre-mRNA site of said AON. Therefore, in one embodiment an oligonucleotide is generated comprising determining a (putative) binding site for an SR (Ser-Arg) protein in RNA of a targeted exon of a C5, respectively IL-1RAcP premRNA and producing an oligonucleotide that is complementary to said RNA and that at least partly overlaps said (putative) binding site. The term "at least partly overlaps" is defined herein as to comprise an overlap of only a single nucleotide of an SR binding site as well as multiple nucleotides of said binding site as well as a complete overlap of said binding site. This embodiment preferably further comprises determining from a secondary structure of said RNA, a region that is hybridised to another part of said RNA (closed structure) and a region that is not hybridised in said structure (open structure), and subsequently generating an oligonucleotide that at least partly overlaps said (putative) binding site and that overlaps at least part of said closed structure and overlaps at least part of said open structure. In this way we increase the chance of obtaining an oligonucleotide that is capable of interfering with the exon inclusion from the pre-mRNA into mRNA. It is possible that a first selected SR-binding region does not have the requested open-closed structure in which case another (second) SR protein binding site is selected which is then subsequently tested for the presence of an open-closed structure. This process is continued until a sequence is identified which contains an SR protein binding site as well as a(n) (partly overlapping) open-closed structure. This sequence is then used to design an oligonucleotide which is complementary to said sequence.

Such a method for generating an oligonucleotide is also performed by reversing the described order, i.e. first generating an oligonucleotide comprising determining, from a secondary structure of RNA from a C5, respectively IL-1RAcP exon, a region that assumes a structure that is hybridised to another part of said RNA (closed structure) and a region that is not hybridised in said structure (open structure), and subsequently generating an oligonucleotide, of which at least a part of said oligonucleotide is complementary to said closed structure and of which at least another part of said oligonucleotide is complementary to said open structure. This is then followed by determining whether an SR protein binding site at least overlaps with said open/closed structure. In this way the method of WO 2004/083432 is improved. In yet another embodiment the selections are performed simultaneously.

Without wishing to be bound by any theory it is currently thought that use of an oligonucleotide directed to an SR protein binding site results in (at least partly) impairing the binding of an SR protein to the binding site of an SR protein which results in disrupted or impaired splicing.

Preferably, an open/closed structure and an SR protein binding site partly overlap and even more preferred an open/closed structure completely overlaps an SR protein binding site or an SR protein binding site completely overlaps an open/closed structure. This allows for an improved disruption of exon inclusion.

Besides consensus splice sites sequences, many (if not all) exons contain splicing regulatory sequences such as exonic splicing enhancer (ESE) sequences to facilitate the recognition of genuine splice sites by the spliceosome (15, 16). A subgroup of splicing factors, called the SR proteins, can bind to these ESEs and recruit other splicing factors, such as U1 and U2AF to (weakly defined) splice sites. The binding sites of the four most abundant SR proteins (SF2/ASF, SC35, SRp40 and SRp55) have been analyzed in detail and these results are implemented in ESE finder, a web source that predicts potential binding sites for these SR proteins (15, 16).

There is a correlation between the effectiveness of an oligonucleotide and the presence/absence of an SF2/ASF, SC35 and SRp40 binding site. In a preferred embodiment, the invention thus provides a combination as described above, wherein said SR protein is SF2/ASF or SC35 or SRp40.

In one embodiment an oligonucleotide, or a functional equivalent thereof is capable of specifically binding a regulatory RNA sequence which is required for the correct splicing of a exon in a transcript. Several cis-acting RNA sequences are required for the correct splicing of exons in a transcript. In particular, supplementary elements such as intronic or exonic splicing enhancers (ISEs and ESEs) or silencers (ISSs and ESEs) are identified to regulate specific and efficient splicing of constitutive and alternative exons. Using sequence-specific antisense oligonucleotides (AONs) that bind to the elements, their regulatory function is disturbed so that the exon is skipped, as shown for DMD. Hence, in one preferred embodiment an oligonucleotide or functional equivalent thereof is used which is complementary to an intronic splicing enhancer (ISE), an exonic splicing enhancer (ESE), an intronic splicing silencer (ISS) and/or an exonic splicing silencer (ESS). As already described herein before, a C5, respectively IL-1RAcP exon is in one preferred embodiment skipped by an agent capable of specifically inhibiting an exon inclusion signal of said exon, so that said exon is not recognized by the splicing machinery as a part that needs to be included in the mRNA. As a result, a mRNA without said exon is formed.

An oligonucleotide used herein is preferably complementary to a consecutive part or a contiguous stretch of 8 and 50 nucleotides of a C5, respectively IL-1RAcP exon RNA or a C5, respectively IL-1RAcP intron RNA. In one embodiment an oligonucleotide used herein is complementary to a consecutive part or a contiguous stretch of 14 and 50 nucleotides of a C5, respectively IL-1RAcP exon RNA or a C5, respectively IL-1RAcP intron RNA. Preferably, said oligonucleotide is complementary to a consecutive part or contiguous stretch of 14 and 25 nucleotides of said exon RNA. More preferably, an oligonucleotide is used which comprises a sequence which is complementary to a consecutive part or a contiguous stretch of 20 and 25 nucleotides of a C5, respectively IL-1RAcP exon RNA or a C5, respectively IL-1RAcP intron RNA. Therefore such preferred oligonucleotide, which is complementary to a consecutive part or a contiguous stretch of 8 and 50 nucleotides of a C5, respectively IL-1RAcP exon pre-mRNA induces the production of a C5a protein missing the region encoded by said exon, respectively a IL-1RAcP protein missing the region encoded by said exon.

Different types of nucleic acid monomers may be used to generate an oligonucleotide.

A nucleic acid may have a backbone, a sugar and/or a base modification compared to an RNA-based oligonucleotide.

Preferred backbone modifications include but are not limited to: phopshorodithioate, phosphorothioate, a chirally pure phosphorothioate, methyl phosphonate, and/or H-phosphonate.

Alternatively or in combination with a backbone modification, a nucleic acid may have a sugar modification and/or a base modification.

Preferred sugar modifications include: carbasugar and/or azasugar including mixmers. Other sugar modifications include: a locked nucleic acid (LNA), an ethylene-bridged nucleic acid (ENA) and/or a variant thereof including mixmers. Other sugar modifications include 2'-halide and/or 2'-O-alkyl and/or 2'-O-(substituted)alkyl modifications such as 2'-O-methyl, 2'-F, 2'-O-(2-methoxy)ethyl 2'-O-ethyl, 2'-O-allyl, 2'-O-butynyl, 2'-O-propargyl, 2'-O-(2-amino)ethyl. The skilled person will understand that not each sugar may be modified the same way. Several distinct modified sugars may be combined into one single nucleic acid.

Preferred base modifications include: a 5-halogenated uracil and/or a cytosine, a 5-aminomethyl-uracil, a 2,6-diaminopurine, a 5-propargyl-cytosine, a 5-propargyl-uracil, a G-clamp and its derivatives), a 5-methyl-cytosine- and/or a 5-methyl-uracil. The skilled person will understand that not each base may be modified the same way. Several distinct modified bases may be combined into one single nucleic acid.

Preferably, said oligonucleotide comprises RNA, as RNA/RNA duplexes are very stable. Since one of the aims of the exon skipping technique is to direct splicing in a subject, it is preferred that an RNA oligonucleotide comprises a modification providing the RNA with an additional property, for instance resistance to endonucleases, exonucleases, and RNaseH, additional hybridisation strength, increased stability (for instance in a bodily fluid), increased or decreased flexibility, reduced toxicity, increased intracellular transport, tissue-specificity, etc. Preferred modifications have been identified above.

Preferably said oligonucleotide comprises or consists of 2'-Omethyl RNA monomers connected through a phosphorothioate backbone. One embodiment thus provides an oligonucleotide which comprises RNA further containing a modification, preferably a 2'-O-methyl modified ribose (RNA), more preferably a 2'-O-methylphosphorothioate RNA.

In one embodiment the invention provides a hybrid oligonucleotide comprising a 2'-O-methyl phosphorothioate oligoribonucleotide modifications and locked nucleic acid monomers. This particular oligonucleotide comprises better sequence specificity compared to an equivalent consisting of locked nucleic acid only, and comprises improved effectivity when compared with an oligonucleotide consisting of 2'-O-methyl phosphorothioate oligoribonucleotide modification.

Therefore in a preferred embodiment, an oligonucleotide comprises RNA and preferably said RNA contains a modification, more preferably a 2'-O-methyl modified ribose (RNA) or deoxyribose (DNA) modification or wherein said functional equivalent of said oligonucleotide comprises PNA, carbaborane-containing peptide nucleic acid, (LNA), (ENA), unlocked nucleic acid (UNA), glycol nucleic acid (GNA), morpholino phosphorodiamidate, or any combination thereof, most preferably morpholino phosphorodiamidate. In a preferred embodiment, an oligonucleotide has a backbone, a sugar and/or a base modification compared to an RNA-based oligonucleotide, preferably wherein the oligonucleotide comprises or consists of one or more 2'-O-methyl phosphorothioate and/or a morpholino phosphordiamidate nucleotide.

Each of the backbone, sugar, base modifications identified are believed to increase or enhance the ability of the oligonucleotide to induce skipping of the targeted exon.

With the advent of nucleic acid mimicking technology it has become possible to generate molecules that have a similar, preferably the same hybridisation characteristics in kind not necessarily in amount as nucleic acid itself. Such functional equivalents are of course also suitable for use in the invention. Preferred examples of functional equivalents of an oligonucleotide are PNA and/or LNA. Most preferably, a morpholino phosphorodiamidate is used. Suitable but non-limiting examples of equivalents of oligonucleotides of the invention can be found in 17-23. Hybrids between one or more of the equivalents among each other and/or together with nucleic acid are of course also suitable. In a preferred embodiment LNA is used as a functional equivalent of an oligonucleotide, as LNA displays a higher target affinity and reduced toxicity. LNA also shows a higher efficiency of exon skipping.

Further provided is an oligonucleotide which comprises at least 8, preferably 16 to 80, consecutive nucleotides that are complementary to a first exon of a C5, respectively IL-1RAcP pre-mRNA and wherein a nucleotide sequence is used which comprises at least 8, preferably 16 to 80, consecutive nucleotides that are complementary to a second exon of said C5, respectively IL-1RAcP pre-mRNA.

In one preferred embodiment said first and said second exon are separated in said C5, respectively IL-1RAcP pre-mRNA by at least one exon to which said oligonucleotide is not complementary. Alternatively, said first and said second exon are adjacent.

It is possible to specifically promote the skipping of also the intervening exons by providing a linkage between the two complementary oligonucleotides. Hence, in one embodiment stretches of nucleotides complementary to at least two C5, respectively IL-1RAcP exons are separated by a linking moiety. The at least two stretches of nucleotides are thus linked in this embodiment so as to form a single molecule. Further provided is therefore an oligonucleotide, or functional equivalent thereof which is complementary to at least two parts of two exons in a C5, respectively IL-1RAcP pre-mRNA, said oligonucleotide or functional equivalent comprising at least two parts wherein a first part comprises an oligonucleotide having at least 8, preferably 16 to 80, consecutive nucleotides that are complementary to a first of said at least two exons and wherein a second part comprises an oligonucleotide having at least 8, preferably 16 to 80, consecutive nucleotides that are complementary to a second exon in said C5, respectively IL-1RAcP pre-mRNA. The linkage may be through any means but is preferably accomplished through a nucleotide linkage. In the latter case the number of nucleotides that do not contain an overlap between one or the other complementary exon can be zero, 1, 2, 3 or 4 to 40 nucleotides. The linking moiety can be any type of moiety capable of linking oligonucleotides. Preferably, said linking moiety comprises at least 4 uracil nucleotides. Currently, many different compounds are available that mimic hybridisation characteristics of oligonucleotides. Such a compound, called herein a functional equivalent of an oligonucleotide, is also suitable for the present invention if such equivalent comprises similar hybridisation characteristics in kind not necessarily in amount. Suitable functional equivalents are mentioned earlier in this description. As mentioned, an oligonucleotide of the invention does not have to consist of only oligonucleotides that contribute to hybridisation to the targeted exon. There may be additional material and/or nucleotides added.

Dose ranges of oligonucleotide according to the invention are preferably designed on the basis of rising dose studies in clinical trials (in vivo use) for which rigorous protocol requirements exist. A molecule or an oligonucleotide as defined herein may be used at a dose which is from 0.1 to 60 mg/kg, preferably from 0.5 to 55 mg/kg.

In a preferred embodiment, a concentration of an oligonucleotide as defined herein, which is from 0.1 nM to 1 µM is used. Preferably, this range is for in vitro use in a cellular model such as liver cells or liver tissue. More preferably, the concentration used is from 0.3 to 700 nM, even more preferably from 1 to 600 nM, even more preferably from 50 to 550 nM. If several oligonucleotides are used, this concentration or dose may refer to the total concentration or dose of oligonucleotides or the concentration or dose of each oligonucleotide added.

The ranges of concentration or dose of oligonucleotide(s) as given above are preferred concentrations or doses for in vitro or ex vivo uses. The skilled person will understand that depending on the oligonucleotide(s) used, the target cell to be treated, the gene target and its expression levels, the medium used and the transfection and incubation conditions, the concentration or dose of oligonucleotide(s) used may further vary and may need to be optimised any further.

In a preferred embodiment, such molecule, preferably oligonucleotide is preferably a medicament or for use as a medicament. More preferably, said medicament is for preventing or treating an inflammatory disorder to a subject in the need thereof. Within the context of the invention, an inflammatory disorder is any inflammatory disease or condition and preferably refers to a disease, disorder, or other medical condition that at least in part results from or is aggravated by a C5a protein or by IL-1 signalling. Examples of inflammatory diseases or conditions include, but are not limited to, rheumatoid arthritis (RA), juvenile rheumatoid arthritis, psoriasis, psoriatic arthritis, ankylosing spondylitis, inflammatory bowel disease (including Crohn's disease or ulcerative colitis), hepatitis, sepsis, alcoholic liver disease, and non-alcoholic steatosis, nephritis, such as glomerular nephritis, asthma, endocarditis, myasthenia gravis As used herein, the term "hepatitis" refers to a gastroenterological disease, condition, or disorder that is characterized, at least in part, by inflammation of the liver. Examples of hepatitis include, but are not limited to, hepatitis associated with hepatitis A virus, hepatitis B virus, hepatitis C virus, or liver inflammation associated with ischemia/reperfusion.

Even more preferably, said medicament is able to decrease the amount of a C5a, respectively increase the amount of a soluble IL-1RAcP as defined earlier herein.

In a more preferred embodiment, said medicament is able to alleviate one or more symptom(s) from a treated patient and/or one or more characteristic(s) or parameter(s) of a cell or tissue from a treated patient is/are improved using a molecule or a composition of the invention. For each inflammatory disease, the skilled person knows at least one symptom, parameter or characteristic, values of said parameter or characteristic associated with said disease and how to assess each of them. Below, we give a parameter specific for Rheumatoid arthritis. Rheumatoid arthritis is a disease that is preferably diagnosed after having assessed the index of Disease Activity Score (DAS) or the related DAS28 (van Riel P. L. C. M., (2001), Best Practice & Research Clinical Rheumatology, 15: 67-76) including the measurements of several parameters and symptoms on a subject. The assessment of said indexes may be carried out by a clinician examining a subject. In a more preferred embodiment, said medicament is able to alleviate one or more symptom(s) from a treated patient and/or one or more characteristic(s) or parameter(s) of a cell or tissue from a treated patient is/are improved using a molecule or a composition of the invention when said medicament is able to induce a significant change in DAS or DAS28. Other ways of assessing rheumatoid arthritis are also described in (van Riel P. L. C. M., (2001), Best Practice & Research Clinical Rheumatology, 15: 67-76 and in Gester A. M., (1999), Baillière's Clinical Immunology, 13: 629-644). A medicament as defined herein is able to improve one parameter if after at least one week, one month, six month, one year or more of treatment using a molecule able of altering the splicing of a pre-mRNA encoding a C5 in order to decrease the amount of a C5a and/or able of altering the splicing of a pre-mRNA encoding a IL-1RAcP in order to increase the amount of a soluble IL-1RAcP, the value of said parameter has been improved of at least 1%, 2%, 5%, 10% or more by comparison of the value of said parameter before the onset of the treatment.

A medicament as defined herein is able to alleviate one symptom or one characteristic of a patient or of a cell, tissue or organ or said patient if after at least one week, one month, six month, one year or more of treatment using a molecule able of altering the splicing of a pre-mRNA encoding a C5 in order to decrease the amount of a C5a and/or able of altering the splicing of a pre-mRNA encoding a IL-1RAcP in order to increase the amount of a soluble IL-1RAcP, said symptom or characteristic is no longer detectable.

An oligonucleotide as defined herein for use according to the invention may be suitable for administration to a cell, tissue and/or an organ in vivo of individuals affected by or at risk of developing an inflammatory disorder, and may be administered in vivo, ex vivo or in vitro. Said oligonucleotide may be directly or indirectly administered to a cell, tissue and/or an organ in vivo of an individual affected by or at risk of developing an inflammatory disorder, and may be administered directly or indirectly in vivo, ex vivo or in vitro. An oligonucleotide of the invention should be able to be delivered everywhere where C5, IL1RAcP is expressed or produced. Since C5 and soluble IL-1RAcP are primarily expressed or produced in the liver of any subject it is preferred that an oligonucleotide of the invention is able to be delivered to an hepatic cell, and/or to an hepatic tissue and/or to a liver. Preferably said cells are cells of an individual suffering from an inflammatory disorder. Preferably said tissue is a tissue of an individual suffering from an inflammatory disorder. Preferably said liver is a liver of an individual suffering from an inflammatory disorder.

An oligonucleotide of the invention may be indirectly administrated using suitable means known in the art. An oligonucleotide may for example be provided to an individual or a cell, tissue or organ of said indivival in the form of an expression vector wherein the expression vector encodes a transcript comprising said oligonucleotide. The expression vector is preferably introduced into a cell, tissue, organ or individual via a gene delivery vehicle. In a preferred embodiment, there is provided a viral-based expression vector comprising an expression cassette or a transcription cassette that drives expression or transcription of a molecule as identified herein. A preferred delivery vehicle is a viral vector such as an adeno-associated virus vector (AAV), or a retroviral vector such as a lentivirus vector (24-26) and the like. Also plasmids, artificial chromosomes, plasmids suitable for targeted homologous recombination and integration in the human genome of cells may be suitably applied for delivery of an oligonucleotide as defined herein. Preferred for the current invention are those vectors wherein transcription is driven from PolIII promoters, and/or wherein transcripts are in the form fusions with U1 or U7 transcripts, which yield good results for delivering small transcripts. It is within the skill of the artisan to design suitable transcripts. Preferred are PolIII driven transcripts. Preferably in the form of a fusion transcript with an U1 or U7 transcript (24-26). Such fusions may be generated as described (27, 28). The oligonucleotide may be delivered as is. However, the oligonucleotide may also be encoded by the viral vector. Typically this is in the form of an RNA transcript that comprises the sequence of the oligonucleotide in a part of the transcript.

Improvements in means for providing an individual or a cell, tissue, organ of said individual with an oligonucleotide and/or an equivalent thereof, are anticipated considering the progress that has already thus far been achieved. Such future improvements may of course be incorporated to achieve the mentioned effect on restructuring of mRNA using a method of the invention. An oligonucleotide and/or an equivalent thereof can be delivered as is to an individual, a cell, tissue or organ of said individual. When administering an oligonucleotide and/or an equivalent thereof, it is preferred that an oligonucleotide and/or an equivalent thereof is dissolved in a solution that is compatible with the delivery method. For intravenous, subcutaneous, intramuscular, intrathecal and/or intraventricular administration it is preferred that the solution is a physiological salt solution. Particularly preferred in the invention is the use of an excipient that will aid in delivery of each of the constituents as defined herein to a cell and/or into a cell, preferably a liver cell. Preferred are excipients capable of forming complexes, nanoparticles, micelles, vesicles and/or liposomes that deliver each constituent as defined herein, complexed or trapped in a vesicle or liposome through a cell membrane. Many of these excipients are known in the art. Suitable excipients comprise polyethylenimine (PEI), or similar cationic polymers, including polypropyleneimine or polyethylenimine copolymers (PECs) and derivatives, synthetic amphiphils (SAINT-18), Lipofectin™, DOTAP and/or viral capsid proteins that are capable of self assembly into particles that can deliver each constituent as defined herein to a cell, preferably a liver cell. Such excipients have been shown to efficiently deliver an oligonucleotide such as antisense nucleic acids to a wide variety of cultured cells, including liver cells. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver each constituent as defined herein, preferably an oligonucleotide across cell membranes into cells.

In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an oligonucleotide. The skilled person may select and adapt any of the above or other commercially available alternative excipients and delivery systems to package and deliver an oligonucleotide for use in the current invention to deliver it for the treatment of an inflammatory disorder in humans.

In another embodiment, an oligonucleotide could be covalently or non-covalently linked to a molecule. A preferred molecule is a ligand as defined below and/or a molecule that alters stability and/or pharmacokinetics and/or pharmacodynamics of said oligonucleotide. Each of these parameters (i.e. stability and/or pharmacokinetics and/or pharmacodynamics) could be assessed using assays known to the skilled person.

An oligonucleotide could be covalently or non-covalently linked to a ligand specifically designed to facilitate the uptake in to the cell, cytoplasm and/or its nucleus. Such ligand could comprise (i) a compound (including but not limited to peptide(-like) structures) recognising cell, tissue or organ specific elements facilitating cellular uptake and/or (ii) a chemical compound able to facilitate the uptake in to cells and/or the intracellular release of an oligonucleotide from vesicles, e.g. endosomes or lysosomes.

Therefore, in a preferred embodiment, an oligonucleotide is formulated in a composition or a medicament or a composition which is provided with at least an excipient and/or a ligand for delivery and/or a delivery device thereof to a cell and/or enhancing its intracellular delivery. Accordingly, the invention also encompasses a pharmaceutically acceptable composition comprising an oligonucleotide and further comprising at least one excipient and/or a ligand for delivery and/or a delivery device of said oligonucleotide to a cell and/or enhancing its intracellular delivery.

Depending on their identity, the skilled person will know which type of formulation is the most appropriate for each constituent as defined herein. In a preferred embodiment, the invention provides a composition or a preparation which is in the form of a kit of parts comprising an oligonucleotide and a further adjunct compound as later defined herein.

A preferred oligonucleotide as defined herein is for preventing or treating an inflammatory disorder in an individual. An individual which may be treated using an oligonucleotide of the invention may already have been diagnosed as having an inflammatory disorder. Alternatively an individual which may be treated using an oligonucleotide of the invention may not have yet been diagnosed as having an inflammatory disorder but may be an individual having an increased risk of developing an inflammatory disorder in the future given his or her genetic background. A preferred individual is a human being.

Composition

In a further aspect, there is provided a composition comprising a molecule, preferably an oligonucleotide as defined herein. Preferably, said composition comprises at least two distinct oligonucleotides as defined herein; one designed for being able of altering the splicing of a pre-mRNA of a C5 in order to decrease the amount of C5a and the other being able of altering the splicing of a pre-mRNA encoding a IL-1RAcP in order to increase the amount of soluble IL-1RAcP and/or decrease the activation of NF-κB and/or decrease the release of IL-6/ICAM-1 and/or decrease of the amount of free IL-1. Alternatively, these two distinct oligonucleotides are designed to skip distinct two or more exons of a C5, respectively IL-1RAcP pre-mRNA as earlier defined herein for multi-exon skipping.

In a preferred embodiment, said composition being preferably a pharmaceutical composition said pharmaceutical composition comprising a pharmaceutically acceptable carrier, diluent and/or excipient.

Such a pharmaceutical composition may comprise any pharmaceutically acceptable carrier, filler, preservative, solubilizer, diluent and/or excipient is also provided. Such pharmaceutically acceptable carrier, filler, preservative, solubilizer, diluent and/or excipient may for instance be found in Remington: The Science and Practice of Pharmacy, 20th Edition. Baltimore, Md.: Lippincott Williams & Wilkins, 2000. Each feature of said composition has earlier been defined herein.

If several oligonucleotides are used, concentration or dose already defined herein may refer to the total concentration or dose of all oligonucleotides used or the concentration or dose of each oligonucleotide used or added. Therefore in one embodiment, there is provided a composition wherein each or the total amount of oligonucleotide used is dosed in an amount ranged between 0.5 mg/kg and 60 mg/kg.

Use

In a further aspect, there is provided the use of an oligoucleotide or of a composition as defined herein for the manufacture of a medicament for preventing or treating an inflammatory disorder in an individual. Each feature of said use has earlier been defined herein.

A treatment in a use or in a method according to the invention is at least one week, at least one month, at least several months, at least one year, at least 2, 3, 4, 5, 6 years or more. Each molecule or oligonucleotide or equivalent thereof as defined herein for use according to the invention may be suitable for direct administration to a cell, tissue and/or an organ in vivo of individuals affected by or at risk of developing an inflammatory disorder, and may be administered directly in vivo, ex vivo or in vitro. The frequency of administration of an oligonucleotide, composition, compound of the invention may depend on several parameters such as the age of the patient, the mutation of the patient, the number of molecules (i.e. dose), the formulation of said molecule. The frequency may be daily, weekly or ranged between at least once in two weeks, or three weeks or four weeks or five weeks or a longer time period.

Method

In a further aspect, there is provided a method for alleviating one or more symptom(s) of an inflammatory disorder in an individual, in a cell, tissue or organ of said individual or alleviate one or more characteristic(s) or symptom(s) of a cell, tissue or organ of said individual, the method comprising administering to said individual an oligonucleotide or a composition as defined herein.

There is further provided a method for enhancing, inducing or promoting skipping of an exon from a C5 respectively IL-1RAcP pre-mRNA in a cell expressing said pre-mRNA in an individual suffering from an inflammatory disorder, the method comprising administering to said individual an oligonucleotide or a composition as defined herein. Further provided is a method for increasing the production of a soluble IL-1RAcP and/or decreasing the production of an C5a in a cell, said cell comprising a pre-mRNA of a gene encoding an IL-1RAcP respectively a C5, the method comprising providing said cell with an oligonucleotide or composition of the invention and allowing translation of mRNA produced from splicing of said pre-mRNA. In one embodiment said method is performed in vitro, for instance using a cell culture. Preferably, said method is in vivo. Each feature of these methods has already been defined herein. In a method of the invention, an oligonucleotide may be combined with an additional compound known to be used for treating an inflammatory disorder in an individual. Such compound may be an antibody, a DMARD (disease-modifying anti-rheumatic drugs), a NSAID (Non-steroidal Anti-inflammatory Agents) and/or a different or distinct AON. Alternatively or in combination with the increase of the production of a soluble IL-1RAcP, an AON may decrease the activation of NF-κB and/or decrease the release of IL-6/ICAM-1 and/or decrease the amount of free IL-1 as earlier defined herein.

Throughout the application, when one refers to an IL-1, an IL-1RAcP, a C5, a C5a, an IL-6, one refers to the protein or peptide unless otherwise indicated. Therefore, an IL-1 may be substituted with an IL-1 protein. Unless otherwise indicated each embodiment as described herein may be combined with another embodiment as described herein.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a molecule or an oligonucleotide as defined herein may comprise additional component(s) than the ones specifically identified, said additional component(s) not altering the unique characteristic of the invention.

In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "approximately" or "about" when used in association with a numerical value (approximately 10, about 10) preferably means that the value may be the given value of 10 more or less 1% of the value.

All patent and literature references cited in the present specification are hereby incorporated by reference in their entirety. Each embodiment as identified herein may be combined together unless otherwise indicated.

The invention is further explained in the following examples. These examples do not limit the scope of the invention, but merely serve to clarify the invention.

EXAMPLES

Haemolytic Complement Assay

Figure 1:
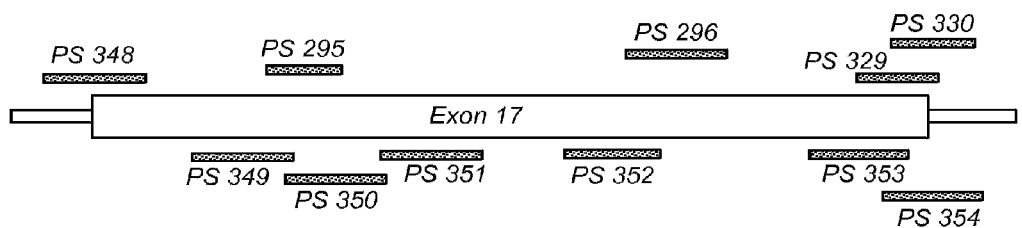
FIG. 1. AONs targeting mouse C5 pre-mRNA exon 17 with flanking introns

C5 and C5Δ17 (without exon 17) cDNAs were synthesized and ligated to the vector pcDNA 3.1 (−). Human embryonic kidney cells (HEK 293) will be transfected with either C5 or C5Δ17 containing expression vector, and cultured in G-418 containing medium to select positive colonies. The positive colonies then will be grown in serum-free conditions and the culture medium will be collected, purified and tested for the presence of C5 and C5Δ17 by western blot. The purified supernatants than will be subjected to hemolytic complement assay which will show if intact C5b is present or not. In this functional assay both supernatants will be treated with C5-deficient serum than this solution will be incubated with red-blood-cells. The degree of C5b-9 mediated lysis will be determined by reading OD at 415 nm Materials & Methods (for all Examples)

AON Design and Chemistry:

AONs were designed based on the criteria previously discussed in Aartsma-Rus et al., 2009 (.Aartsma-Rus et al., Guidelines for antisense oligonucleotide design and insight in splice modulating mechanisms, Mol Ther. 2009 March; 17(3):548-53). The locations of potential exonic splice enhancer (ESE) or to 5'/3' splice sites sequences were predicted by using ESE finder 3.0 (http://rulai.cshl.edu/tools/ESE/). The secondary structure of the pre-mRNA as predicted by M-FOLD (http://frontend.bioinfo.rpi.edu/applications/mfold/) was also taken into account. AONs were 21-25mers with 2'O-methyl ribose molecules and a full phosphorothioate backbone (Prosensa). The sequences of the AONs are provided in the sequence listing. 5'FAM label control AON was used to test the efficiency of transfection into target cells. Additionally, selected AONs were either modified by increasing their length to 25mers and/or by incorporation of some locked nucleic acid (LNA) modifications in order to increase their efficiencies for the targets. For designing these AONs, the criteria at http://www.exiqon.com/custom-antisense-oligonucleotides were used.

Cell Culture:

L929 (mouse connective tissue), NIH-3T3 (Mouse embryonic fibroblast) and HEPG2 (Human hepatocellular liver carcinoma) cell line were maintained in DMEM+2 mM L-glutamine+10% FCS+1× Pen-Strep at 37C in 5% $CO_2$. They were used to test exon skipping using AONs for mIL-1RAcP, mC5 and hIL-1RAcP/hC5, respectively.

AON Delivery in Cell Culture:

L929 and NIH-3T3 cells were grown in DMEM+10% FBS+1% Pen-Strep containing medium and passed when approaching confluence with 0.25% Trypsin to provide experimental cultures in 6 well plates. On the day of transfection the cells (0.5-1 $10^6$ cells/well of a 6 well-plate) were cultured in DMEM+10% FCS (in the absence of antibiotics). After 3-4 to 5-6 hours, the cells were transfected with Lipofectamine 2000+AON mixtures prepared according to the manufacturer's procedure (Invitrogen). The final concentration of AONs was adjusted to be 500 nM, 200 nM or 100 nM in different experiments. Each AON has been tested 3 times to determine skipping efficiency. Transfection solution for one well of a six well plate was prepared as follows: AONs were diluted in 250 µl Optimem serum reduced medium (final concentration of AON when added to cells were either 100 nM, 200 nM, 100 nM, 50 nM, 20 nM or 10 nM, depending on the purpose of the experiment). In addition 5 µl of Lipofectamine was diluted in 250 µl Optimem and both dilutions were incubated for 5 µl at room temperature. Then the two dilutions were mixed (total volume 500 µl), incubated for 20 µl and added to the cells plates were rocked back and forth a few times and incubated at 37° C. with 5% $CO_2$ Transfection medium was changed after 6-8 hours with DMEM+10% FBS and the cells were ready for RNA isolation after 18-24 hours.

RNA Isolation and Reverse-Transcription PCR:

24 hours after transfection of the AON from $10^6$ cells total RNA was isolated using Trizol reagent (Invitrogen). cDNA was synthesized with Transcriptor First Strand cDNA Synthesis Kit by using random hexamer primers according to the manufacturer's procedure (Roche). 2 µL of cDNA was used in PCR reaction with the final concentration of 50 mL. Primer sequences are from 5' to 3' mC5 F(orward): aaacgcagatgactccatt, mC5 R(everse): acgcgatgaatttcccatag, mIL-1RAcP F: gaggatctcaggcgcaacta, mIL-1RAcP R: tcagcagcacaaattcctctt, hC5 F: ttctcaggccaagaagaacg, hC5 R: gggcaaactgcaactgtttt, hIL-1RAcP F: caagcgcagctatgtctgtc, hIL-1RAcP R: tctcggtcaaagatgcacag. Beta Actin gene (ACTB) was used as positive control, ACTB F: actgctctggctcctagcac, ACTB R:ccaccgatcacacagagta. These primers are identified by SEQ ID NO: 43-52 in the sequence listing. PCR products were analyzed on 1.5% agarose gel stained with EtBr. For sequencing, PCR products were purified with NucleoSpin Extract II Kit (Macherey-Nagel). The sequence analysis of the products was done by LGTC (Leiden). For RNA isolation from liver, 15-30 mg of mouse liver was transferred to MagnaLyzer Green Beads (Roche) tube. 500 ul PBS containing 5 ul 2-Mercaptoethanol was added and the samples were homogenized 20 sec at 7000 rpm in MagnaLyzer, followed by another 10 sec. at 7000 rpm. in between it was kept on ice. 200 µl of the homogenized tissue was added to 800 µl Trizol reagent and RNA isolation was performed according to the manufacturer's procedure.

Real-Time PCR Analysis:

2.5 µl cDNA (20× diluted), 5 µl 2× FastStart Universal SYBR Green Master (ROX., Roche), 0.25 µl 10 pmole primers were used in reaction mixture with the total volume of 10 µL. Primer sequences are from 5' to 3' as follows; mIL-1RAcP F: tggtagtggttctcattgtggt, mIL-RAcP R: tccaaagtgagctcggtaaaa, mC5 F: aaagcccccataaacctgtc, mC5 R: tcggatatctgccttcatca. All quantitative PCR data was normalized to the expression of housekeeping genes ACTB and Cytochrome c-1. (Cyc1); ACTB F: actgctctggctcctagcac, ACTB R:ccaccgatcacacagagta, Cyc1 F: tgctacacggaggaagaagc, Cyc1 R: catcatcattagggccatcc. LightCycler 480 Real-Time PCR System (Roche) was used to run the reactions and the data were analyzed by the software program qBase (Biogazelle NV, Belgium). These primers are identified by SEQ ID NO: 53-60 in the sequence listing.

In-Vivo Detection of Skipping at mRNA Level

Six weeks old C57BL/6 male mice were purchased from Jackson Laboratory and injected IV or IP with 50 or 100 mg/kg of AON by using insulin Myjector U-100 insulin syringes for 3 or 4 consecutive days. On post-injection Day 1 or Day 5, livers were harvested and kept in liquid $N_2$ until RNA isolation to prevent degradation of RNA. RNA isolation and RT-PCR procedures were performed as mentioned before.

Protein Isolation from Cells

The culture medium was removed from the cells and 1 ml cold RIPA buffer (including Roche complete mini protease inhibitor) was added on $5\times10^6$ cells in 75 cm2 flask, and kept on ice for 5 min while rocked. The cell lysate was gathered using cell scraper and transferred to a microcentrifuge tube. The samples were centrifuged at 14.000×g for 15 min to pellet the cell debrids. The supernatant was transferred to a new tube and protein concentration was determined by using Quanti-it Protein Assay kit.

SDS-PAGE

10% gel separation gel was prepared by mixing 7.9 ml water, 5 ml 1.5 M Tris-Hcl pH 8.8, 6.70 ml acrylamide, 200 µl 10% SDS, 8 µl TEMED and 200 µl 10% APS. Immediately after adding TEMED and APS, the gel was poured (7.2 ml/gel) and 1 ml isopropanol/Miliq (50/50) was put on top of gel to let it polymerize. The gel should polymerize in about 30 min. Then the stacking gel was prepared by mixing; 5.5 ml water, 1 ml 1 M tris-HCl pH6.8, 1.33 ml acrylamide, 80 µl 10% SDS, 8 µl TEMED and 80 µl 10% APS were mixed and pipette on separation gel, put combs and let it polymerase.

The protein samples were prepared (15 µl sample+5 µl loading buffer, in the hood) and boiled the samples 5 min at 95° C., cool on ice. When the stacking gel was set running buffer was added to the upper and lower chambers of the gel unit and loaded 15 µl into each slot. The gel was run at 80V until the samples have reached the separation gel, and than increased to 120V until the blue color run from the gel.

Western Blotting 2 fiber pads and three precut Whatman 3MM papers were prepared and saturated in transfer buffer. PVDF membranes were wet briefly in 100% methanol, rinsed with double distilled water and incubated in PBS. The system was assembled in to the cassette in the following order: 1 fiber pad, 3 Whatman filter papers, gel, PVDF membrane, 3 Whatman filter paper, 1 fiber pad. The cassettes were inserted into the electrode module and placed into the transfer tank in a way that the membrane is between the gel and the anode and the samples were run in cold room (4° C.) for 1 hour at 100V. The membranes were blocked in Odyssey Blocking Buffer for 1 hour at room temperature or overnight at 4° C. on a rocking platform with gentle shaking The primary antibody was diluted in Odyssey Blocking Buffer and to lower background, 0.2% Tween-20 was added to the diluted antibody and incubated overnight with gentle shaking on a rocket platform (optimum incubation times vary for different primary antibodies). The rabbit anti-human IL-1RAcP Antibody (AbD serotec, product number AHP549) and Chicken polyclonol beta actin Antibody (Abcam, Product number Ab 13822) were used. The membranes were washed 4 times for 5 minutes at room temperature in PBS+0.1% Tween-20 with gentle shaking and incubated with the fluorescently-labelled secondary antibody diluted in Odyssey Blocking Buffer (plus 0.2% Tween-20 and 0.01%-0.02% SDS) for 1 h at room temperature, protected from light during incubation. The second antibody was the goat anti-rabbit Ab (Licor, product number 926-32211) and Donkey anti-chicken Ab (Licor, product number 926-32228). The membranes were washed 4 times for 5 minutes at room temperature in PBS+0.1% Tween-20 with gentle shaking (protected from light) and than the membrane were scanned in Li-cor Odyssey Imaging System.

NF-κB Activation Assay

NIH-3T3 cells were seeded in 24-well culture plates at 40.000 cells/well. The next day, cells were transfected with the control and test AONs according to the procedure above. The cells were incubated overnight and transfected with pNFκB-Luc and pRL-CMV plasmids with Lipofectamine 2000. Next morning cells were stimulated with mIL-1β for 4 hours. The reagents of Dual-Luciferase reporter assay (Promega) were prepared according to the manifacturer's manual. The cultured medium was removed and the cells washed with 1 ml PBS. 250 µl 1× Passive Lysis Buffer was added on to the cells and scraped. The cell lysate was transfer to a microcentrifuge tube and centrifuged for 5 min, at 13,000 g at 4° C. to pellet debris. 30 µl of the lysate was added to each well of 96-well plate. 100 µl of LAR II was added to each well and firefly luciferase activity was measured in a luminometer Then 100 µl of 1× Stop & Glo Reagent was added to each well and renilla luciferase activity was measured. pNFκB-Luc activity was normalized to pRL-CMV.

IL-1 Induced Cytokine Production Assay

NIH-3T3 cells were cultured in DMEM supplemented with 10% FBS in 6-well culture dish at a density of $0.5 \times 10^6$ cells/well. Cells were transfected with 50 nM of AON PS-300LNA as described previously. After 16 hours the cells were stimulated with 1 ng/ml mouse IL-1β for 4-5 hours. Then total RNA isolation and cDNA synthesis were performed as described before. The IL-1 mediated induction of cytokines such as IL-6 and ICAM-1 was determined by performing qPCR assay as previously described by using the following primer sets; mouse IL-6 forward primer CCGGAGAGGAGACTTCACAG, IL-6 reverse primer TCCACGATTTCCCAGAGAAC; mouse ICAM-1 forward primer GGCATTGTTCTCTAATGTCTCCG, ICAM-1 reverse primer GCTCCAGGTATATCCGAGCTTC. All the data was normalized to the expression of house-keeping gene beta-actin; mouse beta-actin forward primer ACTGGGACGACATGGAGAAG, reverse primer GGTCATCTTTTCACGGTTGG. These primers were identified in the sequence listing by SEQ ID NO:66-71

Example 1

Skipping Exon 17 of the C5a Protein or Skipping Exon 9 of the sIL-1RAcP Protein for Treating an Inflammatory Disease Skipping Exon 17 of the C5a Protein for Treating an Inflammatory Disease The purpose is decreasing the amount of C5a while keeping C5b intact. C5 is produced by liver so the target organ for C5 specific AONs is the liver.

Mouse C5 exon 17 has been chosen as the target exon. It encodes the anaphylatoxin domain of C5a. After IV or IP injections, the majority of the AONs goes to the liver and is easily taken up by liver cells. There, they hybridize to their target RNA without causing degradation of the target by RNase H. Upon binding to exon 17, this exon cannot be recognized by the splicing machinery and will be removed with the flanking introns while keeping the open reading frame intact. The resulting truncated protein, C5Δ17, will be converted by C5 convertase into C5b which still can be incorporated into MAC and the remaining, small, non-functional portion of C5a will probably be degraded. A functional assay has been designed and being performed to reveal if functional C5b molecule can be produced or not.

AONs to cover different ESE binding sites or 5'-3' splice sites have been designed (FIG. 1) and tested (Table 1) and the results are shown in FIG. 2. We designed AONs which cover all the possible sites on the exon (and flanking introns) that can be used in the skipping of exon 17 and selected the efficient ones to be further tested by qPCR analysis. In order to increase skipping efficiencies of selected AONs, their length was extended to 25mers or a restricted number of 5-6 LNA modifications were added. Whether that resulted in enhanced hybridization characteristics was tested in-vitro. (FIG. 8 31-55).

TABLE 1

List of AONs for C5

| Name of AON | Target gene | Target exon | Chemistry | Successful in skipping |
|---|---|---|---|---|
| PS-295 | mC5 | Exon 17 | 2'O-methyl PS | + |
| PS-296 | mC5 | Exon 17 | 2'O-methyl PS | + |
| PS-329 | mC5 | Exon 17 | 2'O-methyl PS | + |
| PS-330 | mC5 | Exon 17 | 2'O-methyl PS | + |
| PS-348 | mC5 | Exon 17 | 2'O-methyl PS | +− |
| PS-349 | mC5 | Exon 17 | 2'O-methyl PS | +− |
| PS-350 | mC5 | Exon 17 | 2'O-methyl PS | +− |
| PS-351 | mC5 | Exon 17 | 2'O-methyl PS | +− |
| PS-352 | mC5 | Exon 17 | 2'O-methyl PS | − |
| PS-353 | mC5 | Exon 17 | 2'O-methyl PS | + |
| PS-354 | mC5 | Exon 17 | 2'O-methyl PS | + |

TABLE 1-continued

List of AONs for C5

| Name of AON | Target gene | Target exon | Chemistry | Successful in skipping |
|---|---|---|---|---|
| PS-377 | hC5 | Exon 17 | 2'O-methyl PS | + |
| PS-378 | hC5 | Exon 17 | 2'O-methyl PS | + |
| PS-379 | hC5 | Exon 17 | 2'O-methyl PS | + |
| PS-329-25mer | mC5 | Exon 17 | 2'O-methyl PS | + |
| PS-329-LNA | mC5 | Exon 17 | 2'O-methyl + LNA PS | + |

Skipping Exon 9 of the sIL-1RAcP Protein for Treating an Inflammatory Disease

The purpose is to increase the amount of soluble IL-1RAcP by shifting the membrane bound form of it into soluble form. It is produced by liver so the target organ for the soluble IL-1RAcP specific AONs is the liver.

Mouse IL-1RAcP exon 9 has been chosen as the target exon because it encodes the transmembrane domain of IL-1RAcP. Since skipping of exon 9 does not disturb the open reading frame we propose that the soluble form, called IL-1RAcPΔ9, can be obtained. After IV or IP injections, AONs go to the liver and will easily be taken up by liver cells. There, they hybridize to their target RNA without causing degradation of the target by RNase H. Upon binding to exon 9, this exon can not be recognized by the splicing machinery and will be removed with the flanking introns.

Figure 3:
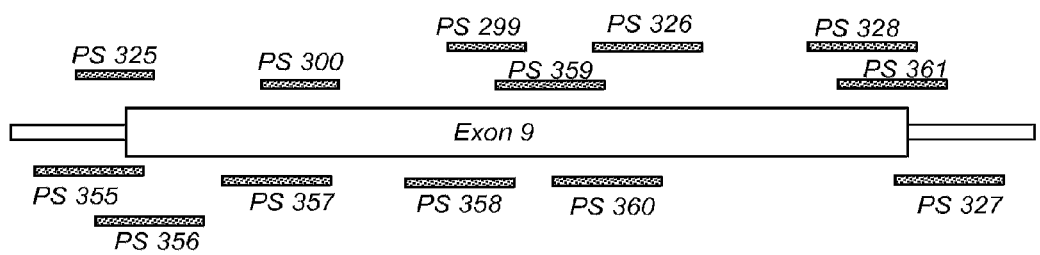
Figure 4:
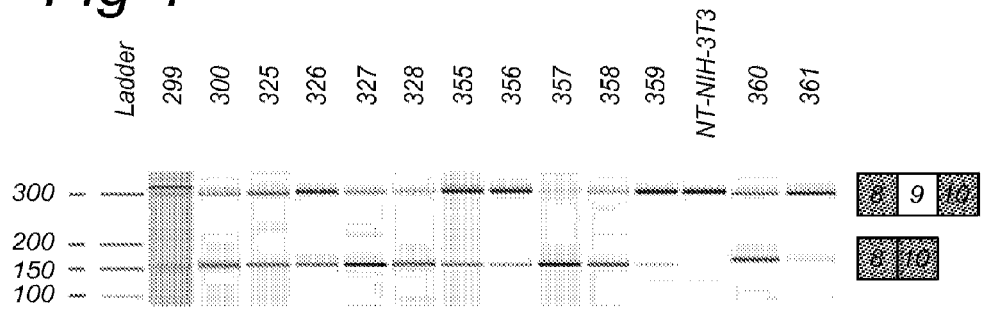
FIG. 4. NIH/3T3 cells were transfected with indicated AONs at a final concentration of 500 nM. After 24 hours RNA was isolated for exon-skiping and analyzed by RT-PCR.
Figure 5:
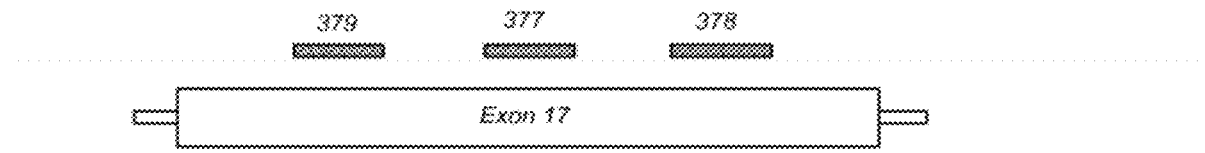
FIG. 5: AONs targeting human C5 pre-mRNA exon 17.
Figure 6:
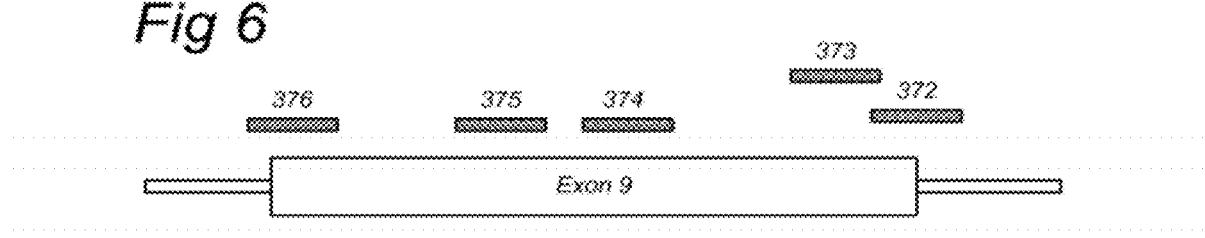
FIG. 6: AONs targeting human IL-1RAcP pre-mRNA exon 9 with flanking introns
Figure 8:
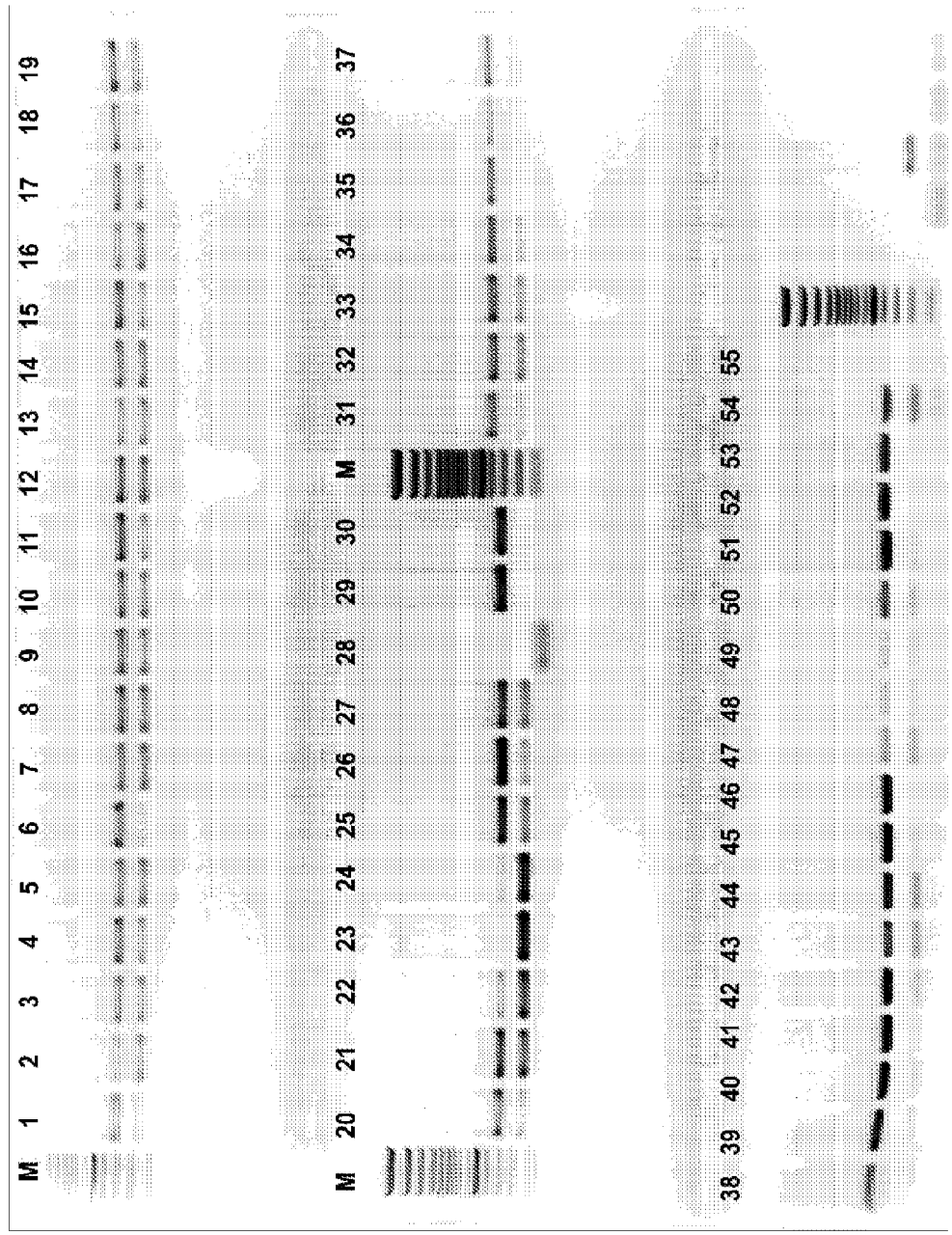
FIG. 8:
1-30; RT-PCR results of NIH-3T3 cells treated with different AONs in different concentrations for IL-1RAcP exon 9 skipping.
1: 300-21 mer 20 nM
2: 300-21 mer 50 nM
3: 300-21 mer 100 nM
4: 300-21 mer 200 nM
5: 300-21 mer 500 nM
6: 300-25 mer 20 nM
7: 300-25 mer 50 nM
8: 300-25 mer 100 nM
9: 300-25 mer 200 nM
10: 300-25 mer 500 nM
11: 327-21 mer 20 nM
12: 327-21 mer 50 nM
13: 327-21 mer 100 nM
14: 327-21 mer 200 nM
15: 327-21 mer 500 nM
16: 327-25 mer 20 nM
17: 327-25 mer 50 nM
18: 327-25 mer 100 nM
19: 327-25 mer 200 nM
20: 327-25 mer 500 nM
21: 300-LNA 10 nM
22: 300-LNA 20 nM
23: 300-LNA 50 nM
24: 300-LNA 100 nM
25: 300-LNA 200 nM
26: 300-LNA 500 nM
27: positive control
28: negative control
29: Non-transfected
30: Mock-transfected
M Marker
31-55; RT-PCR results of L929 cells treated with different AONs in different
concentrations for C5 exon 17 skipping.
31: 329-21 mer 20 nM
32: 329-21 mer 50 nM
33: 329-21 mer 100 nM
34: 329-21 mer 200 nM
35: 329-21 mer 500 nM
36: 329-25 mer 20 nM
37: 329-25 mer 50 nM
38: 329-25 mer 100 nM
39: 329-25 mer 200 nM
40: 329-25 mer 500 nM
41: 329-LNA 10 nM
42: 329-LNA 20 nM
43: 329-LNA 50 nM
44: 329-LNA 100 nM
45: 329-LNA 200 nM
46: 329-LNA 500 nM
47: 354-25 mer 20 nM
48: 354-25 mer 50 nM
49: 354-25 mer 100 nM
50: 354-25 mer 200 nM
51: 354-25 mer 500 nM
52: Non-transfected
53: Mock-transfected
54: positive control
55: negative control
Figure 9:
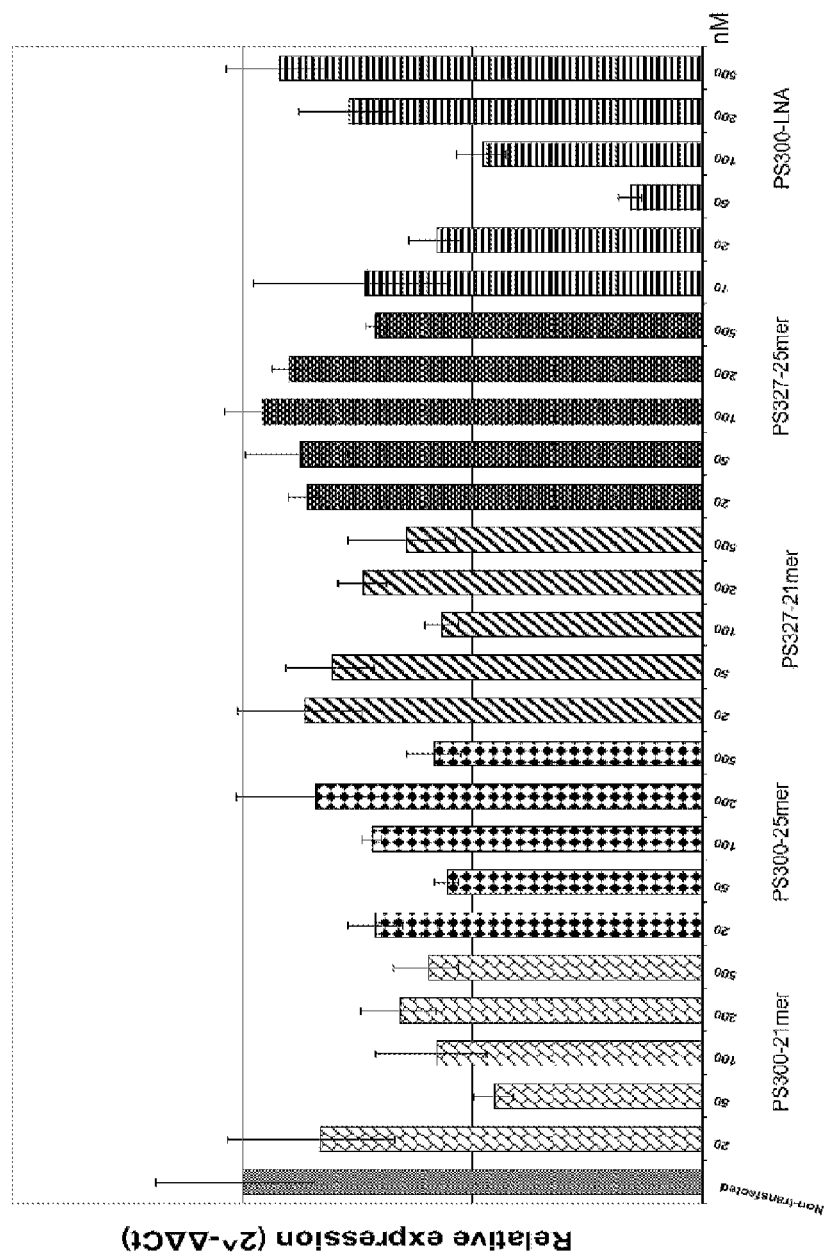
FIG. 9: Comparison of skipping efficiencies of different AONs for IL-1RAcP in different concentrations with qPCR.

AONs to cover different ESE binding sites or 5'-3' splice sites have been designed (FIG. 3) and tested. (Table 2) and the results are shown in FIG. 4. We designed AONs which cover all the possible sites on the exon (and flanking introns) that can be used in the skipping of exon 9 and selected the efficient ones to be further tested by qPCR analysis. In order to increase skipping efficiencies of selected AONs, their length was extended to 25mers or a restricted number of 5 LNA modifications were added. Whether that resulted in enhanced hybridization characteristics was tested in-vitro. The results are shown in FIG. 8 (1-31). Skipping efficiencies of different AONs in different concentrations were also compared with qPCR. (FIG. 9).

TABLE 2

List of AONs for IL-1RAcP

| | | | | |
|---|---|---|---|---|
| PS-299 | mIL-1RAcP | Exon 9 | 2'O-methyl PS | + |
| PS-300 | mIL-1RAcP | Exon 9 | 2'O-methyl PS | + |
| PS-325 | mIL-1RAcP | Exon 9 | 2'O-methyl PS | + |
| PS-326 | mIL-1RAcP | Exon 9 | 2'O-methyl PS | + |
| PS-327 | mIL-1RAcP | Exon 9 | 2'O-methyl PS | + |
| PS-328 | mIL-1RAcP | Exon 9 | 2'O-methyl PS | +− |
| PS-355 | mIL-1RAcP | Exon 9 | 2'O-methyl PS | + |
| PS-356 | mIL-1RAcP | Exon 9 | 2'O-methyl PS | + |
| PS-357 | mIL-1RAcP | Exon 9 | 2'O-methyl PS | + |
| PS-358 | mIL-1RAcP | Exon 9 | 2'O-methyl PS | + |
| PS-359 | mIL-1RAcP | Exon 9 | 2'O-methyl PS | +− |
| PS-360 | mIL-1RAcP | Exon 9 | 2'O-methyl PS | + |
| PS-361 | mIL-1RAcP | Exon 9 | 2'O-methyl PS | +− |
| PS-372 | hIL-1RAcP | Exon 9 | 2'O-methyl PS | + |
| PS-373 | hIL-1RAcP | Exon 9 | 2'O-methyl PS | + |
| PS-374 | hIL-1RAcP | Exon 9 | 2'O-methyl PS | +− |
| PS-375 | hIL-1RAcP | Exon 9 | 2'O-methyl PS | − |
| PS-376 | hIL-1RAcP | Exon 9 | 2'O-methyl PS | +− |
| PS-300LNA | mIL-1RAcP | Exon 9 | 2'O-methyl + LNA PS | ++ |
| PS-300-25mer | mIL-1RAcP | Exon 9 | 2'O-methyl PS | + |
| PS-327-25mer | mIL-1RAcP | Exon 9 | 2'O-methyl PS | + |

Example 2

Confirmation of the Functionality of the Oligonucleotides in a Cell Line

Results:

C5 Exon-17 Skipping

Figure 2:
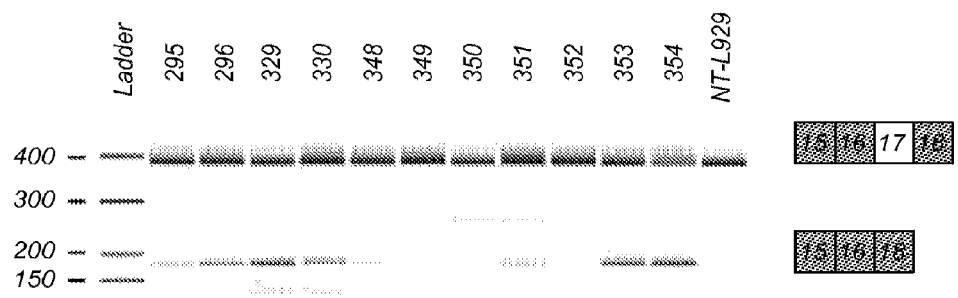
FIG. 2. L929 cells were transfected with indicated AONs at a final concentration of 500 nM. After 24 hours RNA was isolated for exon-skiping and analyzed by RT-PCR FIG. 3. AONs targeting mouse IL-1RAcP pre-mRNA exon 9 with flanking introns.
Figure 7:
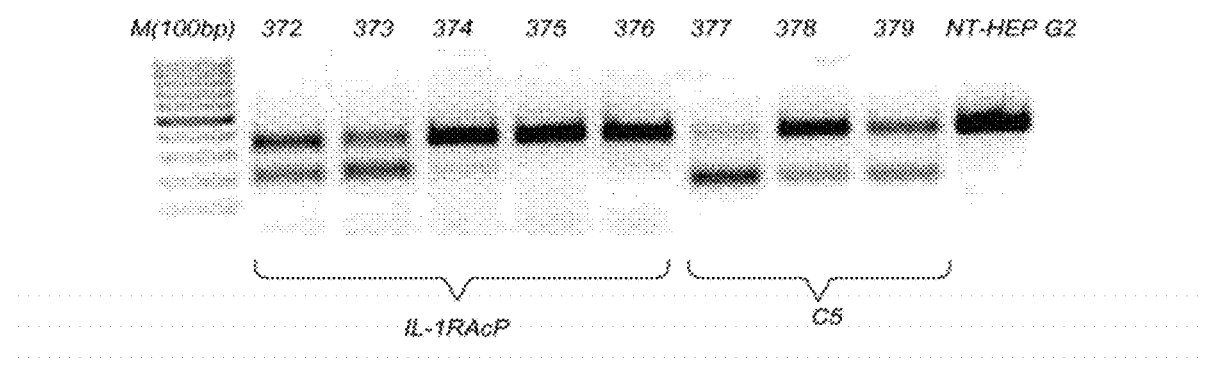
FIG. 7: HEP-G2 cells were transfected with indicated AONs at a final concentration of 500 nM. After 24 hours RNA was isolated for exon-skiping and analyzed by RT-PCR.

To decrease the level of C5a, a series of AONs have been designed targeting murine or human exon-17 (see example 1). They were screened in L929 and HepG2 cell lines, respectively. The cell lines were transfected with AON in Lipofectamine 2000 and the average transfection efficiencies were determined by using fluorescent AON. From the screen of 11 AONs for murine and 3 AONs for human target exons, AONs PS329 and PS377 have been selected as the most successful AONs in skipping exon 17. The effective AONs were expected to produce shorter transcript fragments with sizes around 178 bp and 155 bp for murine and human targets, respectively (FIGS. 2&7). The sequence analysis also showed that the shorter fragments were lacking exon 17. The AONs PS-329, 329-25mer, 354, 329-LNA were tested extensively in different concentration to compare efficiencies in skipping. PS-329-LNA was a bit more effective than the others based on a comparison of the densities of the band in agarose gel of the shorter fragments (FIG. 8 31-55). AON PS-329 was also tested and found functional in-vivo in a pilot experiment. 100 mg/kg AON was injected IV for 3 or 4 days and liver samples were analyzed with RT-PCR to detect exon skipping. The skipped product has the correct size and sequence analysis confirmed that it was the correct product.

IL-1RAcP Exon-9 Skipping

Figure 10A:
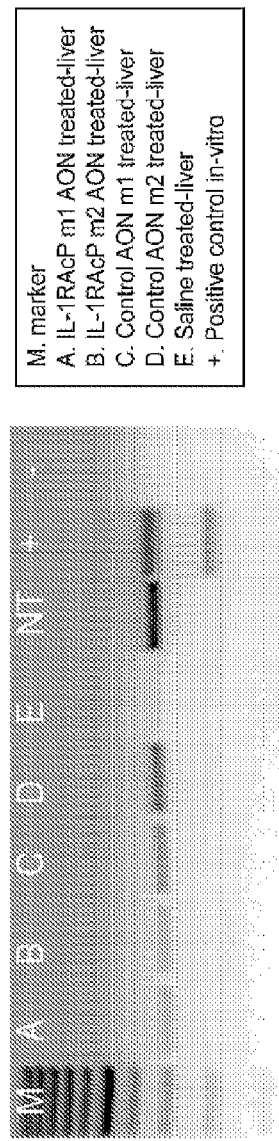
FIG. 10: RT-PCR results of liver samples treated with different amount of AON PS-300 and sequencing results.
  a) 50 mg/kg IP for 8 days for IL-1RAcP AON. Sacrificed on post-injection Day 1
  b) 100 mg/kg IV for 4 or 3 days. Sacrificed on post-injection Day 1
  c) sequence analysis of the lower band.
Figure 10B:
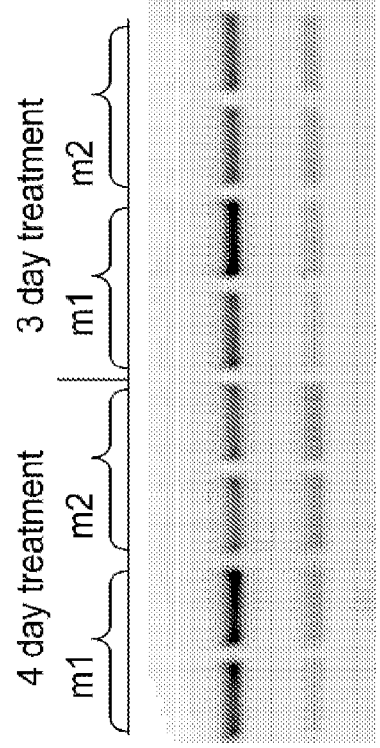
Figure 10C:
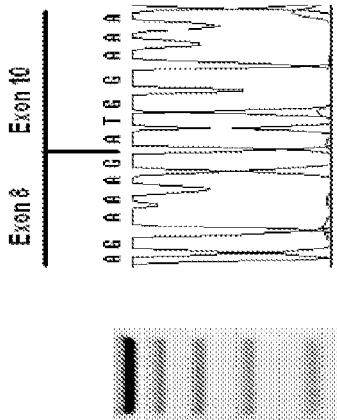
Figure 11C:
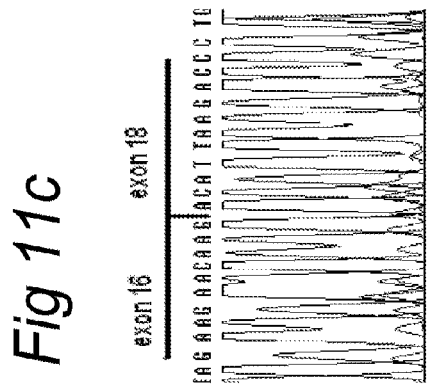
FIG. 11: RT-PCR results of liver samples treated with different amount of AON PS-329 and sequencing results.
  a) IV injection C5-AON for 4 days 100 mg/kg Sacrf. Post-injection Day 1, Control AON (4 days 50 mg/kg)
  b) IV C5 AON for 3 days with 100 mg/kg AON.
  m1 Sacrf. Post-injection Day 1
  m2 Sacrf. Post-injection Day 5
  c) Sequencing results
Figure 11A:
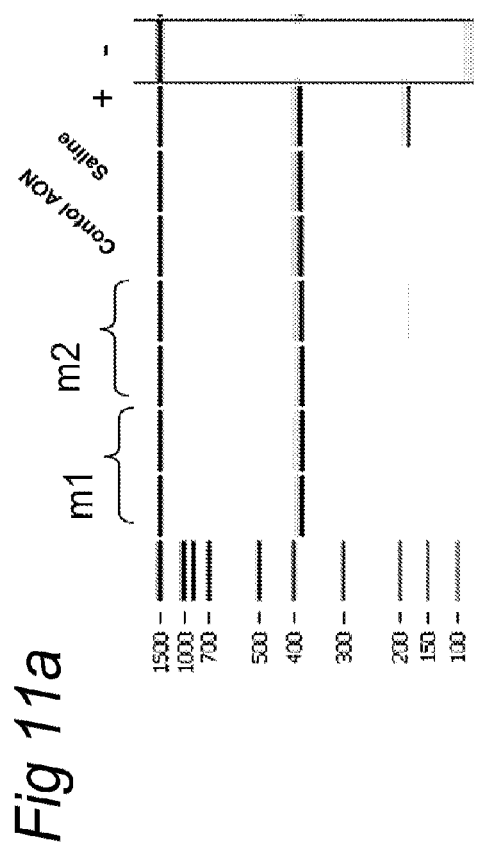
Figure 11B:
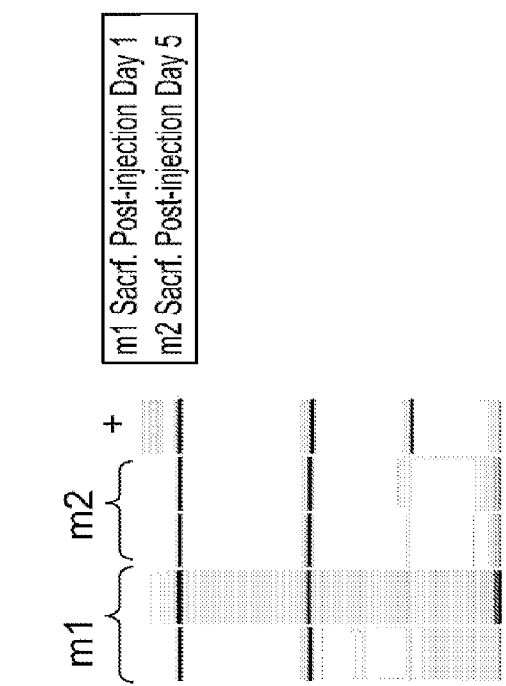

To induce soluble IL-1RAcP production (IL-1RAcPΔ9), a series of AONs have been designed targeting murine and human exon-9 (see example 2). They were screened in NIH-3T3 and HepG2 cell lines, respectively. The cell lines were transfected with AON in Lipofectamine 2000 and the average transfection efficiencies were determined by using fluorescent AON. From the screen of 13 AONs for murine and 5 AONs for human target exons, AONs PS300 and PS373 have been selected as the most successful AONs in skipping exon 9. The effective AONs were expected to produce shorter transcript fragments with sizes around 150 bp and 200 bp for murine and human targets, respectively (FIGS. 4&7). The sequence analysis also showed that the shorter fragments are lacking exon 9. The AONs PS-300, 300-25mer, 300-LNA, 327 and 327-25mer were tested extensively in different concentration to compare skipping efficiencies. PS-300-LNA was far more effective in skipping (around 85%) than the other AONs especially in the concentration of 50 nM (FIG. 8 1-31). The results were also confirmed by qPCR analysis (FIG. 9). AON PS-300 was also tested in-vivo in a pilot experiment. 50-100 mg/kg AON was injected IP or IV for 3 or 4 days and liver samples were analyzed for exon skipping with RT-PCR. There was skipped product with correct size which was confirmed by sequence analysis. In-vivo skipping efficiency was comparable with the in-vitro skipping efficiency (FIG. 10).

Example 3

Other Ways of Testing the Functionality of the Oligonucleotides of the Invention The efficacy of the oligonucleotides of the invention may also be tested at the protein level by quantifying sIL-1RAcP, IL-1, C5a or C5b by Western blotting for example: an increase of soluble sIL-1RAcP and/or a decrease of free IL-1 and/or a decrease of C5a. The efficacy of the oligonucleotides of the invention may also be tested by functional assays for Il-1RAcP by assessing the presence or the level of activity of molecules or pathways induced or activated by IL-1. Il-1 induces NF-κB activation. Therefore, the efficacy of the oligonucleotides of the invention may also be tested by assessing the activation of NF-Kb: decrease of NF-Kb activation.

IL-1 induces production of some chemokines and pro-inflammatory cytokines from the cells such as IL-6 or ICAM-1. Therefore, the efficacy of the oligonucleotides of the invention may also be tested by assessing the presence of IL-6 or ICAM-1: decrease of IL-6 and/or ICAM-1.

The efficacy of the oligonucleotides of the invention may also be tested by a functional assay for C5 such as a hemolytic assay as described in Van Dijk H. Et al, (1980), J. Immunol. Meth. 39: 257-268.

TABLE 3 list of all AONs tested

| AON | sequence (5'-3') |
|---|---|
| mIL-1RAcP | |
| PS299 | CUCCAGCCAGUAAACAUGGUAA SEQ ID NO: 25 |
| PS300 | AAAACCACAGGCGAGUUCUAC SEQ ID NO: 26 |
| PS325 | AUGACUACAGCAAAUGACAA SEQ ID NO: 27 |
| PS 326 | CCAAAGUGAGCUCGGUAAAAG SEQ ID NO: 28 |
| PS 327 | GCACACUUCCAAUACUUACC SEQ ID NO: 29 |
| PS 328 | UACUUACCAAGAAUUGU SEQ ID NO: 30 |
| PS355 | GGUAUGACUACAGCAAAUGACAAA SEQ ID NO: 31 |
| PS356 | GUACCUUGGUGGUAUGACUACAGCA SEQ ID NO: 32 |
| PS357 | AAAACCACAGGCGAGUUCUACUGUG SEQ ID NO: 33 |
| PS358 | CAGUAAACAUGGUAAACCACAAUGA SEQ ID NO: 34 |
| PS359 | AAGAGGACCAUCUCCAGCCAGUAAA SEQ ID NO: 35 |
| PS360 | CAAAGUGAGCUCGGUAAAAGAGGAC SEQ ID NO: 36 |
| PS361 | AGCACACUUCCAAUACUUACCAAGA SEQ ID NO: 37 |
| mC5 | |
| PS295 | CAGGUUUCGUAGAAGUUCACUCGG SEQ ID NO: 11 |
| PS296 | ACAGCACUCGUUGAAGGCCC SEQ ID NO: 12 |
| PS329 | ACUUACGGAUCCUUCCCAGUU SEQ ID NO: 13 |
| PS 330 | GGAAAACUCAUACUUACGGA SEQ ID NO: 14 |
| PS348 | GUACUUAGCAGCUGAAAUGGUGGCA SEQ ID NO: 15 |
| PS349 | CUCGGGCUCCGUCAUAGCAGCAUUU SEQ ID NO: 16 |
| PS350 | CACAGGUUUCGUAGAAGUUCACUCG SEQ ID NO: 17 |
| PS351 | GGUAACCCGGGCCACUCGCUCCUCA SEQ ID NO: 18 |
| PS352 | CUCGUUGAAGGCCCUGAUGCAGAGA SEQ ID NO: 19 |
| PS353 | CCUUCCCAGUUGGACAGGUUUAUGG SEQ ID NO: 20 |
| PS354 | AAACUCAUACUUACGGAUCCUUCCC SEQ ID NO: 21 |

TABLE 3-continued list of all AONs tested

| AON | sequence (5'-3') |
|---|---|
| h IL-RAcP | |
| 372 | UGUUACUUACCUAAAAUGGUUUC SEQ ID NO: 38 |
| 373 | UUUCAUCUGUUCCAAAAUGAG SEQ ID NO: 39 |
| 374 | UAGCCAGUAAACAUGGUAAACAA SEQ ID NO: 40 |
| 375 | AGAAUCACCACUAGCAGGACUGU SEQ ID NO: 41 |
| 376 | UCUUGGAGCUGGCACUGGAAU SEQ ID NO: 42 |
| hC5 | |
| 377 | GCUCGCUGCUCACAGGUUUCA SEQ ID NO: 22 |
| 378 | ACACAACAUUCAGUGAAAGCUUU SEQ ID NO: 23 |
| 379 | CAGGCUCCAUCGUAACAACAU SEQ ID NO: 24 |

TABLE 4 list of preferred AON

| AON | sequence (5'-3') |
|---|---|
| mIL-1RAcP | |
| PS300 | AAAACCACAGGCGAGUUCUAC |
| mC5 | |
| PS329 | ACUUACGGAUCCUUCCCAGUU |
| h IL-RAcP | |
| 373 | UUUCAUCUGUUCCAAAAUGAG |
| hC5 | |
| 377 | GCUCGCUGCUCACAGGUUUCA |

TABLE 5 identification of the regions targeted by each oligonucleotide used

| AON | region |
|---|---|
| mIL-1RAcP | |
| PS299 | exon 9 |
| PS300 | exon 9 |
| PS 325 | intron8-exon9 |
| PS 326 | exon 9 |
| PS 327 | exon9-intron 9 |
| PS 328 | exon9-intron 9 |
| PS355 | intron8-exon9 |
| PS356 | intron8-exon9 |
| PS357 | exon 9 |
| PS358 | exon 9 |
| PS359 | exon 9 |
| PS360 | exon 9 |
| PS361 | exon9-intron 9 |
| mC5 | |
| PS295 | exon 17 |
| PS296 | exon 17 |
| PS329 | exon 17-intron 17 |
| PS 330 | exon 17-intron 17 |

TABLE 5-continued identification of the regions targeted by each oligonucleotide used

| AON | region |
|---|---|
| PS348 | intron 16-exon17 |
| PS349 | exon 17 |
| PS350 | exon 17 |
| PS351 | exon 17 |
| PS352 | exon 17 |
| PS353 | exon 17 |
| PS354 | exon 17-intron 17 |
| h IL-RAcP | |
| 372 | exon 9-intron 9 |
| 373 | exon 9 |
| 374 | exon 9 |
| 375 | exon 9 |
| 376 | intron 8-exon 9 |
| hC5 | |
| 377 | exon 17 |
| 378 | exon 17 |
| 379 | exon 17 |

REFERENCES

1. Role of C5a in Inflammatory Respons, Annu. Rev. Immunol. 23:821-52 (2005)
2. Structure of the Murine FifthC omplement Component (C5) Gene 266, 11818-11825 (1991)
3. Essential Role for the C5a Receptor in Regulating the Effector Phase of Synovial Infiltration and Joint Destruction in Experimental Arthritis, J. Exp. Med. 196, 1461-1471 (2002).
4. Rheumatoid arthritis and the complement system, Annals of Medicine, 39, 517-530 (2007)
5. Anti-05 monoclonal antibody therapy prevents collagen-induced arthritis and ameliorates established disease, Proc. Natl. Acad. Sci. USA, 92, 8955-8959, (1995)
6. Pre-neutralization of C5a-mediated effects by the monoclonal antibody 137-26 reacting with the C5a moiety of native C5 without preventing C5 cleavage, Clin Exp Immunol., 160-169 (2003)
7. Pathways for Interleukin-1-Driven Arthritis, Arthritis & Rheumatism, 58, 3283-3285 (2008)
8. The Soluble Form of IL-1 Receptor Accessory Protein Enhances the Ability of Soluble Type II IL-1 Receptor to Inhibit IL-1 Action, Immunity, 18, 87-96 (2003).
9. Soluble Interleukin-1 Receptor Accessory Protein Ameliorates Collagen-Induced Arthritis by a Different Mode of Action From That of Interleukin-1 Receptor Antagonist, Arthritis & Rheum. 52, 2202-2211 (2005)
10. Dorn and Kippenberger, Curr Opin Mol Ther 2008 10(1) 10-20
11. Cheng and Van Dyke, Gene. 1997 Sep. 15; 197(1-2):253-60
12. Macaya et al., Biochemistry. 1995 4; 34(13):4478-92.
13. Suzuki et al., Eur J. Biochem. 1999, 260(3):855-6
14. Mathews D H, Sabina J, Zuker M, Turner D H. Expanded sequence dependence of thermodynamic parameters improves prediction of RNA secondary structure. J Mol Biol 1999; 288(5):911-40.
15. Cartegni L, Chew S L, Krainer A R. Listening to silence and understanding nonsense: exonic mutations that affect splicing. Nat Rev Genet 2002; 3(4):285-98.
16. Cartegni L, Wang J, Zhu Z, Zhang M Q, Krainer A R. ESEfinder: A web resource to identify exonic splicing enhancers. Nucleic Acids Res 2003; 31(13):3568-71.
17. Braasch D A, Corey D R. Locked nucleic acid (LNA): fine-tuning the recognition of DNA and RNA. Chem Biol 2001; 8(1):1-7.
18. Braasch D A, Corey D R. Novel antisense and peptide nucleic acid strategies for controlling gene expression. Biochemistry 2002; 41(14):4503-10.
19. Elayadi A N, Corey D R. Application of PNA and LNA oligomers to chemotherapy. Curr Opin Investig Drugs 2001; 2(4):558-61.
20. Larsen H J, Bentin T, Nielsen P E. Antisense properties of peptide nucleic acid. Biochim Biophys Acta 1999; 1489 (1):159-66.
21. Summerton J. Morpholino antisense oligomers: the case for an RNase H-independent structural type. Biochim Biophys Acta 1999; 1489(1):141-58.
22. Summerton J, Weller D. Morpholino antisense oligomers: design, preparation, and properties. Antisense Nucleic Acid Drug Dev 1997; 7(3):187-95.
23. Wahlestedt C, Salmi P, Good L, et al. Potent and nontoxic antisense oligonucleotides containing locked nucleic acids. Proc Natl Acad Sci USA 2000; 97(10):5633-8.
24. Goyenvalle A, Vulin A, Fougerousse F, et al. Rescue of dystrophic muscle through U7 snRNA-mediated exon skipping. Science 2004; 306(5702):1796-9.
25. De Angelis F G, Sthandier O, Berarducci B, et al Chimeric snRNA molecules carrying antisense sequences against the splice junctions of exon 51 of the dystrophin pre-mRNA induce exon skipping and restoration of a dystrophin synthesis in Delta 48-50 DMD cells. Proc Natl Acad Sci USA 2002; 99(14):9456-61.
26. Denti M A, Rosa A, D'Antona G, et al Chimeric adeno-associated virus/antisense U1 small nuclear RNA effectively rescues dystrophin synthesis and muscle function by local treatment of mdx mice. Hum Gene Ther 2006; 17(5): 565-74.
27. Gorman L, Suter D, Emerick V, Schumperli D, Kole R. Stable alteration of pre-mRNA splicing patterns by modified U7 small nuclear RNAs. Proc Natl Acad Sci USA 1998; 95(9):4929-34.
28. Suter D, Tomasini R, Reber U, Gorman L, Kole R, Schumperli D. Double-target antisense U7 snRNAs promote efficient skipping of an aberrant exon in three human beta-thalassemic mutations. Hum Mol Genet 1999; 8(13): 2415-23.
29. Jensen L, Muzio M, Mantovani A, Whitehead A, IL-1 signalling cascade in liver cells and the involvement of a soluble form of the IL-1 receptor accessory protein. Journal of Immunology, 2000, 164 5277-5286.

The invention claimed is:

1. An oligonucleotide which alters the splicing of a pre-mRNA encoding IL-1RAcP, wherein said oligonucleotide binds a part of exon 9 in the pre-mRNA encoding IL-1RAcP, wherein exon 9 comprises SEQ ID NO: 5 or 6, said oligonucleotide comprising a modification selected from the group consisting of: a modification to increase resistance to RNAseH within a cell, a backbone modification and/or a sugar modification.

2. An oligonucleotide according to claim 1, wherein said oligonucleotide induces the skipping of exon 9 in the pre-mRNA encoding IL-1 RAcP.

3. An oligonucleotide according to claim 2, wherein said oligonucleotide inhibits the inclusion of exon 9 in of the pre-mRNA encoding IL-1 RAcP.

4. An oligonucleotide according to claim 1, wherein said oligonucleotide comprises a sequence which binds to at least a part of exon 9 in the pre-mRNA encoding IL-1RAcP wherein said part of exon 9 is a contiguous stretch comprising at least 8 nucleotides and wherein said oligonucleotide also binds to at least a part of a non-exon region of the pre-mRNA encoding IL-1RAcP wherein said part of the non-exon region is a contiguous stretch comprising at least 8 nucleotides.

5. An oligonucleotide according to claim 1, wherein said oligonucleotide comprises a sequence which also binds a splice site or an intronic sequence of the pre-mRNA encoding IL-1RAcP.

6. An oligonucleotide according to claim 4, wherein the contiguous stretch of exon 9 and/or the contiguous stretch of non-exon region comprises 8-50 nucleotides of exon 9 in the pre-mRNA encoding IL-1RAcP.

7. An oligonucleotide according to claim 1, wherein said oligonucleotide comprises or consists of a sequence selected from the group consisting of: SEQ ID NOS: 25-41.

8. An oligonucleotide according to claim 1, wherein the oligonucleotide has a modified backbone and a modified sugar moiety wherein the oligonucleotide comprises one or more 2'-O-methyl riboses and one or more phosphorothioate internucleoside linkages.

9. An oligonucleotide according to claim 8, wherein the oligonucleotide comprises a 2'-O-methyl phosphorothioate internucleoside linkage and a locked nucleic acid monomer.

10. An oligonucleotide according to claim 1, wherein said oligonucleotide comprises at least one inosine and/or a base able to form a wobble base pair.

11. A method for preventing or treating an inflammatory disorder in an individual, the method comprising administering to said individual an effective amount of an oligonucleotide wherein said oligonucleotide alters the splicing of a pre-mRNA encoding IL-1RAcP, binds a part of exon 9 of the IL-1RAcP pre-mRNA, wherein exon 9 comprises SEQ ID NO: 5 or 6, said oligonucleotide comprising a modification selected from the group consisting of: a modification to increase resistance to RNAseH within a cell, a backbone modification, and/or a sugar modification.

12. The method of claim 11, wherein said disorder comprises rheumatoid arthritis (RA), juvenile rheumatoid arthritis, psoriasis, psoriatic arthritis, ankylosing spondylitis, inflammatory bowel disease including Crohn's disease or ulcerative colitis, hepatitis, sepsis, alcoholic liver disease, or non-alcoholic steatosis.

13. A composition comprising the oligonucleotide of claim 1.

14. A composition according to claim 13, further comprising a second oligonucleotide, wherein said second oligonucleotide alters the splicing of a pre-mRNA encoding C5 in order to decrease the amount of a C5a.

15. An oligonucleotide according to claim 6, wherein the contiguous stretch comprises 14-25 nucleotides of exon 9 in of the pre-mRNA encoding IL-1 RAcP.

16. A composition according to claim 13, wherein the composition is a pharmaceutical composition, said pharmaceutical composition comprising a pharmaceutically acceptable carrier, adjuvant, diluent and/or excipient.

17. An oligonucleotide which alters the splicing of a pre-mRNA encoding IL-1RAcP, wherein said oligonucleotide binds a part of a non-exon region of the pre-mRNA encoding IL-1RAcP, wherein exon 9 in the pre-mRNA encoding IL-1RAcP comprises SEQ ID NO: 5 or 6; wherein said oligonucleotide induces the skipping of exon 9 in the pre-mRNA encoding IL-1RAcP, and wherein said oligonucleotide comprises a modification selected from the group consisting of: a modification to increase resistance to RNAseH within a cell, a backbone modification and/or a sugar modification.

18. The oligonucleotide of claim 1, wherein the modification to increase resistance to RNAseH within a cell is selected from the group consisting of: a backbone modification, a sugar modification, and a base modification.

19. The oligonucleotide of claim 18, wherein the backbone modification is selected from the group consisting of: a phosphorodithioate internucleoside linkage, a phosphorothioate internucleoside linkage, a chirally pure phosphorothioate internucleoside linkage, a methyl phosphonate internucleoside linkage, and a H-phosphonate internucleoside linkage.

20. The oligonucleotide of claim 18, wherein the sugar modification is selected from the group consisting of: 2'-halide, 2'-O-alkyl, 2'-O-methyl, 2'-F, 2'-O-(2-methoxy)ethyl, 2'-O-ethyl, 2'-O-allyl, 2'-O-butyryl, 2'-O-propargyl, 2'-O-(2-amino)ethyl, a locked nucleic acid monomer, and an ethylene-bridged nucleic acid monomer.

21. The oligonucleotide of claim 18, wherein the base modification is selected from the group consisting of: 5-halogenated uracil, 5-halogenated cytosine, 5-aminomethyl-uracil, 2,6-diaminopurine, 5-propargyl-cytosine, 5-propargyl-uracil, G-clamp and its derivatives, 5-methyl-cytosine and 5-methyl-uracil.

22. The oligonucleotide of claim 18, wherein the modification to increase resistance to RNAseH comprises a 2'-O-methyl sugar modification and a phosphorothioate internucleoside linkage backbone modification.

23. The oligonucleotide of claim 18, wherein the modification to increase resistance to RNAse H comprises a 2'-O-methyl sugar modification, a phosphorothioate internucleoside linkage backbone modification and/or a locked nucleic acid monomer sugar modification.

* * * * *

SEQUENCE LISTING

<160> NUMBER OF SEQ ID NOS: 71

<210> SEQ ID NO 1
<211> LENGTH: 198
<212> TYPE: RNA

```
<213> ORGANISM: artificial
<220> FEATURE:
<223> OTHER INFORMATION: murine exon 17 C5

<400> SEQUENCE: 1
cugcuaagua caaacauagu gugccaaaga aaugcugcua ugacggagcc cgagugaacu     60
ucuacgaaac cugugaggag cgaguggccc gguuaccau aggcccucuc ugcaucaggg    120
ccuucaacga gugcuguacu auugcgaaca agauccgaaa agaaagcccc cauaaaccug    180
uccaacuggg aaggaucc                                                  198

<210> SEQ ID NO 2
<211> LENGTH: 198
<212> TYPE: RNA
<213> ORGANISM: artificial
<220> FEATURE:
<223> OTHER INFORMATION: human exon 17 C5

<400> SEQUENCE: 2
cugcuaaaua uaaacauuca guagugaaga aauguuguua cgauggagcc ugcguuaaua     60
augaugaaac cugugagcag cgagcugcac ggauuaguuu agggccaaga ugcaucaaag    120
cuuucacuga auguugcugc gucgcaagcc agcuccgugc uaauaucucu cauaaagaca    180
ugcaauuggg aaggcuac                                                  198

<210> SEQ ID NO 3
<211> LENGTH: 1396
<212> TYPE: RNA
<213> ORGANISM: artificial
<220> FEATURE:
<223> OTHER INFORMATION: murine pre-mRNA intron 17 C5

<400> SEQUENCE: 3
guaaguauga guuuccuac cagaauccua ucgauaugg gagauucuau guaaauuagu       60
gcugcuaaga aagguagcuu ugaugcuuca guuaaaaacu agaaguggaa aagagaccuc    120
aucuguaucc aaauacuucc auuguucuug gggccauugg aauggagacag ugcccagu     180 aguuugaauc cagauccagu guaacuugaa agccaacuca uccccaaagc uuagagugaug   240 guuuauccug ugagccucaa gcaggaaccu uugcuuagau aacuguauua caugcuugaa    300
cucuaaaauu cuaugugaca ucauacccgu gacaucauac cuauugaaaa ugaaguugu     360 gcuuacacug accaaaauaca gcaaaagacu ccuaaaauga gcaagucauu aaguuuacuu    420
gugacugggg gacuuauuuc aguuucagcc aacaaugug cuuuuagaau cacuuaugca     480
ucaguuuuag gaaaagaagc aaaagcgaaa uggcaucuac ccuuuucuac ucuguuugc     540 uuagcggugu aucuuaagug uugucuaucu caauggauac auucauaga cauaauggu     600 acugcaauuu aaaaaacaug cuauuaggga ucauuugcc auaacuaggu acauuaaguu    660
gccucccagu uucugcuucu ccaaguguaa uucgaugaa uaaucuagca cauauuuuu     720 ucacugccca guuuucaac uagcauccuc caguggcuu uagcuacaug guacccacca     780
ucgacggccc uuccucccug cugagucuac uccccauucu agacagcgug gccucccac     840 agucucaucu gugcagccac cagccuucag ggcuguggu agcucccgc cugaccuggu     900 cgggaguugg gacagggucag agccggcuug cuuagcucag ggaucuaggu ccauacugcu    960
aaugucuggg agucacuguu cccauagug gaaucgguu uuagguuuc ugagacucag    1020 ugguaaauuc acaguccuca uuagauaauc uagauggag cagagauucc auccaccuua    1080 uuagugugaaa uagaaauuaa caagccagaa aucacagaaa acguccaugu uuucugauau    1140
```

```
aaaucuaacu gucaaaauca caaaauuaua aauaauuuua uagacccacu gauguugugu    1200
aaaaucucag cuaucccuu gcucuuucgu caguauagga auaugcuaag gucuaaaaac    1260
ucagucauaa aaccauuaag caaugccuuc cugaccccuu uggagacag guaggucaua    1320 gaugaauggu uuuacauaaa aauucaccug aaagcagaac uaauauuggu uucuauaacu    1380
aaauauauuu cuacag                                                    1396
```

<210> SEQ ID NO 4
<211> LENGTH: 5374
<212> TYPE: RNA
<213> ORGANISM: artificial
<220> FEATURE:
<223> OTHER INFORMATION: human pre-mRNA intron 17 C5

<400> SEQUENCE: 4

```
guaaguauga cauuuucuau cagaauucug cucaauaugg ggaauuuugu guaauuuuau     60
gcugcuaaga aaggcaguuu ucaugaucua uuuagaauuu aaaguagaaa agauaacuug    120
uaaaugucca uagaaaaaaa aauccuuca uuuuugggca uccgaagagg uacaguacag    180
agcagaguac acuaggccag aguuaagacc uggcauaacc uuaaagccaa gucaucccau    240
aaacuugaau gauuauuuau ccucucugag ccucaugcaa ggagcuucga ccagauccuc    300
uccaauaugc cugugaguuc uacaagucua cgcuuuugug auauuacaac cauuaaaaau    360
ucugucuaua ucuacauuga ugaaauaaag cagaauauuu cuaaaucuag ccuaagguua    420
aguguacuua uauaaaagcu gaugucuuau uucaguuuca accacaauac auguuuccag    480
aauuuauaga acucucauua acauguuuuc agaacuuuua ggacuuuaua uauagucuuu    540
uuuuuuuuuu uuuucaguag gaaucuggcu cugucacca ggcuggagug caguggugca    600
aucuuggcuu acugcaaccu cugccucugg guucaagcga uucccugcc ucagccuccu    660 gaguaacugg gauuaaaggc gccugccacc acaccugguu aauuuuugua uuuuuaguag    720
ggacaggguu ucaccauauu ggccaggcug gucuugaacu ccugaccuca ggugauccgu    780
ccaccucggc cucccaaagu gcugagauua caggcgugag ccacugugcc cagccuaugu    840
auagucuuua acaaaacaag caaaagcaaa augacagcuu cuguuuuaua cuuaugugug    900
cugcguaaug acauuuucau caaugaugga ccacaugugc aacgugauc cuauaggauu    960 auaauaccgu auuuuucug uaccuuuccu guguuuagau augcuuagau acacaaauac   1020
uuaucauugc auuacaguug ucugcaguau ucuguucagu aacaugcugu acagguuugu   1080
agccuaggag aaauaggcua uacuauauag ucuagaucug uaguaaguua uaccaucuag   1140
auuaguguaa guacgcucca ugaugguuac acaacaaaau caucuaacaa cauauuucuc   1200
agaacauagc ccuauguuaa agcaauaucu aauaaccaua auuuugguaa auggccacaa   1260
aauuuauguu uguagaaaua uauucauuga gauguacagu gucuaagauu cagauuguuu   1320
uccaauauuu guuugcuuu guuguuugu uguuugaga gacagagauuu uguuuuugu    1380 gcccaggcug gagugcaaug gcgcagucuc agcucacugc aaccuccgcc ucccggguuc   1440
aagcaauucu ccugccucag ccucccaagu agcuggggauu acaugcaccu gccaccaugc   1500
cuggcuaaua uauuugcuu auuauaagca gaauuuuaau aaacagucua guccauaugu   1560
uguuuuucuu uuuggaggga ggauuuggcu uuuuuucuc uuaauuuuuu uuaauuuua    1620 aauuuauguuu gguaaauagu auuuacgggg uacacgagau acuuugauac aggaaugcaa   1680
uaaguaacaa ucauaucaug gaaaauggg uaucuauccc cugagguauu ucccuuugu    1740
```

```
uuuauaaaca  auccaauuau  acucuuuuag  uuauuuuuaa  auguacaauu  aaauuauuau  1800
ugacuguagu  cacccuguug  ugcugucaag  uacuaagucu  uauucauucu  uucuauuuuu  1860
uguacccaua  aaccaucccc  acaucccccu  cauccuccua  cuacccuucc  cagccuucua  1920
cucuauaucu  ccauaaguua  aauuguuuug  auuuuuagca  cccacaaaua  agugagaaca  1980
ugugaauuuu  gucuuucugu  gccugacuua  uuucacuuaa  cauaaugacc  uccaguucca  2040
uccauauugu  ugcaaaugac  aggaucucau  ucuuuucaug  gcugaguagu  acuccauugu  2100
guauaugcac  cacauuuucu  uuauccauuu  aucuguugau  ggacauuuag  guugcuucca  2160
aauccgacu  auuuuuaaca  gugcagcaac  aaacaugggc  gugcagauau  cucuucgaug  2220
uacugauuuu  cuuucuuuug  gguauauacc  cagcagugggg  auugccagau  cauaugguag  2280
cucuauucuu  uguuuuuuaa  ggaaccucca  aacuguucuc  cauaguguau  aguaauuuac  2340
auccccacu  aacaguguac  aagaguuccc  uuuucuccac  auccccucca  gcauuuguua  2400
uugccugucu  uuugaauaaa  agccauuuua  acugagauga  gaugauauuu  cauuguagcu  2460
uugauugcau  uucucuggug  auuacugaug  uugagcaccu  uuucacaugc  uuuuuugcca  2520
uuuguaaugc  ucucuuagag  aaaugucuau  ucaaaucuuu  ugcccauuuu  uaaguggau  2580
uauuacauu  uuuccuguag  aguuguuuga  acuccuauaa  uauucuuguu  auuaaucucu  2640
ugucagaugg  guagcugcaa  guauuuucuc  ccauucugua  gguugucugc  uuacuuuauu  2700
gauuccuuug  cuguacagaa  gcucuuuaac  ugaugaugau  cccauuuguc  cauuuuggcu  2760
uugguugucu  uguguguggg  guauuacuca  agaaacuuuu  gcccagacca  auguccuaga  2820
gaguuuuccc  aguguuuucc  uauagcaguu  uuauaguuag  aggucuuaga  guuaaaucuu  2880
uaaucaauuu  uuauuugagu  uuuguauaug  gcaagagaua  agggucacgu  ucauucuuc  2940
ugcaugaaug  ggauaaccag  uuuucccagc  accauuaauu  gaagagacug  uccuuccucc  3000
aauguauguu  cuuggcaccu  uugucaaaaa  ugcguucacu  auaggugugu  ggauuugcuu  3060
gggguuucua  uucuguucca  uaggucuaua  ugucugcuuu  uaugccacua  ccaugcuguu  3120
uugaauuaua  cuauaguaua  auuugaaguc  agguaaugug  auccuccag  uuuuuuucuu  3180
uuugcucggg  auugcuuugg  cuauucuggu  cuuuuguagu  uccauaugaa  uuuuaggauu  3240
uuuuuucuau  uucugcaaag  aauguuauug  guguuucau  agagauugca  uugaaucagu  3300
agauugcuuu  gggauuaag  gcguuuuaac  aauauugauu  cuccaauccc  augaauaugg  3360
aauaacuuuc  cauuuuuuug  agugccucu  ugaauuucuu  ucauggugu  uuuauaguuu  3420
ucauuguaga  aaucuuuuac  uucuuuuggu  aauuuaauuc  cuaggauuuu  aauuuuauuu  3480
guggcuauug  uaaauggau  uacuuuuuaa  auucuuuuu  cacauuguuc  auuauugaca  3540
uauagaaaug  cuacugauuu  uuguauguug  auuuuauauc  cugcaacuuu  auugaauuca  3600
uuuagcaguu  cuauaguuu  uuuggguggag  uccucagguu  uucccaaaua  ugugaucaua  3660
ucauuugcau  acaaggauaa  cuugacuucu  ugcuuucuag  uuuggaugac  cuuuauuucc  3720
uucucuuguc  uaauuguucu  ggcuaggacu  uccagugcac  uaggacuugc  cuagaaauug  3780
cagccuugu  ggccuagacu  gccccucaag  uuaaccuagg  gcccuagagc  acuccagccc  3840
augguggga  ggcuugcugg  aacucaagcu  ccaaccacug  ggaugagcga  ugccccucug  3900
gcuagggcca  guccaaaugc  ucccuccaug  ggcagacacc  agcugaguac  agccugguc  3960
ugcuuuccac  cgugacagug  caacacagag  uucaaugcaa  agccacagaa  ugacugcacu  4020
cuccucucc  caaacagag  auuccccaug  cugcacaguc  acugcuaggg  gaugugggag  4080
gaguggcauu  ggugcuucaa  gacuaucuuu  ccugcccucu  ucaaugcucuc  uuucagugau  4140
```

```
guaaagucaa aaccagguac ugugauugcu caccugauuu ucgguucucu ugauggugcu    4200
uuuugugugu aguuaguugu uaaaauuuag uguaccaaca ggaaagacaa augguguagg    4260
cuucuauuca gccaucuugc ucuccccucu cauauauuuu uucguuuuuc aauuuuucaa    4320
cuauaaucau cuggcuuggc uucagcugga uagaagucuc ucucugcagc ccccuccuuc    4380
cuggaacucu cccucauucc agacaaguug gccuugcaaa acucccauca guguugccac    4440
aagucuucaa aaucaucagg cucugcuugu auuccucucc cugcccuagu cuguaaacug    4500
ccucuaggca guaagcuggg gcaauuuuag guuucaccua auuguuuccu uucucuuaga    4560
gaucacaguc uugcuaugc ucuaaugucu gaaaacuguu auuuugcaua ucauguuuug     4620
uuuucuauua aggcaucuua uaugaaaaca gaaguucagu ccauuuuuau uaaaguaaau    4680
auaaacaaau uaccaaguua aagaaggcag agaaccauau aaagccuccu uuuuucuaau    4740
auaaacacaa uuauuacaau uauauauaua agugcaaaua acuuuauaga cugaucgaua    4800
ucuuguauaa ucucaggaau acuaaacauu uagcaauuua agaaaaaaau cauuaaagau    4860
auuuaaugcu uuguuuugcc aaugcuauua guggaaaaau ccuaaggccu uuauaguuug    4920
uuuguuuguu uguuuguuug uuugugacag agucucucuc uguuacccag gcuggagugc    4980
aguggugcaa ucucggcuca cugcaaccuc uaccucccag guucaaguga uucuugugcc    5040
ucagccuccu gaguagcugg gacuauagac acccgccacc augcccagcu aauuuuugug    5100
uuuuuaguag agacggggu ucaacauguu ggccaggcug aucucgaauu ccugaccuca    5160
ggugaucugc ccaccucggc cucccaaagu gcgggauua caggcaugag ccacugcacc    5220
cugccuauaa uucuauuug gaagcauuaa acaaaaguu uuauuaccu uucagaaaau     5280 gcuuaaguua cagauuaaug gccauauuuu aaaauucacc uauaaguaga auuuauauug    5340
uuuuuccaua auugaauaug auuuuuugu ccag                                5374

<210> SEQ ID NO 5
<211> LENGTH: 150
<212> TYPE: RNA
<213> ORGANISM: artificial
<220> FEATURE:
<223> OTHER INFORMATION: murine pre-mRNA exon 9 IL1RAcP

<400> SEQUENCE: 5
ucauaccacc aagguacaca guagaacucg ccgugguuu uggagccacg gucuuucugg      60
uagugguucu cauuguggu uaccauguuu acggcugga gaugguccuc uuuuaccgag      120
cucacuuugg aacagaugaa acaauucuug                                     150

<210> SEQ ID NO 6
<211> LENGTH: 150
<212> TYPE: RNA
<213> ORGANISM: artificial
<220> FEATURE:
<223> OTHER INFORMATION: human pre-mRNA exon 9 IL1RAcP

<400> SEQUENCE: 6
ucauaccacc aagguacaca guagaacucg ccgugguuu uggagccacg gucuuucugg      60
uagugguucu cauuguggu uaccauguuu acggcugga gaugguccuc uuuuaccgag      120
cucacuuugg aacagaugaa acaauucuug                                     150

<210> SEQ ID NO 7
<211> LENGTH: 5403
<212> TYPE: RNA
```

<213> ORGANISM: murine

<400> SEQUENCE: 7

| | | | | | | |
|---|---|---|---|---|---|---|
| gccgcuacca | gccauggguc | uuuggggaau | acuuugucuu | uuaauuuucc | uggacaaaac | 60 |
| uuggggacag | gaacaaaccu | acgucauuuc | agcacccaaa | auccuccggg | ucggcucguc | 120 |
| ugaaaaugug | guaauucaag | uccauggcua | cacugaagca | uuugaugcaa | cucuuucucu | 180 |
| aaaaagcuau | ccugacaaaa | aagucaccuu | ucuucaggc | uauguuaauu | ugucccgga | 240 |
| aaacaaauuc | caaaacgcgg | cacuguugac | acuacagccc | aaucaaguuc | cuagagaaga | 300 |
| aagcccaguc | ucucacgugu | aucuggaagu | ugugucaaaa | cacuuuucaa | aaucaaagaa | 360 |
| aauaccaauu | accuauaaca | auggaauucu | cuucauccau | acagacaaac | cuguuuacac | 420 |
| gccggaccag | ucaguaaaga | ucagagucua | uucucugggu | gacgacuuga | agccagccaa | 480 |
| acgggagacu | gucuuaacuu | ucauagaccc | cgaaggauca | gaaguugaca | uuguagaaga | 540 |
| aaaugauuac | accggaauua | ucucuuuucc | ugacuucaag | auuccaucua | aucccaagua | 600 |
| ugguguuugg | acaauuaaag | cuaacuauaa | gaaggauuuu | acaacaacug | gaacugcaua | 660 |
| cuuugaaauu | aaagaauaug | ucuugccacg | auucucuguu | ucaauagaac | uagaaagaac | 720 |
| cuucauuggc | uauaaaaacu | uuaagaacuu | ugaaaucacu | gugaaagcaa | gauauuuuua | 780 |
| uaauaaagug | guaccugaug | cugaagugua | ugccuuuuuu | ggauugagag | aggacauaaa | 840 |
| agaugaggag | aagcagauga | ugcacaaagc | cacacaagcc | gcaaaguugg | uugacggagu | 900 |
| ugcucagauc | ucuuuugauu | cugaaacagc | aguuaaagag | cuguccuaca | acagucuaga | 960 |
| agacuuaaac | aacaaguacc | uuuauauugc | aguaacaguc | acagaaucuu | caggugggauu | 1020 |
| uucagaagag | gcagaaaucc | cuggagucaa | auaugccuc | ucucccuaca | cacugaauuu | 1080 |
| ggucgcuacu | cccucuuuucg | ugaagcccgg | gauuccauuu | uccaucaagg | cacagguuaa | 1140 |
| agauucacuc | gagcaggcgg | uaggaggggu | cccaguaacu | cugauggcac | aaacagucga | 1200 |
| ugugaaucaa | gagacaucug | acuuggaaac | aaagaggagc | aucacucaug | acacugaugg | 1260 |
| aguagcugug | uuugugcuga | accucccauc | aaaugugacg | gugcuaaagu | ugagaucag | 1320 |
| aacugaugac | ccagaacuuc | ccgaagaaaa | ucaagccagc | aaagagaucg | aagcaguugc | 1380 |
| guacucgucu | cucagccaaa | guuacauuua | caucgcuugg | acugaaaacu | acaagcccau | 1440 |
| gcuugggga | gaauaccuga | auauuauggu | uaccccccaag | agcccauaua | ucgacaaaau | 1500 |
| aacucacuau | aauuacuuga | uuuuauccaa | aggcaaaauu | guacaguacg | gcacaagaga | 1560 |
| gaaacuuuuc | uccucaacuu | aucaaaauau | aaauauucca | gugacacaga | acaugguucc | 1620 |
| uucagcacga | cuccuggucu | auuacauagu | cacaggggag | caaacagcag | aauuagugc | 1680 |
| ugacgcaguc | uggauaaaua | uugaggagaa | guguggcaac | cagcuccagg | uccaucuguc | 1740 |
| uccagaugaa | uaugucuauu | cuccaggcca | aacugugucc | cuugacaugg | ugacugaagc | 1800 |
| agacucaugg | guagcacuau | cagcagugga | cagagcugug | uauaaaagucc | agggaaacgc | 1860 |
| caaaagggcc | augcaaagag | ucuuucaagc | uuuggaugaa | aagagugacc | ugggcugugg | 1920 |
| ggcagguggu | ggccaugaca | augcagaugu | auuccaucua | gcugggcuca | ccuuccucac | 1980 |
| caacgcaaac | gcagaugacu | cccauuaucg | ugaugacucu | uguaaagaaa | uucucagguc | 2040 |
| aaagagaaac | cugcaucucc | uaaggcagaa | aauagaagaa | caagcugcua | aguacaaaca | 2100 |
| uagugugcca | agaaaaugcu | gcaugacgg | agcccgagug | aacuucacg | aaaccuguga | 2160 |
| ggagcgagug | gccgggguua | ccauaggccc | ucucugcauc | agggccuuca | acgagugcug | 2220 |
| uacuauugcg | aacaagaucc | gaaaagaaag | cccccauaaa | ccuguccaac | ugggaaggau | 2280 |

```
ccacauuaag  acccuguuac  cagugaugaa  ggcagauauc  cgaagcuacu  uuccagagag    2340
cuggcuaugg  gaaauucauc  gcguucccaa  aagaaaacag  cugcagguca  cgcugccuga    2400
cucacuaacg  acuugggaaa  uucaaggcau  uggcauuuca  gacaauggua  uauguguugc    2460
ugauacacuc  aaggcaaagg  uguucaaaga  agucuuccug  gagaugaaca  uaccauauuc    2520
uguugugcga  ggagaacaga  uccaauugaa  aggaacuguu  uacaacuaua  ugaccucagg    2580
gacaaaguuc  uguguuaaaa  ugucugcugu  ggaggggauc  ugcacuucag  gaagcucagc    2640
ugcuagccuu  cacaccucca  ggccuccag   augugcguuc  cagaggauag  agggcucguc    2700
cagucacuug  gugaccuuca  cccugcuucc  ucggaaaauu  ggccuucacu  ccauaaacuu    2760
cucacuagag  accucauuug  gaaagacau   cuuaguaaag  acauuacggg  uagugccaga    2820
aggagucaag  agggaaagcu  augccggcgu  gauucuggac  ccuaagggaa  uucgugguau    2880
uguuaacaga  cgaaaggaau  ucccauacag  gauccccauua  gauuuggucc  caagaccaa    2940 aguugaaagg  auuuugagug  ucaaaggacu  gcuuguaggg  gaguucuugu  ccacgguucu    3000
gaguaaggaa  ggcaucaaca  uccuaaccca  ccuccccaag  ggcagugcag  aggcagagcu    3060
caugagcaua  gcccggugu   ucuauguuuu  ccacuaccug  gaagcaggaa  accauuggaa    3120
uauuuucuau  ccugauacac  ugaguaaaag  acagagccug  gagaaaaaaa  uaaaacaagg    3180 ggugugagc   ucaugaccuu  acagaaacgc  ugacauuccu  uacagcaugu  ggaaggggc    3240 gagcgcuagu  accggcuga   cagcuuuugc  ucugagagug  cuuggacagg  uggccaagua    3300
uguaaaacag  gaugaaaacu  caauuuguaa  cucuuugcua  uggcugguug  agaaguguca    3360
gcuggaaaac  ggcucuuuca  aggaaaauuc  ccaauaucua  ccaauaaaau  uacaggguac    3420
uuugccugcu  gaagcccaag  agaaaacuuu  guaucuuaca  gccuuuucug  ugauuggaau    3480
uagaaaggca  guugacauau  gccccaccau  gaaaauccac  acagcgcuag  auaaagccga    3540
cuccuuccug  cuugaaaaca  cccugccauc  aagagcacc   uucacacugg  ccauuguagc    3600
cuaugcucuu  ucccuaggag  acagaacccca  cccgagguuu  cgucaauug   ugucggcccu    3660 gaggaaggaa  gcuuuuguua  aaggugaucc  gcccauuuac  cguuacugga  gagauacccu    3720
caaacgucca  gacagcucug  ugcccagcag  cggcacagca  gguaugguug  aaaccacagc    3780
cuaugcuuug  cucgccagcc  ugaaacugaa  ggauaugaau  uacgccaacc  ccaucaucaa    3840
guggcuaucu  gaagagcaga  gguauggagg  cgguuuuuau  uccacccagg  auacgauuaa    3900
ugccaucgag  ggccugacag  aauauucacu  ccuguuaaaa  caaauucauu  ggauaugga    3960 caucaauguc  gccacaaaac  acgaaggaga  cuuccacaag  uauaaggu    cagagaagca    4020 uuuccugggg  aggccagugg  agguaucucu  caaugaugac  cuuguugca   gcacaggcua    4080 cagcagugcc  uuggccacag  uauauguaaa  aacuggguu   cacaaaauua  gugucucuga    4140
ggaauuuugc  agcuuuuacu  ugaaaauuga  ucccaagau   auugaagcau  ccagccacuu    4200
caggcucagu  gacucuggau  ucaagcgcau  aauuagcaugu  gccagcuaca  agcccagcaa    4260
ggaggaguca  acauccgggu  ccucccaugc  aguaauggau  auaucacugc  cgacuggaau    4320
cggagcaaac  gaggaagauu  uacgggcucu  ugugaagga   guggaucaac  uacuaacuga    4380
uuaccagauc  aaagauggcc  augucauucu  gcaacgaauu  cgaucccccu  ccagagauuu    4440 ccucugugc   cgguuccgga  uauuugaacu  uuccaaguu   ggguucuga   auccugcuac    4500 cuucacgguug  uacgaguauc  acagaccaga  uaagcagugc  accaugauuu  auagcauuuc    4560
ugacaccagg  cuucagaaag  ucugugaagg  agcagcuugc  acaugugugg  aagcugacug    4620
```

| | |
|---|---|
| ugcgcaacug caggcagaag uagaccuagc caucucugca gacuccagaa aagagaaagc | 4680 |
| cuguaaacca gagacugcau augcuuauaa agucaggauc acaucagcca cugaagaaaa | 4740 |
| uguuuuuguc aaguacacug cgacucuucu ggucacuuac aaaacagggg aagcugcuga | 4800 |
| ugagaauucg gaggucaccu ucauuaaaaa gaugagcugu accaaugcca accuggugaa | 4860 |
| agggaagcag uauuuaauca ugggcaaaga gguucugcag aucaaacaca auucaguuu | 4920 |
| caaguauaua uacccucuag auuccuccac cuggauugaa auuggccca cagacacaac | 4980 |
| guguccaucc ugucaagcau uuguagagaa uuugaauaac uuugcugaag accucuuuu | 5040 |
| aaacagcugu gaaugaaaag uucugcgcca cgaagauucc uccugcggcg ggggauugc | 5100 |
| uccuccucug gcuuggaaac cuagccuaga aucagauaca cuuucuuuag aguaaagcac | 5160 |
| aagcugauga guuacgacuu ugugaaaugg uagccuuga ggggaggcga aaacaggucc | 5220 |
| cccaaggcua ucagauguca gugccaauag acugaaacaa gucuguaaag uuagcaguca | 5280 |
| gggguguugg uuggggccgg aagaagagac ccacugaaac guagccccu uaucaaaaca | 5340 |
| uauccuugcu ugaaagaaaa auaccaagga cagaaaaugc cauaaaaucu ugacuuugca | 5400 |
| cuc | 5403 |

<210> SEQ ID NO 8
<211> LENGTH: 5031
<212> TYPE: RNA
<213> ORGANISM: homo sapiens

<400> SEQUENCE: 8

| | |
|---|---|
| augggccuuu ugggaauacu uuguuuuuua aucuuccugg ggaaaaccug gggacaggag | 60 |
| caaacauaug ucauuucagc accaaaaaua uuccguguug gagcaucuga aaauauugug | 120 |
| auucaaguuu auggauacac ugaagcauuu gaugcaacaa ucucuauuaa aaguuauccu | 180 |
| gauaaaaaau uuaguuacuc cucaggccau guucauuuau ccucagagaa uaaauuccaa | 240 |
| aacucugcaa ucuuaacaau acaaccaaaa caauugccug gaggacaaaa cccaguuucu | 300 |
| uauguguauu uggaaguugu aucaaagcau uuucaaaaau caaaagaau gccaauaacc | 360 |
| uaugacaaug dauuucucuu cauucauaca gacaaaccug uuuauacucc agaccaguca | 420 |
| guaaaaguua gaguuuauuc guugaaugac gacuugaagc cagccaaaag agaaacuguc | 480 |
| uuaacuuuca uagauccuga aggaucagaa guugacaugg uagaagaaau ugaucauauu | 540 |
| ggaauuaucu cuuuuccuga cuucaagauu ccgucuaauc cuagauaugg uauguggacg | 600 |
| aucaaggcua aauauaaaga ggacuuuuca acaacuggaa ccgcauauuu ugaaguuaaa | 660 |
| gaauaugucu ugccacauuu uucugcucuca aucgagccag aauauaauuu cauugguuac | 720 |
| aagaacuuua agaauuuuga auuacuaua aaagcaagau auuuuauaa uaaaguaguc | 780 |
| acugaggcug acguuuauau cacauuugga auaagagaag acuuaaaaga ugaucaaaaa | 840 |
| gaaaugaugc aaaacagcaau gcaaaacaca auguugauaa auggaauugc ucaagucaca | 900 |
| uuugauucug aaacagcagu caaagaacug ucauacuaca guuagaaga uuuaaacaac | 960 |
| aaguaccuuu auauugcugu aacagcauua gaucuacag uggauuuuc ugaagaggca | 1020 |
| gaaauaccug gcaucaaaua ugccucucu cccuacaaac ugaauuuggu ugcuacuccu | 1080 |
| cuuuuccuga agccugggau uccauauccc aucaaggugc agguuaaaga uucgcuugac | 1140 |
| caguggguag gaggaguccc aguaacacug aaugcacaaa caauugaugu aaaccaagag | 1200 |
| acaucugacu uggauccaag caaaagugua acacguguug augauggagu agcuuccuuu | 1260 |
| gugcuuaauc ucccaucugg agugacggug cuggaguuua augucaaaac ugaugcucca | 1320 |

```
gaucuuccag aagaaaauca ggccagggaa gguuaccgag caauagcaua cucaucucuc    1380
agccaaaguu accuuuauau ugauuggacu gauaaccaua aggcuuugcu aguggagaa    1440 caucugaaua uuauuguuac ccccaaaagc ccauauauug acaaaauaac ucacuauaau    1500
uacuugauuu uauccaaggg caaaauuauc cacuuuggca cgagggagaa auuuucagau    1560
gcaucuuauc aaaguauaaa cauuccagua acacagaaca ugguuccuuc aucccgacuu    1620
cuggucuauu acaucgucac aggagaacag acagcagaau uagugucuga uucagucugg    1680
uuaaauauug aagaaaaaug uggcaaccag cuccagguuc aucugcuccc ugaugcagau    1740
gcauauucuc caggccaaac ugugucucuu aauauggcaa cuggaaugga uuccggggug    1800
gcauuagcag caguggacag ugcuguguau ggagccaaa gaggagccaa aaagcccuug    1860
gaaagaguau uucaauucuu agagaagagu gaucugggcu gugggcagg ugguggccuc    1920 aacaaugcca auguguucca ccuagcugga cuuaccuucc ucacuaaugc aaaugcagau    1980
gacucccaag aaaaugauga accuuguaaa gaaauucuca ggccaagaag aacgcugcaa    2040
aagaagauag aagaaauagc ugcuaaauau aaacauucag uagugaagaa auguuguuac    2100
gauggagccu gcguuaauaa ugaugaaacc ugugagcagc gagcugcacg gauuaguuua    2160
gggccaagau gcaucaaagc uuucacugaa uguugugucg ucgcaagcca gcuccgugcu    2220
aauaucucuc auaaagacau gcaauuggga aggcuacaca ugaagacccu guuaccagua    2280
agcaagccag aaauucggag uuauuuucca gaaagcuggu uggggaagu ucaucuuguu    2340 cccagaagaa aacaguugca guuugcccua ccugauucuc uaaccaccug ggaaauucaa    2400
ggcguuggca uucaaacac ugguauaugu guucugauaa cugucaaggc aaagguguuc    2460
aaagaugucu uccuggaaau gaauauacca uauucuguug uacgaggaga acagauccaa    2520
uugaaaggaa cuguuacaa cuauaggacu ucugggaugc aguucugugu uaaaaugucu    2580
gcuguggagg gaaucugcac uucggaaagc ccaucauug ucaucaggg cacaaagucc    2640 uccaaaugug ugcgccagaa aguagagggc uccuccaguc acugguugac auucacugug    2700
cuucccucgg aaauuggccu ucacaacauc aauuuucac uggagacuug guuuggaaaa    2760
gaaaucuuag uaaaaacauu acgaguggug ccagaaggug ucaaaaggga aagcuauucu    2820 ggguuacuu uggauccuag ggguauuuau gguaccauua gcagacgaaa ggaguuccca    2880
uacaggauac ccuuagauuu ggucccaaa acagaaauca aaaggauuuu gaguguaaaa    2940
ggacugcuug uaggugagau cuugucugca guucuaaguc aggaaggcau caauauccua    3000
acccaccucc ccaaagggag ugcagaggcg gagcugauga gcguugccc aguauucuau    3060 guuuuucacu accuggaaac aggaaaucau uggaacauuu ucauucuga cccauuaauu    3120 gaaaagcaga aacugaagaa aaauuaaaa gaagggaugu ugagcauuau guccuacaga    3180
aaugcugacu acucuuacag ugugggaag gguggaagug cuagcacuug guuaacagcu    3240
uuugcuuuaa gaguacuugg acaaguaaau aaauacguag agcagaacca aaauucaauu    3300
uguaauucuu uauugugcgu aguugagaau uaucaauuag auaauggauc uucaaggaa    3360 aauucacagu ucaaccauu aaaauuacag gguaccuugc cuguugaagc ccgagagaac    3420
agcuuauauc uuacagccuu uacugugauu ggaauuagaa aggcuuucga uauaugcccc    3480
cuggugaaaa ucgacacagc ucuaauuaaa gcugacaaccu uucugcuuga aaauacacug    3540
ccagcccaga gcaccuuuac auuggccauu ucugcguaug cucuuucccu gggagauaaa    3600
acucacccac aguucguuc aauuguuuca gcuuugaaga gagaagcuuu gguuaaaggu    3660
```

| | | | | |
|---|---|---|---|---|
| aauccacccca | uuuaucguuu | uuggaaagac | aaucuucagc | auaaagacag cucuguaccu | 3720 |
| aacacuggua | cggcacguau | gguagaaaca | acugccuaug | cuuuacucac cagucugaac | 3780 |
| uugaaagaua | uaaauuaugu | uaacccaguc | aucaaauggc | uaucagaaga gcagagguau | 3840 |
| ggagguggcu | uuuauucaac | ccaggacaca | ucaaugcca | ugagggccu gacggaauau | 3900 |
| ucacuccugg | uuaaacaacu | ccgcuugagu | auggacaucg | auguucuua caagcauaaa | 3960 |
| ggugccuuac | auaauuauaa | aaugacagac | aagaauuucc | uggggaggcc aguagaggug | 4020 |
| cuucucaaug | augaccucau | ugucaguaca | ggauuuggca | guggcuuggc uacaguacau | 4080 |
| guaacaacug | uaguucacaa | aaccaguacc | ucugaggaag | uuugcagcuu uuauuugaaa | 4140 |
| aucgauacuc | aggauauuga | agcaucccac | uacagaggcu | acggaaacuc ugauuacaaa | 4200 |
| cgcauaguag | caugugccag | cuacaagccc | agcaggaag | aaucaucauc uggauccucu | 4260 |
| caugcgguga | uggacaucuc | cuugccuacu | ggaaucagug | caaaugaaga agacuuaaaa | 4320 |
| gcccuugugg | aaggggugga | ucaacuauuc | acugauuacc | aaaucaaaga uggacauguu | 4380 |
| auucugcaac | ugaauucgau | ucccuccagu | gauuuccuuu | guguacgauu ccggauauuu | 4440 |
| gaacucuuug | aaguugggu | ucucaguccu | gccacuuuca | caguguacga auaccacaga | 4500 |
| ccagauaaac | aguguaccau | guuuuauagc | acuuccaaua | ucaaaauuca gaaagucugu | 4560 |
| gaaggagccg | cgucaagug | uguagaagcu | gauugugggc | aaaugcagga agaauuggau | 4620 |
| cugacaaucu | cugcagagac | aagaaaacaa | acagcaugaa | aaccagagau ugcauaugcu | 4680 |
| uauaaaguua | gcaucacauc | caucacugua | gaaaauguuu | ugucaaguaa caaggcaacc | 4740 |
| cuucuggaua | ucuacaaaac | uggggaagcu | guugcugaga | aagacucuga gauuaccuuc | 4800 |
| auuaaaaagg | uaaccuguac | uaacgcugag | cugguaaaag | gaagacagua cuuaauuaug | 4860 |
| gguaaagaag | cccuccagau | aaaauacaau | uucaguuuca | ggacaucua cccuuuagau | 4920 |
| uccuugaccu | ggauugaaua | cuggccuaga | gacacaacau | guucaucgug ucaagcauuu | 4980 |
| uuagcuaauu | uagaugaauu | ugccgaagau | aucuuuuuaa | auggaugcua a | 5031 |

<210> SEQ ID NO 9
<211> LENGTH: 1713
<212> TYPE: RNA
<213> ORGANISM: murine

<400> SEQUENCE: 9

| | | | | |
|---|---|---|---|---|
| augggacuuc | uggguauuu | gaugagucug | uccuucuaug | ggauccugca gagucaugcu | 60 |
| ucggagcgcu | gugaugacug | gggacuagau | accaugcgac | aaauccaagu guuugaagau | 120 |
| gagccggcuc | gaaucaagug | ccccucuuu | gaacacuucc | ugaaguacaa cuacagcacu | 180 |
| gcccauuccu | cuggccuuac | ccugaucugg | uacuggacca | ggcaagaccg ggaccuggag | 240 |
| gagcccauua | acuuccgccu | cccagagaau | cgcaucagua | aggagaaaga ugugcucugg | 300 |
| uccggcccca | ccucccucaa | ugacacgggc | aauuacaccu | gcauguugag gaacacaacu | 360 |
| uacugcagca | aaguugcauu | uccccuggaa | guugucaga | aggacagcug uuucaauucu | 420 |
| gccaugagau | ucccagugca | aagaugauau | auugaacaug | gcauucauaa gaucacaugu | 480 |
| ccaaauguag | acggauacuu | uccuccagu | gucaaaccau | cggucacuug guauaagggu | 540 |
| uguacugaaa | uagggacuu | ucauaaugua | cuacccgagg | gcaugaacuu gagcuuuuc | 600 |
| aucccccuugg | uuucaaauaa | cggaaauuac | acaugugugg | uuacauaucc ugaaacggg | 660 |
| cgucucuuuc | accuaccag | gacugugacu | guaaaggugg | uggcucacc aaaggaugca | 720 |
| uugccacccc | agaucuauuc | uccaaaugac | cguguugcu | augagaaaga accaggagag | 780 |

```
gaacugguua uucccugcaa agucuauuuc aguuucauua uggacuccca caaugagguc    840
ugguggacca uugauggaaa gaagccugau gacgucacag ucgacaucac uauuaaugaa    900
aguguaaguu auucuucaac ggaagaugaa acaaggacuc agauuuugag caucaagaaa    960
gucaccccgg aggaucucag gcgcaacuau gucugcaug cucgaaauac caaggggaa    1020 gcugagcagg cugccaaggu gaaacagaaa gucauaccac caagguacac aguagaacuc   1080
gccugugguu uggagccac ggucuuucug guagugguuc ucauuggu uaccauguu    1140 uacuggcugg agauggulccu cuuuuaccga gcucacuuug gaacagauga aacaauucuu   1200
gauggaaagg aguaugauau uuauguuucc uaugcaagaa augilggaaga agaggaauuu   1260 gugcugcuga cgcugcgugg aguuuuggag aaugaguuug gauacaagcu gugcaucuuc   1320
gacagagaca gccugccugg gggaauugruc acagaugaga cccgagcuu cauucagaaa   1380 agcagacgac uccugguugu ccuaagcccc aacuacgugc uccagggaac acaagcccuc   1440
cuggagcuca aggcuggccu agaaaauaug gccucccggg gcaacaucaa cgucauuuua   1500
gugcaguaca aagcugugaa ggacaugaag gugaaagagc ugaagccggg uaagacgglug   1560 cucacggluca uuaaauggaa aggagagaaa uccaaguauc cucagggcag guucuggaag   1620
caguugcagg uggccaugcc agugaagaag agucccaggu ggucuagcaa ugacaagcag   1680
ggucucuccu acucaucccu gaaaaacgua uga                                1713

<210> SEQ ID NO 10
<211> LENGTH: 1714
<212> TYPE: RNA
<213> ORGANISM: homo sapiens

<400> SEQUENCE: 10
augacacuuc uguggugugu agugagcucu acuuuuaug gaauccugca aagugaugcc     60
ucagaacgcu gcgaugacug gggacuagac accaugaggc aaauccaagu guuugaagau   120
gagccagcuc gcaucaagug cccacucuuu gaacacuucu ugaaauucaa cuacagcaca   180
gcccauucag cuggccuuac ucugaucugg uauuggacua ggcaggaccg ggaccuugag   240
gagccaauua acuuccgccu ccccgagaac cgcauuagua aggagaaaga ugcugugg    300 ucccggccca cucuccucaa ugacacuggc aacuauaccu gcauguuaag gaacacuaca   360 uauuugcagca aaguugcauu ucccuuggaa guuglucaaa aagacagcug uuucaauucc   420
cccaugaaac ucccagugca uaaacugulau auagaauaug gcauucagag gaucacuuglu   480 ccaaauguag auggauauuu uccuuccagu gucaaaccga cuaucacuug guauauggg    540 uguuauaaaa uacagaauuu uaauaauguga auacccgaag guaugaacuul gaguuuccuc   600 auugccuuaa uuucaauaa uggaaauuac acaugguguu uuacauaucc agaaaugga    660 cguacguuuc aucucaccag gacucugacu guaaagguag ugcucucucc aaaaaauagca   720 gugcccccug ugauccauuc accuaagauu caugugglucu augagaaaga accaggagag   780
gagcuacuca uucccuguac ggucauuu aguuucuga uggauucucg caaugagguu    840
ugguggacca uugauggaaa aaaaccugau gacaucacua uugaugucac cauuaacgaa   900
aguauaaguc uaguagaac agaagaugaa acaagaacuc agauuuugag caucaagaaa   960
guuaccucug aggaucucaa gcgcagcuau gucugucaug cuagaaguga caaggcgaa  1020 guugccaaag cagccaaggu gaagcagaaa guglccagcuc caagauacac aguggaaculg  1080 gcuuguggguu uggagccac agccuigucua guggluugauuc ucauuguglu uaccauguu    1140
```

-continued

```
uacuggcuag agauggvccu auuuuaccgg gcucauuuug aacagauga aaccauuuua   1200 gauggaaaag aguaugauau uuauguaucc uaugcaagga augcggaaga agaagaauuu   1260
guauuacuga cccuccgugg aguuuuggag aaugaauuug gauacaagcu gugcaucuuu   1320
gaccgagaca gucugccugg gggaauuguc acagaugaga cuuugagcuu cauucagaaa   1380
agcagacgcc uccugguugu ucuaagcccc aacuacgugc uccagggaac ccaagcccuc   1440
cuggagcuca aggcuggccu agaaaauaug gccucucggg caacaucaa cgucauuuua   1500 guacaguaca aagcugugaa ggaaacgaag gugaaagagc ugaagagggc uaagacggug   1560
cucacgguca uuaaauggaa agggggaaaaa uccaaguauc cacagggcag guucuggaag   1620
cagcugcagg uggccaugcc agugaagaaa aguccaggc ggucuagcag ugaugagcag   1680
ggccucucgu auucaucuuu gaaaaaugua ugaa                               1714
```

```
<210> SEQ ID NO 11
<211> LENGTH: 24
<212> TYPE: RNA
<213> ORGANISM: artificial
<220> FEATURE:
<223> OTHER INFORMATION: murine C5 oligonucleotide

<400> SEQUENCE: 11
cagguuucgu agaaguucac ucgg                                          24

<210> SEQ ID NO 12
<211> LENGTH: 20
<212> TYPE: RNA
<213> ORGANISM: artificial
<220> FEATURE:
<223> OTHER INFORMATION: murine C5 oligonucleotide

<400> SEQUENCE: 12
acagcacucg uugaaggccc                                               20

<210> SEQ ID NO 13
<211> LENGTH: 21
<212> TYPE: RNA
<213> ORGANISM: artificial
<220> FEATURE:
<223> OTHER INFORMATION: murine C5 oligonucleotide

<400> SEQUENCE: 13
acuuacggau ccuucccagu u                                             21

<210> SEQ ID NO 14
<211> LENGTH: 20
<212> TYPE: RNA
<213> ORGANISM: artificial
<220> FEATURE:
<223> OTHER INFORMATION: murine C5 oligonucleotide

<400> SEQUENCE: 14
ggaaaacuca uacuuacgga                                               20

<210> SEQ ID NO 15
<211> LENGTH: 25
<212> TYPE: RNA
<213> ORGANISM: artificial
<220> FEATURE:
<223> OTHER INFORMATION: murine C5 oligonucleotide

<400> SEQUENCE: 15
guacuuagca gcugaaaugg uggca                                         25
```

<210> SEQ ID NO 16
<211> LENGTH: 25
<212> TYPE: RNA
<213> ORGANISM: artificial
<220> FEATURE:
<223> OTHER INFORMATION: murine C5 oligonucleotide

<400> SEQUENCE: 16
cucgggcucc gucauagcag cauuu                                             25

<210> SEQ ID NO 17
<211> LENGTH: 25
<212> TYPE: RNA
<213> ORGANISM: artificial
<220> FEATURE:
<223> OTHER INFORMATION: murine C5 oligonucleotide

<400> SEQUENCE: 17
cacagguuuc guagaaguuc acucg                                             25

<210> SEQ ID NO 18
<211> LENGTH: 25
<212> TYPE: RNA
<213> ORGANISM: artificial
<220> FEATURE:
<223> OTHER INFORMATION: murine C5 oligonucleotide

<400> SEQUENCE: 18
gguaacccgg gccacucgcu ccuca                                             25

<210> SEQ ID NO 19
<211> LENGTH: 25
<212> TYPE: RNA
<213> ORGANISM: artificial
<220> FEATURE:
<223> OTHER INFORMATION: murine C5 oligonucleotide

<400> SEQUENCE: 19
cucguugaag gcccugaugc agaga                                             25

<210> SEQ ID NO 20
<211> LENGTH: 25
<212> TYPE: RNA
<213> ORGANISM: artificial
<220> FEATURE:
<223> OTHER INFORMATION: oligonucleotide

<400> SEQUENCE: 20
ccuucccagu uggacagguu uaugg                                             25

<210> SEQ ID NO 21
<211> LENGTH: 25
<212> TYPE: RNA
<213> ORGANISM: artificial
<220> FEATURE:
<223> OTHER INFORMATION: murine C5 olignucleotide

<400> SEQUENCE: 21
aaacucauac uuacggaucc uuccc                                             25

<210> SEQ ID NO 22
<211> LENGTH: 21
<212> TYPE: RNA
<213> ORGANISM: artificial
<220> FEATURE:

<223> OTHER INFORMATION: human C5 oligonucleotide

<400> SEQUENCE: 22
gcucgcugcu cacagguuuc a    21

<210> SEQ ID NO 23
<211> LENGTH: 23
<212> TYPE: RNA
<213> ORGANISM: artificial
<220> FEATURE:
<223> OTHER INFORMATION: human C5 oligonucleotide

<400> SEQUENCE: 23
acacaacauu cagugaaagc uuu    23

<210> SEQ ID NO 24
<211> LENGTH: 21
<212> TYPE: RNA
<213> ORGANISM: artificial
<220> FEATURE:
<223> OTHER INFORMATION: human C5 oligonucleotide

<400> SEQUENCE: 24
caggcuccau cguaacaaca u    21

<210> SEQ ID NO 25
<211> LENGTH: 22
<212> TYPE: RNA
<213> ORGANISM: artificial
<220> FEATURE:
<223> OTHER INFORMATION: murine IL-1RAcP oligonucleotide

<400> SEQUENCE: 25
cuccagccag uaaacauggu aa    22

<210> SEQ ID NO 26
<211> LENGTH: 21
<212> TYPE: RNA
<213> ORGANISM: artificial
<220> FEATURE:
<223> OTHER INFORMATION: murine IL-1RAcP oligonucleotide

<400> SEQUENCE: 26
aaaaccacag gcgaguucua c    21

<210> SEQ ID NO 27
<211> LENGTH: 20
<212> TYPE: RNA
<213> ORGANISM: artificial
<220> FEATURE:
<223> OTHER INFORMATION: murine IL-1RAcP oligonucleotide

<400> SEQUENCE: 27
augacuacag caaaugacaa    20

<210> SEQ ID NO 28
<211> LENGTH: 21
<212> TYPE: RNA
<213> ORGANISM: artificial
<220> FEATURE:
<223> OTHER INFORMATION: murine IL-1RAcP oligonucleotide

<400> SEQUENCE: 28
ccaaagugag cucgguaaaa g    21

```
<210> SEQ ID NO 29
<211> LENGTH: 20
<212> TYPE: RNA
<213> ORGANISM: artificial
<220> FEATURE:
<223> OTHER INFORMATION: murine IL-1RAcP oligonucleotide

<400> SEQUENCE: 29
gcacacuucc aauacuuacc                                               20

<210> SEQ ID NO 30
<211> LENGTH: 17
<212> TYPE: RNA
<213> ORGANISM: artificial
<220> FEATURE:
<223> OTHER INFORMATION: murine IL-1RAcP oligonucleotide

<400> SEQUENCE: 30
uacuuaccaa gaauugu                                                  17

<210> SEQ ID NO 31
<211> LENGTH: 25
<212> TYPE: RNA
<213> ORGANISM: artificial
<220> FEATURE:
<223> OTHER INFORMATION: murine IL-1RAcP oligonucleotide

<400> SEQUENCE: 31
gguaugacua cagcaaauga caaaa                                         25

<210> SEQ ID NO 32
<211> LENGTH: 25
<212> TYPE: RNA
<213> ORGANISM: artificial
<220> FEATURE:
<223> OTHER INFORMATION: murine IL-1RAcP oligonucleotide

<400> SEQUENCE: 32
guaccuuggu gguaugacua cagca                                         25

<210> SEQ ID NO 33
<211> LENGTH: 25
<212> TYPE: RNA
<213> ORGANISM: artificial
<220> FEATURE:
<223> OTHER INFORMATION: murine IL-1RAcP oligonucleotide

<400> SEQUENCE: 33
aaaaccacag gcgaguucua cugug                                         25

<210> SEQ ID NO 34
<211> LENGTH: 25
<212> TYPE: RNA
<213> ORGANISM: artificial
<220> FEATURE:
<223> OTHER INFORMATION: murine IL-1RAcP oligonucleotide

<400> SEQUENCE: 34
caguaaacau gguaaaccac aauga                                         25

<210> SEQ ID NO 35
<211> LENGTH: 25
<212> TYPE: RNA
<213> ORGANISM: artificial
<220> FEATURE:
<223> OTHER INFORMATION: murine IL-1RAcP oligonucleotide
```

```
<400> SEQUENCE: 35
aagaggacca ucuccagcca guaaa                                       25

<210> SEQ ID NO 36
<211> LENGTH: 25
<212> TYPE: RNA
<213> ORGANISM: artificial
<220> FEATURE:
<223> OTHER INFORMATION: murine IL-1RAcP oligonucleotide

<400> SEQUENCE: 36
caaagugagc ucgguaaaag aggac                                       25

<210> SEQ ID NO 37
<211> LENGTH: 25
<212> TYPE: RNA
<213> ORGANISM: artificial
<220> FEATURE:
<223> OTHER INFORMATION: murine IL-1RAcP oligonucleotide

<400> SEQUENCE: 37
agcacacuuc caauacuuac caaga                                       25

<210> SEQ ID NO 38
<211> LENGTH: 23
<212> TYPE: RNA
<213> ORGANISM: artificial
<220> FEATURE:
<223> OTHER INFORMATION: human IL-1RAcP oligonucleotide

<400> SEQUENCE: 38
uguuacuuac cuaaaauggu uuc                                         23

<210> SEQ ID NO 39
<211> LENGTH: 21
<212> TYPE: RNA
<213> ORGANISM: artificial
<220> FEATURE:
<223> OTHER INFORMATION: human IL-1RAcP oligonucleotide

<400> SEQUENCE: 39
uuucaucugu uccaaaauga g                                           21

<210> SEQ ID NO 40
<211> LENGTH: 23
<212> TYPE: RNA
<213> ORGANISM: artificial
<220> FEATURE:
<223> OTHER INFORMATION: human IL-1RAcP oligonucleotide

<400> SEQUENCE: 40
uagccaguaa acaugguaaa caa                                         23

<210> SEQ ID NO 41
<211> LENGTH: 23
<212> TYPE: RNA
<213> ORGANISM: artificial
<220> FEATURE:
<223> OTHER INFORMATION: human IL-1RAcP oligonucleotide

<400> SEQUENCE: 41
agaaucacca cuagcaggac ugu                                         23

<210> SEQ ID NO 42
<211> LENGTH: 21
```

```
<212> TYPE: RNA
<213> ORGANISM: artificial
<220> FEATURE:
<223> OTHER INFORMATION: human IL-1RAcP oligonucleotide

<400> SEQUENCE: 42
ucuuggagcu ggcacuggaa u                                              21

<210> SEQ ID NO 43
<211> LENGTH: 20
<212> TYPE: DNA
<213> ORGANISM: artificial
<220> FEATURE:
<223> OTHER INFORMATION: primer

<400> SEQUENCE: 43
aaacgcagat gactcccatt                                                20

<210> SEQ ID NO 44
<211> LENGTH: 20
<212> TYPE: DNA
<213> ORGANISM: artificial
<220> FEATURE:
<223> OTHER INFORMATION: primer

<400> SEQUENCE: 44
acgcgatgaa tttcccatag                                                20

<210> SEQ ID NO 45
<211> LENGTH: 20
<212> TYPE: DNA
<213> ORGANISM: artificial
<220> FEATURE:
<223> OTHER INFORMATION: primer

<400> SEQUENCE: 45
gaggatctca ggcgcaacta                                                20

<210> SEQ ID NO 46
<211> LENGTH: 21
<212> TYPE: DNA
<213> ORGANISM: artificial
<220> FEATURE:
<223> OTHER INFORMATION: primer

<400> SEQUENCE: 46
tcagcagcac aaattcctct t                                              21

<210> SEQ ID NO 47
<211> LENGTH: 20
<212> TYPE: DNA
<213> ORGANISM: artificial
<220> FEATURE:
<223> OTHER INFORMATION: primer

<400> SEQUENCE: 47
ttctcaggcc aagaagaacg                                                20

<210> SEQ ID NO 48
<211> LENGTH: 20
<212> TYPE: DNA
<213> ORGANISM: artificial
<220> FEATURE:
<223> OTHER INFORMATION: primer

<400> SEQUENCE: 48
```
gggcaaactg caactgtttt                                                          20

<210> SEQ ID NO 49
<211> LENGTH: 20
<212> TYPE: DNA
<213> ORGANISM: artificial
<220> FEATURE:
<223> OTHER INFORMATION: primer

<400> SEQUENCE: 49
caagcgcagc tatgtctgtc                                                          20

<210> SEQ ID NO 50
<211> LENGTH: 20
<212> TYPE: DNA
<213> ORGANISM: artificial
<220> FEATURE:
<223> OTHER INFORMATION: primer

<400> SEQUENCE: 50
tctcggtcaa agatgcacag                                                          20

<210> SEQ ID NO 51
<211> LENGTH: 20
<212> TYPE: DNA
<213> ORGANISM: artificial
<220> FEATURE:
<223> OTHER INFORMATION: primer

<400> SEQUENCE: 51
actgctctgg ctcctagcac                                                          20

<210> SEQ ID NO 52
<211> LENGTH: 20
<212> TYPE: DNA
<213> ORGANISM: artificial
<220> FEATURE:
<223> OTHER INFORMATION: primer

<400> SEQUENCE: 52
ccaccgatcc acacagagta                                                          20

<210> SEQ ID NO 53
<211> LENGTH: 22
<212> TYPE: DNA
<213> ORGANISM: artificial
<220> FEATURE:
<223> OTHER INFORMATION: primer

<400> SEQUENCE: 53
tggtagtggt tctcattgtg gt                                                       22

<210> SEQ ID NO 54
<211> LENGTH: 21
<212> TYPE: DNA
<213> ORGANISM: artificial
<220> FEATURE:
<223> OTHER INFORMATION: primer

<400> SEQUENCE: 54
tccaaagtga gctcggtaaa a                                                        21

<210> SEQ ID NO 55
<211> LENGTH: 20
<212> TYPE: DNA
<213> ORGANISM: artificial

-continued

<220> FEATURE:
<223> OTHER INFORMATION: primer

<400> SEQUENCE: 55
aaagccccca taaacctgtc                                          20

<210> SEQ ID NO 56
<211> LENGTH: 20
<212> TYPE: DNA
<213> ORGANISM: artificial
<220> FEATURE:
<223> OTHER INFORMATION: primer

<400> SEQUENCE: 56
tcggatatct gccttcatca                                          20

<210> SEQ ID NO 57
<211> LENGTH: 20
<212> TYPE: DNA
<213> ORGANISM: artificial
<220> FEATURE:
<223> OTHER INFORMATION: primer

<400> SEQUENCE: 57
actgctctgg ctcctagcac                                          20

<210> SEQ ID NO 58
<211> LENGTH: 20
<212> TYPE: DNA
<213> ORGANISM: artificial
<220> FEATURE:
<223> OTHER INFORMATION: primer

<400> SEQUENCE: 58
ccaccgatcc acacagagta                                          20

<210> SEQ ID NO 59
<211> LENGTH: 20
<212> TYPE: DNA
<213> ORGANISM: artificial
<220> FEATURE:
<223> OTHER INFORMATION: primer

<400> SEQUENCE: 59
tgctacacgg aggaagaagc                                          20

<210> SEQ ID NO 60
<211> LENGTH: 20
<212> TYPE: DNA
<213> ORGANISM: artificial
<220> FEATURE:
<223> OTHER INFORMATION: primer

<400> SEQUENCE: 60
catcatcatt agggccatcc                                          20

<210> SEQ ID NO 61
<211> LENGTH: 20
<212> TYPE: DNA
<213> ORGANISM: artificial
<220> FEATURE:
<223> OTHER INFORMATION: primer

<400> SEQUENCE: 61
aaacgcagat gactcccatt                                          20

-continued

<210> SEQ ID NO 62
<211> LENGTH: 14749
<212> TYPE: RNA
<213> ORGANISM: artificial
<220> FEATURE:
<223> OTHER INFORMATION: human intron 8 pre-mRNA IL-1RAcP

<400> SEQUENCE: 62

| | | | | | |
|---|---|---|---|---|---|
| guaauagaug | cggucaguga | ugaaucucuc | agcuccaaau | uaacauugug | gugaauaagg | 60 |
| acaaaaggag | agauugagaa | caagagagcu | ccagcaccua | gcccgacggc | aucuacccca | 120 |
| uaguaaugaa | ucaaacuuaa | augaaaaaua | ugaaaguuuu | caucuaugua | agauacucaa | 180 |
| aauauuguuu | cugauauugu | uaguaccgua | augcccaaau | guagcuaaaa | aaaucgacgu | 240 |
| gaguacagug | agacacaauu | uugugucugu | acauuauga | aaaauuaaaa | acaaagaaaa | 300 |
| uauucaaagc | uaccaaagau | agaaaaaacu | gguagagcca | cauauuguug | ugaauuauu | 360 |
| aagacccuuu | uaaaaaucau | ucaugguaga | cuucaagagu | cauaaaaaag | auugcaucau | 420 |
| cugaccuaag | acuuucggaa | uuuuuccuga | acaauaaca | gaaagggaau | uauauaccuu | 480 |
| uuaauauuau | uagaagcauu | aucuguaguu | guaaaacauu | auuaauagca | gccauccaau | 540 |
| uguaugcaac | uaauuaaggu | auugaauguu | uauuuuccaa | aaaugcauaa | uuauaauauu | 600 |
| auuuuaaaca | cuauguauca | auauuuaagc | agguuuauaa | uauaccagca | gccacaauug | 660 |
| cuaaaaugaa | aaucauuuaa | auuaugauuu | uaaaugguau | aaacaugauu | ucuauguuga | 720 |
| uaguacuaua | uuauucuaca | auaaauggaa | auuauaaagc | cuucuugucg | aagugcugc | 780 |
| uccuaaauca | gacugugucu | aaaacuuucu | ugugucucu | caccuaacac | agaaucccag | 840 |
| aaaaucccuu | caaggauguu | uucaaggguc | uugagaaaag | uaaugaugag | uuaucacaca | 900 |
| ugaaaucaug | aaaucaagguc | auucagaauc | cuccuggcuc | cuagucuaua | gagguguaa | 960 |
| uauuucuuca | aagugaaua | acauagcaca | uaauuguuac | auuuuacaga | gacuuaaugc | 1020 |
| uuuuuuaaag | cugaugaaaa | acaggauuca | ccucaaacuu | ucauuacaac | uuuaaaacua | 1080 |
| aauagcaaag | gccugaaaug | uauaugcugc | guaugaagua | cuagugaauc | aguucagggu | 1140 |
| aauucauugc | uucugcuccu | cagaagccag | ugugaaaagg | aaagacugaa | guacaugaug | 1200 |
| uaaggcaguu | ucccaaauug | aguucucggg | aacacuacua | agaaucagua | uuguccugca | 1260 |
| augcauuauu | guacucuaga | aucagagcac | cuguguugaa | auucggguuu | cugcacaucc | 1320 |
| uaacucugug | aaaaguaaau | cucucugagc | cuuaauuucc | uuauauuuaa | aguagacaca | 1380 |
| auaauaccac | uaccuuauaa | gguuguuuua | aagugcucag | cacaguuauu | ggcauauaua | 1440 |
| ccuauauaug | aaaugcucaa | uaauaugaa | cucauuauuu | ccuuaagauu | uucauaggug | 1500 |
| uuauuugaca | aaggcuuuua | ucaucaaaua | aguaucauuu | augucuggau | uuuaaaaaau | 1560 |
| caaucaaguu | acuuuaguua | ggacccauuc | aaguauuuaa | uaugugaaca | uugauggga | 1620 |
| auaucugcgg | gaaguuggau | uauaguggca | ggauguuuuc | auauguauuu | gacuccagau | 1680 |
| uucuuaagua | uggagcuuuu | uggggggauc | ucuucugag | ggauguaucc | uggggaauaa | 1740 |
| uuauggaagg | ugacauaaau | uaauaacuua | uugucaaaug | aauaggauca | gaacaaucaa | 1800 |
| agcaaggugu | aauguaggag | ugaagcacaa | guuugccucc | cagagcgacc | agauagcuc | 1860 |
| cccuuuuaca | gaagcccug | cucuaaaugg | uguaauaagg | acagugucag | gaaugugaag | 1920 |
| ugacagugg | auccucuaga | cuagaugauc | ugucugaaa | gcugauauaa | aaucacuguu | 1980 |
| uggcacacc | uguguauuuc | cgguugguacc | agaggaguug | uggguuucuu | cacuggcuu | 2040 |
| cuauucuggg | ccagcuaaug | cugaaauuca | gagguuauau | cugaguucac | auucauacau | 2100 |

```
uacauguaug ggacuacucu aaauuuauua gcaaagcauu auaugaacuu ccucaaaagg    2160
acaucaagaa aagacuaagg ccuggaauga gagaaagaca cugguguagg ucuuauugac    2220
agcaaaauuu cauuauaguc aguuaaagcu aaguauuaaa gaggaggcag uuguuuuauu    2280
uauauuuuau guauuuauuu uauuuauuu uuuauuuuug agacacaguu uuacucuugu     2340
caccuaggcu gaagugcagu ggcaugaucu cggcucacug caaccacugc cuccggguu    2400 caagugauuc uccugccuca gccucccaag uagcugggac uacacaggca ugugccacca    2460
cgccuggcua auuuuuguau uuuugcuaga gacaggauuu caccauguug gccaggcugg    2520
ucucaaacuc cugaccucag ugauccucc ugccucagcc ucccaaagug cugggauuac     2580
aggugugagc caccacgccc agcucauugu uuauaauaa cagcaugaaa aggacuaagg    2640
caagguaucu guuuaacuuu gugagaaacu gccaaaccug uuccaaaga gauuguacca    2700 uuuuaccugu ccucuagcaa uguucacaaa uccaggcgc ucuauuccu caccaauuuu     2760 uggagcuguc aaacuuucaa auuuuagcca uacugaugga ugcauaguuu auuacauug    2820 ugcuuuaaau uugcauuuau uggauacuaa ugauguugga caauuuuca uagccuuauu    2880 ugucauuagc uaauauaucu uuuugugaag uaucuguuaa aauguuuagc ucauuuugu    2940 uacggucau uuguuuuaa auuuaauguc uguuaggaua uagacacaga cgcauauaua     3000
ucucaaauaa aaguccugug ucagauauau gaauuguuaa uauuaucacc caguuuguga    3060
auucauuuuc uuuuaaacag aaucuuuaaa acuugaugg cauuuauugu aucaauuuau    3120
ucuaugcuua gugguuucua aauucaguau uagcaaucuu ugccaaagu uagaaaggua    3180 uucagguuag aaagguaucc uucuguguuu cuucuggaa gacugguaga uuuucuuuu     3240 agaguuaggc cuaugaucca uuuuuuuaau acucugaggu acugguuaa uguuuaguagu   3300 uuuguuuuuc cacauagaua accaguuguu cucauaucau auugaaaaau cuuuccuuug    3360
uuuguugaau uguucagaaa agagcccaaa aaauuaauuc uaugaauaua gaucuauuuc    3420 ugcauuccu gcucuguuca ucuguuuauc uaucuuuagu ccaaugccac uuuauccugg    3480
uuaacauagu uuuaaaauuu aaaguaagc augaaaucac auacauaug cuucccccu      3540 uuuuucuuuu ugaagauuga uucaacuauu uuaggaacca uauauuuuu uucguauaga    3600 ucauaguauc aguuugucca uuucuacaua aaggccugau gauauuuuga uuguauuuaa    3660
uuuauaaauc agcucggaga aaauugaauu cuuaacaaua cuguauuuc cagucauugg    3720 auauaauaua ucucuccauu uauuuagauc uuaacuuuuu ucagcauuuu uucuuuaga    3780 uuugagugua caggccuugc auauauauug uuaaauguau gccuaaauau uuuguuuug    3840 augcuauugu aauaguacuu uauuuaaau uauuuuuga gacagagucu cacugucacu    3900
uaggcugcag ugcaguggcg ugaucucggc ucacugcaau cuccaccucc ugaguucaag    3960
caauucuccu gccucagccu ccagaguagc ugcgauuaca gguccccacu accauacccg    4020
gcuaauuuuu auaguuuuag uagagacggg guuucuccau guuggccagg cuugcucaa    4080 acuccugacc ucagaugauc cacccuccuc agccucccuc ccaaagugcu gggauuauag    4140
ucgugagcca ccaugcccgg ccuguaauag uacuuuuuaa auuucauuu ccaguuguu    4200 cauugaaaau gcauuaauu gauuguaua uauugaucuu gaccuuuuga acuuagggu    4260 ggguuuguu uguuuaguuu guuaggauuu ccauaugcu ugauugugug acccaucauc    4320
aaacagauuu uuacuucuuc cuuucuaaau uucauaacuu uaauaacuuu uuacugccg    4380 uuucacucuu uuggaccucc aguacaaugu ucuguagaag uuuugagagc agccaucuuu    4440
```

-continued

| | |
|---|---|
| gcauuguuuc caaauuuaga gggcaagccu ucagguuuuu auauacagga uuuuuugua | 4500 |
| gaugaccuuu auuuucauga gcaauuuuuu cauuuucagu uugccgagaa uuuuuugug | 4560 |
| ugaguauguu gaguuugguu gaauacuuaa cuggaucuau ugagagaauu auauguuuuu | 4620 |
| auuuuuaauc ugucagugug augauuuaua cuuacugauu uugaaaugu cauccaauuu | 4680 |
| ugcaugucca gaauaaaccc ucauauuguc augauuuauu guccuuuuua uauauuacug | 4740 |
| gauuugauu acuaauauuu ugucacagau uuuuguucau guuaagaauu uuuuuuuuu | 4800 |
| uuuuuugag acagaguuuc ccucuuguug cccaggcugg aguacagugg cgcgaucucg | 4860 |
| gcucagugca accuccaccu ccuggguuca augauucuc cugccucagc uccugagua | 4920 |
| gcugggauua gaggcacccg ccaccauacc agcgaauuuu uuuuuucuuu ucaguagaga | 4980 |
| uugggucuuuca ccaaauuuug uucauaucuu guucaugaa ggauauuggu uuguuugguu | 5040 |
| uguaguauuc uuucuugua augcugugac uaaugugagg guuaugcugg ucucauuaca | 5100 |
| ugagcugggu aauguccccu cuuugugau uaugugaaag ccauagggua aaacugguau | 5160 |
| uauuucuugc ucaaaagaau uacucauaua acuaucuggg ccuguugugu uuuuuuuuu | 5220 |
| guuguuguuu uuuugagaa ggagucucgc ucuuucgccc aggcuggagu gcaguggcgc | 5280 |
| gaucucggcu cacugcaagc ucggccuccc ggguucacgc cauucuccug ccucagccuc | 5340 |
| ccgaguagcu gggacuacag gcguccgccu ccacggccgg cuaauuuuuu guauuuucag | 5400 |
| uagagacggg guuucacugu guuaaccagg auggucucga ucuccugacc uugugauccg | 5460 |
| cccgccuagg ccucccaaag ugcugggauu acaggcguga gccaccgugc ccggccguug | 5520 |
| uuuucuuuuu gggaaagcuu uuaauuauga auucagnguc cuuuuaguu auugagauuu | 5580 |
| ucuguuucuu cuuguggcag uuuuggcuuu caaggcauuu uuuuccauuu caucuaaguu | 5640 |
| gucacauuau uggcauacuu uucuuuagau uauuuccuau uaccuuuua augucugcag | 5700 |
| gauuuuuagu gauguccac ugcacucccu gauauuagua auuggguuuu ugccuuuuuu | 5760 |
| uguccuucau cagucaagau aagguuucu caauuuugcu aauuuuuca augaacauau | 5820 |
| uuuuauugau uuucucugu uguuauaua uuauuacu uauucauau acuuauuuuc | 5880 |
| cucuuuuugc auacuuugca cuucauuuuc uuuuugucag ucauccuaaa auguaagcug | 5940 |
| uaucacugau uuuuaaguaa uucuucuuuu ccaauauaag uauucugagc uauguguuuu | 6000 |
| ccucauagga uuaguuuaac uaaauccaac aaauguugaa augucgaguu uuuguuauua | 6060 |
| uuaaguucaa aauacuuucu aauuucuguu uucauucuu uuugaccuaa ggguuauuuc | 6120 |
| agugugugu uuuuaauuua aacaugcuug gaauuuucca gaucguuuua cuacauuaua | 6180 |
| uaugaaaauu cauuugaauu uuagaguugg cuuauguuc acucuugaua guuauuugua | 6240 |
| acauuucaua uugucauuua aguuuagcua auguaaaaaa uuagaaaaaa agucugggag | 6300 |
| cagguaucuc caacuuagaa cuaccugaga gaacuacauu acggagugga gaaacauagg | 6360 |
| uuuuuguucu agauagaccu ggguucaagu uccggacuca gugcuggcug uguauaugaa | 6420 |
| cuaguacaag ccuuccuuuu cuauccuuc agguucaauu uccaggguau cugugaaaac | 6480 |
| cgagggaaug gggaaugaga gcuuugccac agcugcugcac acuugauucu aauuucuaau | 6540 |
| cuuuuauuua auucugaugu guccaaagaa cauacuuugc augauuuuau ucuuuuuaag | 6600 |
| cuuauuggua cuuaaaaaaa aaguauuugc agacugccua ucugguaaa uguuugauau | 6660 |
| gcauuugaaa aagacauaua uuuguaguu ucgaguggug uccaguaaau gucaacuaag | 6720 |
| aaaauugggug ucaguuugu ucaugucuuc aauccuuc ugauuuuucc aauauacuuu | 6780 |
| guuauucagu uauuaaaaga gagaauggug uugaaaucuu uacauauaau auggauuuuu | 6840 |

```
ccaauucucu cuucaguucu gccaguauuu gucucaugua uuuuggaacu gugauauuua    6900
auacaugcuu auuuaggauu gacaagucuu uuucaugaau ugacucuuaa auugugaaau    6960
guccguuuuu ucucuguuaa uacucugugu cuaauaugaa uguagccauu ccagcuuucu    7020
uuuuuuuuac uuuuuuaauu aauuaauuuu uuuugguag  agggacggag ucuugcucug    7080
ucgcccaggc uggagugcag uggugcgauc ucagcucacu gccagcuuuc uuauaauuag    7140
uauaugcuuu uuccauuauu uuauuuuacc uaucagcauc uuuaugcuuu uauacuuaua    7200
cuuuauacuu aauguaugua ucuuauuuac agcauauuau ugggauuugg auccaaucug    7260 aucauucug  gcuuuuaacu ugaauguuua auccauuuuu cuuuaauuau uaauaugacu    7320
gccuuuaagu uuaccaucuu gcuauuuguu guccaccugu cuuuauuuuu aucuccucua    7380
gacuaauugg uauuuucauu guauuuuauu uuaucacuuu uuugagcuuu ggcucuucc     7440 uuuuuguuug gggcuuguuu uguuuuguuu ccucuagagu uuauaauauu uuuccuaaac    7500
uuaucaguug aucugaauu  aaucacuuua cauauuuuau gagaaacuua cuauggcgua    7560
uuccauuuuc uucccuccca uccuuugugu ugugcuauaa uacauuuugg uuuugcauga    7620
auuacagugu accaacaugu auugugaaag uuuggcuuua aauaacuguc uucuauuaag    7680
uuaagaacug aucuuuuuuu aaauuuauuu gcuuauuuuu uauuucugac acuauccauu    7740
cuugguaaca uuuuaaucug aagaacuauu uaauguuucu gguacaucug cuggugacaa    7800
auucucucag cuuuguuuua aucugaaaau guccuauuuc auuuuaauuu uuauauuuca    7860
aaacuuuacu aagaaaguuu ucaaauauau ggaagauuuu aaggaauuac acagugagca    7920
guaauacagc cuaccuagau ccuaccauua acauugguua ucuuugcuuu aucacaugc    7980 uauucauucu ucugccagua uaucaaucca ucuauuuuc  ugauacauuu caaaguagau    8040
gcagacauca guaaacauuu aagcuccuua ucauuaucag uguuuaaua  uuuauuugua    8100 gguuucuuu  cuagguaaaa uuugcauaaa guaacaaauu gcauaauuca agugguaccau   8160 uugauaauuu uugagaaaug cauauauaua ugcauuaccu aauauccuau uaagauauag    8220
aauauuacca ucaccagaaa guaacauucu uccccuuauc agucaauccu uucuaccccc    8280
accuucccca ccuccccaaa caauacaacu guuuuauuu  ccuuuuuag  aauaguuuu     8340 uuuuauaua uucuagaacu cuguguaugu ggaccauac  agaaugcgcu acuguauaac     8400
uguaccuuca cucagcaaau guucuugaua uucaccaug  cuguugugug uaucaggcau    8460
uuucuccuuu uguuugccau ggaguggu   uguuuuguu  uguuuuguu  uaagaaugca    8520 gaaugauuug uuuauucauu cucggggugg ugaacauuug gguuguauc  aguuuggggg    8580 ucuuuugaau aaagcuucug ugaacuuucu uauccaaguu ucuuaaugga cuaccgcuuu    8640
uacuucucug agaugaauac cuaugagugg aauuacugac uuaguuuuau cagaaacugu    8700
uagaccuuuu uuuuucccca aguggcugua ucauccauca uccaccauc  aacauauuua    8760 caucuuaagg auuuggugu  ucagccuuc  uuuguuuag  caauuauagg ugaguguaug    8820
gugguaucuu acuguaguuu aauucuucau uucccugaug ucucaaaaua cugagcacuu    8880
acaccucaug ugcuuauugg ccaucuguau guauuuuug  augugacugu caaacauuu     8940 uguucauuuu auaaauaguu uguauuuuau auugaaucu  uagcguucu  ucaucugucc    9000 uggauaccag uccuuuguca gacacauguu uugcaaauac uuucccag   ucuguugcau    9060 gacaauuugu uuuucguga  aguguuuaaa ugagcagagg uucucauuuu uuaugagaug    9120
uaauuuauua acuucuucuu uaaugauuau uaauuucugu guucuaagaa agcuuugcuu    9180
```

```
acccauaguc aggaagguuc accuuuguuu aggccuauag uccaucucuu uucuuuuuuu    9240
ucaugaaugg uguguaguag aaauugaagu ucaguuuucc uuucauaccg auauccaguu    9300
guuccagcac aauuaauugg aaagauuuuu acuuucucau uauguuucuc uggugccuuu    9360
gucaauauuu ucacaggaua uguugaaagu guaucuauuu cuuucuuuc agcccuuuaa    9420
gguauuccau ugucuccugg cuaauauuau uuaaaaugca aacggggcag uuuuuguugc    9480
ugcuguuguu cuuguuuauu uuugugcccu uauguauuu guuaguuuu ucuuggcag      9540
auuuuaagau caccuuuucu uuauugauuu ugaaaaucaa auuaugaugg ccuguggugu    9600
ccuuugugug ugugguuuc uuacuuagag uuuauuaaac uucucaguuc uauguguuua    9660
uauuuuccu uuacugugaa caauuuucag ccauuucuu uucaaauaug ucagcuuuc      9720
ccccucacuc uuucucuucu uuuaguacuc cagcugaaau uaggauagac cacugcuauc    9780
caauuaguag ugcccacag aucacugauc ucguuauuu uauucuucc uuuucaucc       9840
uuucccugc ucuguuuug uguaguuucc aauguaugcu ggccauuuuc uuugugaugu     9900
cuaaucgaua gcauuuucuu uauuucagaa uguaucuuu uagcuuuga auuccauau      9960
cuucauugaa aggucccuau ugauauuuuc uauuugcugu ucacaauguu caugguuuua   10020
aaaaaauuga acaaauacac auagaauacu cauuuuuagg guuuaucug auaauuccac    10080
cacuuuuguc aauuuuuguu cuguuuugau uagcuaucuu uuuauuagcu aauauagacu   10140
uuuuugcuuu uuuauauagc uuuuuaaaaa uuauaugcug gauauuaugg auguuacaau   10200
uuugaguucu gaauuucgua agacagugu aaauuuuguu cuagaggua auuaaauuac     10260
uugcauaacu gcuugcuuuu aaaaaagcau cuuaucuuu uuaaagcagg ucuaaaauag    10320
ccuuuucugu aagguuagau uggaccuacu ucuaaagcau gucauaccug aagucucuaa   10380
uuaauacugg ggagcuaaac acagucucuu cacucugagu ggccuguacc caacugucuc   10440
acagcccuuc augugcuccu agaguugauc uguuccagc uauucuuugc cuaaccuuuu    10500
aaaguauucc cccaaauaug uguagcuuug uauuuggccg aagacucgag auaaccugu    10560
gcagauuucu agaguuccau cucuaaauag uucucuucuc uauaaaugca aucugacuca   10620
acagcagccu ugaacucuca uuucuaucuc uuuagcucag ugugaccacu uucuucauuuu  10680
ggcuuucccu ucucuguugcc acaguuuaaa aggugccuuu aaucgaaaag ccagagugau  10740
cguagcauuu acccuuuuuu ugucuuuucu cucacagauc acauuccugu guuaccaguu   10800
guccaacuuu uuacaaacug uauuuuagau auggaaggaa ggcuagucca ggacuaguua   10860
cuccuuuaag aacagaagcu gaaguccaaa gugcacaugu uuaaacacac uauaauagcc   10920
aaaucaguaa caucugcgag uuaauuuagu cauaggucuc ugauuuauca uaauuuuaau   10980
aaagcauucc cuuuguuuac aaccucaggag aauggcauu accacaguuc caaaaauuau   11040
ccaucagucc caauaauuua gaacggagua gccaugggu cuguggcagg gaacacuugg    11100
aggugcaagc agcuggcauu uaguggggac augcagugga uggcaaggcu ccaacugcaa   11160
uaauaaagau gacggaaauc acucagauuu ccuagagaaa cgugauugua gagcaagaac   11220
ucaaaacagg gaaaaugcca agagcuaacc aaggugguua ccuggaaauu ugggcuuuga   11280
agccaguuau uuacauugaa cuacaaaagg gauggaaaaa auacugauuu aaggacuaac   11340
aaccaucaag gagcuaaauc uggcuacauc cugaaucaga auauuaguaa aaucaaugag   11400
agaaguuuag gaguccaguu uggcguacu acaucaugue uuucugauag gaaauucuuu    11460
uuuuauuuuu auuuuuauuu uuugagaca gaguuugcu cuuguugcca aggcuggagu    11520
gcaauggugc aaucuuggcu cacugcaacc uccgccuccc agguucaagc gauucuccug   11580
```

```
ccucagccuc ccgaguagcu gggauuacag gcaugcgcca ccacacccgg cuaauuuugu   11640
auuuuuaguu gagacagggu uucuccaugu uggucaggcu ggucucaaac ucccgaccuc   11700
aggugaucca ccggucuugg ccucccaaag uguuggggu acaggcguga gccacugcgc    11760
ccggccucug auaggaaauu cuuuagucug gcauugcauc agagugaaau cuuuuuguca   11820
aaacaccuga ggguccagcu aggcagucag caaauguagu cugagggca cucuuucccu    11880 guaagccagc acugcuuuac cugaaagccc uguagagaac cucuugcaug ugacuuaagc   11940
uauuuagaaa auccagcuag uagauuauuu aagaguucga uacguuaagu agcauuaaug   12000
acuccuuuuu aucaagauug cucuacaaaa uacagucugu aaauaugaca aaugacugua   12060
ugacacaaaa cagaauuaaa augccccauu agaauaaaa ugggcaguag uaaaaugaau    12120
gaggcagggg aaauuuauga ggguaauuga ucucucgguc auuaagcagg cucucuauug   12180
gcauuuaaca aaaauccauu ucagguacgu gcagccagca acaaccucca ccccauuac    12240 aaaauguuca uccagagaga gccaaaauaa cugagcaaau aaugaaaaua acaguggaaa   12300
uuacccuguu guacuguuaa cauaacguac ucagaaauac caaggacaca gugauuuuca   12360
ugccagcuau ccaaauagau cuuaguaaac uuucagcaac ugcacuaaca cagcuucugg   12420
aauuuaugau ggaguuuucu uguuuuaagg ugccauuauu cauggaagga guagaagagu   12480
accugguaau aauuuugcac ugcuaagucc caggcauuac cuguggcagg auuaauaucc   12540
ccaguuuagg auaauaaaau caaaacucua ugauucaccc uuuaauaaga gaacuucagg   12600 uucagcuccca ggcugcuuac cauuuucgc uuugaauaga ugccuuuuua aaaagugauu    12660
uccuggaugu gaagcugauc ugccugcaac aucugucacc ccaugauca ccaggguaga    12720 uucagcuuau cuggcuggcu aagcggugu ccccuuccuc ccacuguu ucacgugacu      12780 ccuucccgaa gcugcgcacu caguggaaga ggacgaccau cugcaauaga ggggacugg    12840 ucuuuuguca aggguauagg aguagcugug cuccccugcu agaaccucca aacaagcucu   12900
caagguucau aaacgugauu cuauuucaac uguuguauga ucaauaauug agcuucaucg   12960 ugauggguguu caaagauccc cgcacuuugg agucagggag ccucuacagc aauuccagcu   13020
uggaaugaga uucuucuaag cuguguccuca gcaaacauuu aacaucuaaca auguucuagg  13080 ugcuuacaga agccuuccu cuaccaccuua ugcaguacac cgcccuugcc ccaguccca    13140 ccuucaauca ccucuaucac auuaccaugg uuuauuucuc uuauagcacu aaucacuauu   13200
uaaaauuaac cagcugauuu auuucuuuac auauuuacug cccugaauua gaauauuagc   13260
cacaaaaggg cagagacccu uuccgucuua uuccacauug uauccccaga agccuucggc    13320 aaauggguaga ugucaauaga uaauaaucaa auugacuaau acacaauuua agccacuccu   13380
gcuucagacc caguaaauau acuguccuc cuucaaacac uuaaacuuca uuaucacaag    13440
cuaauaaagc aacuaaauaa aauugugaaa cauaauuuag uaauagacuu cuaaauaucc    13500
cagaagugua aaaucuuaua ugugggaaaug uucauugaga uacuaggcau ucuagggaua   13560
ucauggaaga aaaagacaua aucucuaccu gaaagacugu aaagguauag uuaaugagag   13620
ggagugaaga agcugaccug uagacaaauu acaauauaau aaguaaugcu guaaucaaau   13680
gauaaacaaa gggaagagua aaauuuucua cacgggagag ccagguuuca auaaaaauuu    13740
uauucuauaa aagcuuauau aaaauaauga uauucgagca uagacuugga aacuaaaaag    13800
agaaaggacu uccagccaga agucacagca ugagaaacgg gcaucauauu aaaucuuccu    13860
gauguuuuug augaaaaagc aauggauaau gagaaaggaa ggaaggugu uaguaauuug     13920
```

| | |
|---|---:|
| guugugacag accuugauua uagggcuaau gaguuaagau cugguuuuua aguacuggag | 13980 |
| aauuaccuca cucuauuucu gauacuucca agaaacugc aaaggugccu aaauauaaa | 14040 |
| aaauaaguag auaaugcaga aaucuguuca caaucagaua uugcaaguuc accucuagaa | 14100 |
| uauguacuga agaacuguga acaugggaaa uaacuuccag aaccaagcau auucagcauc | 14160 |
| uggugaugu ccuugcuuu ugcacaguga aaauaauguu uuugaggccg auuccaagu | 14220 |
| agaaaggaaa gacaauuaaa uuccuuucau acuacacuag acaagagaau gaaacuauag | 14280 |
| uggaaaaaua uugagauuuu uacucaaauc agcugcauca acaauuaaaa uucuaccaau | 14340 |
| accguggacu ucuucaggua gcaaugagaa cuccauccca agauauggac cgaggaugga | 14400 |
| augauaauuu ucaaaaauau uuguaaggag guuuaggugu caaauuguga cuugaauuug | 14460 |
| augaccuucu aagcccuucc ugauguuaug auucuguuuu aauuuauaua ugucaaaga | 14520 |
| cuauucaaau aaaaaacacc uucuaugcca ggugcuggaa acaaaaagau aaacauaaca | 14580 |
| cagucuagua uuuuaaaaua gugcuaaaacu cuacaauguu aucucugauu guucauacau | 14640 |
| aggcaggugc auagcuaagc ugcuuggcuu auccagcuau uugccgggau ggugggucac | 14700 |
| uguggucacc acacagaaau caauucuguu ucuuuguugu ucauuccag | 14749 |

<210> SEQ ID NO 63
<211> LENGTH: 1301
<212> TYPE: RNA
<213> ORGANISM: artificial
<220> FEATURE:
<223> OTHER INFORMATION: human intron 9 pre-mRNA IL-1RAcP

<400> SEQUENCE: 63

| | |
|---|---:|
| guaaguaaca gaaauuugac auaaaccucu ucuacuguca ucuuuagaac auauguugua | 60 |
| aaaaaagaa aaagaaaac auguugauuu gaaaaaccua gauuaacugg aagauuuaag | 120 |
| cagauuaacu uuaauuucaa ccguugcuau uagaaaucuu uccgaagauu auuauucuau | 180 |
| uuucuuggau uaauuaguga gucggucuaa auuaacacccc uccaaauaga aauauaaugc | 240 |
| gagccacuua ccuacuuaaa auuucccagu gaccacauua guaaaaguaa aagaaacaa | 300 |
| guaaaaauaa cgaauugacu aaauauauuu auaauacuau uuuuuagcau gcaauuaaua | 360 |
| uuaaaaagcu aaugagauau uuuaguguuu ucuuuggguac uaaaaauguu caaaauguaa | 420 |
| aauguauucu acuuuauccu uauagcacau ucaauucaa accagccaca uuucgaguga | 480 |
| gcaauagacu cgugacucgu ggcugcugua uuggacagug cugauccaca cuccuuguac | 540 |
| ucagauagag aucugugaac cagcagcaac auaucacgug uagcuuauua gaagaagaau | 600 |
| cuuagaccua gccccuacug acucagaauc uacauuuaaa ccauauuccc aagugauuca | 660 |
| uguuacguu aacaucugaa aagcacagcu cuaagugcaaa uuugcuuagu gaaaagaaua | 720 |
| gagcauuuaa acauacaaau ucauagaucc accccauaaa gauuuuaauu caguaggcuu | 780 |
| auggaagaaa cacggaaucg auaguuuuua augagaugug auuuuucuaa uuaagcaacu | 840 |
| ucgugaaaga uugguccauu aaaucuaauu auauuuuaa uuuuaguucu uuucagauau | 900 |
| aaauaauuca ggcaguuuca caagguuuua cucaauuugu auuuuaaga uauuaaugag | 960 |
| ugauaggcuu ggacaggaag uugaaauuuu cucuacagug uuaauugcca guaccuauga | 1020 |
| uuuaccuucu ggcuuuguua auuuacaguu gaaugggaca aaccucacuc uuuuuccacu | 1080 |
| guaaagcaac cuguaagaug agaguugagg auauaucaga uaacauucaa aauuacaucu | 1140 |
| ucaaauaguc guuugcgug gagacuuguu gcaaguagaa aaucgcacug gaaucuguca | 1200 |
| cauaaugaaa augcuaauaa ugcagaaguu agauuuaaga aaaauguaau gguauugaga | 1260 |

-continued aacuuuccua auuuacauug uaucugguguu ccuuuugcua g                    1301

<210> SEQ ID NO 64
<211> LENGTH: 47
<212> TYPE: RNA
<213> ORGANISM: artificial
<220> FEATURE:
<223> OTHER INFORMATION: human intron 8 - exon 9 IL-1RAcP pre-mRNA

<400> SEQUENCE: 64
ucuguuucuu uguuguucau uccagugcca gcuccaagau acacagu                  47

<210> SEQ ID NO 65
<211> LENGTH: 65
<212> TYPE: RNA
<213> ORGANISM: artificial
<220> FEATURE:
<223> OTHER INFORMATION: human exon 9 - intron 9 IL-1RAcP pre-mRNA

<400> SEQUENCE: 65
uuuuaccggg cucauuuugg aacagaugaa accauuuuag guaaguaaca gaaauuugac    60
auaaa                                                               65

<210> SEQ ID NO 66
<211> LENGTH: 20
<212> TYPE: DNA
<213> ORGANISM: Artificial
<220> FEATURE:
<223> OTHER INFORMATION: primer

<400> SEQUENCE: 66
ccggagagga gacttcacag                                               20

<210> SEQ ID NO 67
<211> LENGTH: 20
<212> TYPE: DNA
<213> ORGANISM: Artificial
<220> FEATURE:
<223> OTHER INFORMATION: primer

<400> SEQUENCE: 67
tccacgattt cccagagaac                                               20

<210> SEQ ID NO 68
<211> LENGTH: 23
<212> TYPE: DNA
<213> ORGANISM: Artificial
<220> FEATURE:
<223> OTHER INFORMATION: primer

<400> SEQUENCE: 68
ggcattgttc tctaatgtct ccg                                           23

<210> SEQ ID NO 69
<211> LENGTH: 22
<212> TYPE: DNA
<213> ORGANISM: Artificial
<220> FEATURE:
<223> OTHER INFORMATION: primer

<400> SEQUENCE: 69
gctccaggta tatccgagct tc                                            22

<210> SEQ ID NO 70

```
<211> LENGTH: 20
<212> TYPE: DNA
<213> ORGANISM: Artificial
<220> FEATURE:
<223> OTHER INFORMATION: primer

<400> SEQUENCE: 70
actgggacga catggagaag                                              20

<210> SEQ ID NO 71
<211> LENGTH: 20
<212> TYPE: DNA
<213> ORGANISM: Artificial
<220> FEATURE:
<223> OTHER INFORMATION: primer

<400> SEQUENCE: 71
ggtcatcttt tcacggttgg                                              20
```